United States Patent
Newman et al.

(10) Patent No.: US 7,632,500 B2
(45) Date of Patent: Dec. 15, 2009

(54) MONOCLONAL ANTIBODIES AGAINST HMGB1

(75) Inventors: Walter Newman, Boston, MA (US); Shixin Qin, Lexington, MA (US); Theresa L. O'Keefe, Waltham, MA (US); Robert A. Obar, Walpole, MA (US)

(73) Assignee: Cornerstone Therapeutics, Inc., Cary, NC (US)

( * ) Notice: Subject to any disclaimer, the term of this patent is extended or adjusted under 35 U.S.C. 154(b) by 148 days.

(21) Appl. No.: 11/903,129

(22) Filed: Sep. 20, 2007

(65) Prior Publication Data

US 2008/0113385 A1 May 15, 2008

Related U.S. Application Data

(62) Division of application No. 10/938,992, filed on Sep. 10, 2004, now Pat. No. 7,288,250.

(60) Provisional application No. 60/502,568, filed on Sep. 11, 2003.

(51) Int. Cl.
A61K 39/395 (2006.01)
C07K 16/24 (2006.01)

(52) U.S. Cl. .................. 424/134.1; 424/145.1; 435/810; 530/387.3

(58) Field of Classification Search ........................ None
See application file for complete search history.

(56) References Cited

U.S. PATENT DOCUMENTS

| | | | |
|---|---|---|---|
| 4,678,772 A | 7/1987 | Segal et al. |
| 4,835,142 A | 5/1989 | Suzuki et al. |
| 4,871,740 A | 10/1989 | Kurono et al. |
| 5,229,378 A | 7/1993 | Ogata et al. |
| 5,425,948 A | 6/1995 | Olivieri |
| 5,545,806 A | 8/1996 | Lonberg et al. |
| 5,545,807 A | 8/1996 | Surani et al. |
| 5,594,114 A | 1/1997 | Goodearl et al. |
| 5,605,690 A | 2/1997 | Jacobs et al. |
| 5,656,272 A | 8/1997 | Le et al. |
| 5,852,174 A | 12/1998 | Vlassara et al. |
| 5,864,018 A | 1/1999 | Morser et al. |
| 6,171,779 B1 | 1/2001 | Chada et al. |
| 6,177,077 B1 | 1/2001 | Tobinick |
| 6,303,321 B1 | 10/2001 | Tracey et al. |
| 6,323,329 B1 | 11/2001 | Bullerdiek |
| 6,329,339 B1 | 12/2001 | Pompei et al. |
| 6,448,223 B1 | 9/2002 | Tracey et al. |
| 6,468,533 B1 | 10/2002 | Tracey et al. |
| 6,468,555 B1 | 10/2002 | Nakamura |
| 6,677,321 B1 | 1/2004 | Levin |
| 6,720,472 B2 | 4/2004 | Chada et al. |
| 6,822,078 B2 | 11/2004 | Ozaki et al. |
| 7,060,504 B2 | 6/2006 | Tracey et al. |
| 7,097,838 B2 | 8/2006 | Tracey et al. |
| 7,151,082 B2 | 12/2006 | Tracey et al. |
| 7,192,917 B2 | 3/2007 | Tracey et al. |
| 7,220,723 B2 | 5/2007 | Tracey et al. |
| 7,288,250 B2 | 10/2007 | Newman, et al. |
| 7,304,034 B2 | 12/2007 | Tracey et al. |
| 7,537,908 B2 | 5/2009 | Tracey et al. |
| 2002/0009749 A1 | 1/2002 | Ozaki et al. |
| 2002/0122799 A1 | 9/2002 | Stern et al. |
| 2002/0193432 A1 | 12/2002 | Mjalli et al. |
| 2003/0017155 A1 | 1/2003 | Tracey et al. |
| 2003/0027260 A1 | 2/2003 | Goddard et al. |
| 2003/0032090 A1 | 2/2003 | Hardiman et al. |
| 2003/0032674 A1 | 2/2003 | Hwang |
| 2003/0060410 A1 | 3/2003 | Tracey et al. |
| 2003/0113323 A1 | 6/2003 | Tracey et al. |
| 2003/0143194 A1 | 7/2003 | Tracey et al. |
| 2004/0005316 A1 | 1/2004 | Tracey et al. |
| 2004/0120953 A1 | 6/2004 | Tracey et al. |
| 2004/0141948 A1 | 7/2004 | O'Keefe |
| 2006/0240019 A1 | 10/2006 | Tracey et al. |
| 2007/0238640 A1 | 10/2007 | Tracey et al. |
| 2008/0167234 A1 | 7/2008 | Tracey et al. |
| 2008/0214454 A1 | 9/2008 | Tracey et al. |
| 2009/0148453 A1 | 6/2009 | Newman et al. |

FOREIGN PATENT DOCUMENTS

EP 0 552 439 A1 7/1993

(Continued)

OTHER PUBLICATIONS

Abeyama, K., et al., "The N-terminal Domain of Thrombomodulin Sequesters High-Mobility Group -B1 Protein, a Novel Antiinflammatory Mechanism," *J. Clinical Investigation* 115(5):1267-1274, (May 2005).

Aderem, A. and Ulevitch, R.J., "Toll-Like Receptors in the Induction of the Innate Immune Response," *Nature*, 406:782-787 (2000).

Akamatsu, H., et al., "Mechanism of Anti-Inflammatory Action of Glycyrrhizin: Effect on Neutrophil Functions Including Reactive Oxygen Species Generation," *Planta Med.* 57(2):119-121 (1991).

Alleva, L. M., et al., "High Mobility Group Box 1 (HMGB1) Protein: Possible Amplification Signal in the Pathogenesis of Falciparum Malaria," *Trans. R. Soc. Trop. Med. Hyg.*, 99:171-174 (2005).

Andersson, U. and Erlandsson-Harris, H., "HMGB1 is a potent trigger of arthritis," *J. Internal Med.*, 255:344-350 (2004).

(Continued)

*Primary Examiner*—Ram R Shukla
*Assistant Examiner*—Zachary Skelding
(74) *Attorney, Agent, or Firm*—Hamilton Brook Smith & Reynolds P.C.

(57) ABSTRACT

In various embodiments, the present invention is drawn to antibodies or antigen-binding fragments thereof that bind to a vertebrate high mobility group box (HMGB) polypeptide, methods of detecting and/or identifying an agent that binds to an HMGB polypeptide, methods of treating a condition in a subject characterized by activation of an inflammatory cytokine cascade and methods of detecting an HMGB polypeptide in a sample.

7 Claims, 37 Drawing Sheets

FOREIGN PATENT DOCUMENTS

| | | |
|---|---|---|
| EP | 1 079 849 B1 | 1/2002 |
| EP | 1 757 937 A2 | 2/2007 |
| ES | 2137125 | 12/1999 |
| JP | 62-166897 A | 7/1987 |
| JP | 10 082788 | 3/1998 |
| JP | 2003-096099 | 4/2003 |
| JP | 2004 523579 | 8/2004 |
| WO | WO 96/25493 A1 | 8/1996 |
| WO | WO 97/23611 A2 | 7/1997 |
| WO | WO 98/50547 | 11/1998 |
| WO | WO 99/20756 A2 | 4/1999 |
| WO | WO 99/20756 A3 | 4/1999 |
| WO | WO 99/59609 A2 | 11/1999 |
| WO | WO 00/20621 A1 | 4/2000 |
| WO | WO 00/47104 A2 | 8/2000 |
| WO | WO 00/55174 A | 9/2000 |
| WO | WO 00/75358 A2 | 12/2000 |
| WO | WO 01/72993 A1 | 4/2001 |
| WO | WO 01/36488 A1 | 5/2001 |
| WO | WO 01/55386 A1 | 8/2001 |
| WO | WO 01/75067 A2 | 10/2001 |
| WO | WO 01/90151 A2 | 11/2001 |
| WO | WO 01/99210 A1 | 12/2001 |
| WO | WO 02/069965 A1 | 9/2002 |
| WO | WO 02/070007 A1 | 9/2002 |
| WO | WO 02/074301 A1 | 9/2002 |
| WO | WO 02/074337 A1 | 9/2002 |
| WO | WO 02/089743 A2 | 11/2002 |
| WO | WO 02/090520 A2 | 11/2002 |
| WO | WO 02/092004 A2 | 11/2002 |
| WO | WO 03/022296 A1 | 3/2003 |
| WO | WO 03/075921 A2 | 9/2003 |
| WO | WO 2004/004763 A2 | 1/2004 |
| WO | WO 2004/046345 A2 | 6/2004 |
| WO | WO 2005/026209 A2 | 3/2005 |
| WO | WO 2006/024547 A2 | 3/2006 |
| WO | WO 2007/011606 A2 | 1/2007 |
| WO | WO 2008/076758 | 6/2008 |

OTHER PUBLICATIONS

Andersson, U., et al., "HMGB1 as a DNA-ginding Cytokine," *J. Leukocyte Biol.* 72:1084-1091 (2002).

Attwood, T.K., "The Babel of Bioinformatics," *Science*, 290:471-473 (2000).

Azimov, M. M., et al., "Pharmacological Study of the Anti-Inflammatory Agent Glyderinine," *Farmakol. Toksikol.* 51(4):90-93 (1988). English Abstract.

Beutler, E., et al., "Synergy Between TLR2 and TLR4: A Safety Mechanism," *Blood Cells, Mol. Dis.*, 27(4):728-730 (2001).

Bianchi, E.V., et al., "Supression of ProinflammatoryCytokines in Monocytes by a Tetravalent Guanylhydrazone," *J. Exp. Med* 183:927-936 (Mar. 1996).

Bianchi, M.E. and Manfredi, A.A., "High-Mobility Group Box 1 (HMGB1) Protein at the Crossroads Between Innate and Adaptive Immunity," *Immunological Reviews* 220:35-46 (2007).

Bustin M., "Regulation of DNA-Dependent Activities by the functional Motifs of the High-Mobility-Group Chromosomal Proteins," *Mol. Cell. Biol.* 19(8):5237-46 (1999).

Cābart, P., et al., "Differential Expression of Nuclear HMG1, HMG2 Proteins and H10 Histone in Various Blood Cells," *Cell Biochemistry and Function* 13:125-133 (1995).

Czura, C.J., et al., "HMGB1 in the Immunology of Sepsis (not septic shock) and Arthritis," *Advances in Immunology* 84:181-200 (2004).

Dallman, M.J., "Cytokines and transplantation: Th1/Th2 regulation of the immune response to solid organ transplants in the adult," *Curr Opin Immunol*, 7:632-638 (1995).

Dorland's Illustrated Medical Dictionary, 28th ed. (Philadelphia, W.B. Saunders Co.), 1994, p. 269.

Dunn, M.D., Ph.D., D.L., "Role of Endotoxin and Host Cytokines in Spetic Shock," *Chest* 100(3):164S-168S (Sep. 1991 Supplement).

Fei, J., et al., "Study on High Mobility Group-1 Protein in Patients with Multiple Trauma," *Zhongguo Wei Zhong Bing Ji Jiu Yi Xue*, 17(5):273-275 (2005).

Fiuza, C., et al. "Inflammation-Promoting Activity of HMGB1 on Human Microvascular Endothelial Cells," *Blood* 101(7): 2652-2660 (2003).

Friend, P.J., et al., "Phase I Study of an Engineered Agycosylated Humanized CD3 Antibody in Renal Transplant Rejection," *Transplantation*, 68(11):1625-1626 (1999).

Goldstein, R.S., et al. "HMGB1 Detection in Patients with Cerebral and Myocardial Ischemia," J. Invest. Med., 53(2): S387 (2005) (Abstract From Joint Annual Meeting of the Central-Society-for-Clinical-Research/Midwestern American-Federation-for-Medical-Research).

"High Mobility Group, (HMG) Chromosomal Proteins Nomenclature Home Page" [online] [retrieved on Nov. 7, 2005], retrieved from the Internet :< URL: http://www.informatics.jax.org/mgihome/nomen/genefamilies/hmgfamily.shtml>.

Hori, O., et al., "The Receptor for Advanced Glycation End Products (RAGE) Is a Cellular Binding Site for Amphoterin," *J. Biol. Chem.*, 270(43):25752-25761 (1995).

HSTAT, Health Services/Technology Assessment Test. AHRQ Evidence Reports, No. 83, "Effect of Supplemental Antioxidants Vitamin C, Vitamin E, and Coenzyme Q10 for the Prevention and Treatment of Cardiovascular Disease," [online] [retrieved on Feb. 6, 2006]. Retrieved from the Internet: <URL:http://www.ncbi.nlm.nih gov/entrez/query.fcgi?cmd> p. 1/11-3/11.

Iwaki, D., et al., "The Extracellular Toll-Like Receptor 2 Domain Directly Binds Peptidoglycan Derived from *Staphylococcus aureus*," *J. Biol. Chem.*, 277(27):24315-24320 (2002).

Jones, B. W., et al., "Different Toll-Like Receptor Agonists Induce Distinct Macrophage Responses," *J. Leukoc. Biol.*, 69(6):1036-1044 (2001).

Kalinina, N., et al., "Increased Expression of the DNA-Binding Cytokine HMGB1 in Human Atherosclerotic Lesions: Role of Activated Macrophages and Cytokines," *Arterioscler. Thromb. Vasc. Biol.*, 24: 2320-2325 (2004).

Kim, J., et al., "Activation of Toll-Like Receptor 2 in Acne Triggers Inflammatory Cytokine Responses," *J. Immunol.*, 169(3):1535-1541 (2002).

Kirschning, C.J., et al., "Human Toll-Like Receptor 2 Confers Responsiveness to Bacterial Lipopolysaccharide," *J. Exp. Med.*, 188(11):2091-2097 (1998).

Kokkola, R., et al., "Successful Treatment of Collagen-Induced Arthritis in Mice and Rats by Targeting Extracellular High Mobility Group Box Chromosomal Protein 1 Activity," *Arthritis & Rheumatism* 48(7):2052-2058 (Jul. 2003).

Kokkola, R., et al., "High Mobility Group Box Chromosomal Protein 1," *Arthritis Rheum.*, 46(10):2598-2603 (2002).

Krenger, W. and Ferrara, J.L.M., "Graft-versus-Host Disease and the Th1/Th2 Paradigm," *Immunol Res*, 15:50-73 (1996).

Kuntz, I.D., "Structure-Based Strategies for Drug Design and Discovery," *Science*, 257:1078-1082 (1992).

Levy, M.M., et al., 2001 SCCM/ESICM/ACCP/ATS/SIS International Sepsis Definitions Conference, *Intensive Care Med* 29:530-538 (2003).

Li, M., et al., "Recombinant HMGB1 with cytokine-stimulating activity," *J. Immunol. Methods*, 289:211-223 (2004).

Li, M., et al., "An Essential Role of the NF-κB/Toll Like Receptor Pathway in Induction of Inflammatory and Tissue Repair Gene Expression by Necrotic Cells," J. Immunol., 166:7128-7135 (2001).

Maeda, S., et al., "Essential Roles of High-Mobility Group Box 1 in the Development of Murine colitis and Colitis-Associated Cancer," *Biochemical and Biophysical Research Communications*, 360: 394-400 (2007).

Martin, M., et al., "Role of Innate Immune Factors in the Adjuvant Activity of Monophosphoryl Lipid A," *Infect. Immun.*, 71(5):2498-2507 (2003).

Matsuguchi, T., et al., "Gene Expressions of Toll-Like Receptor 2, But Not Toll-Like Receptor 4, Is Induced by LPS and Inflammatory Cytokines in Mouse Macrophages," *J. Immunol*, 165(10): 5767-5772 (2000).

Means, T. K., et al., "Human Toll-Like Receptors Mediate Cellular Activation by *Mycobacterium tuberculosis*," *J. Immunol.*, 3920-3927 (1999).

Mcldrum, D.R., "Tumor Necrosis Factor in the Heart," *Am. J. Physiol.* 274: R577-R595 (1998).

Meng, G., et al., "Antagonistic antibody prevents toll-like receptor 2-driven lethal shock-like syndromes," *J. Clin. Invest.*, 113(1):1473-1481 (2004).

Meng, G., et al., "Murine TLR2 expression anaylsis and systemic antagonism by usage of specific monoclonal antibodies," *Immunology Letters*, 98:200-207 (2005).

Miller, D.W. and Dill, Ken A., "Ligand binding to proteins: The binding landscape model," *Prot Sci*, 6:2166-2179 (1997).

Ombrellino, M., et al., "Increased Serum Concentrations of High-Mobility-Group Protein 1 in Haemorrhagic Shock," *Lancet* 354 (9188):1446-1447 (1999).

Opal, S.M. and Huber, C.E., "Bench-To-Bedside Review: Toll-Like Receptors and Their Role in Septic Shock," *Crit. Care*, 6(2):125-136 (2002).

Østerud, B., et al., "Role of Monocytes in Atherogenesis," *Physiol. Rev.* 83(4):1069-1112 (2003).

Ozaki, S., "High Mobility Group Protein HMG1/HMG2: Clinical Significance of the Autoantibodies," *Jpn. J. Clin. Immun.*, 21(3)95-107 (1998).

Park, J.S. et al., "Involvement of Toll-like Receptors 2 and 4 in Cellular Activation bby High Mobility Group Box 1 Protein," *J. Biol. Chem.* 279(9):7370-77 (2004).

Patel, M., et al., "TLR2 Agonist Ameliorates Established Allergic Airway Inflammation by Promoting Th1 Response and Not via Regulatory T Cells," *J. Immunol*, 174:7558-7563 (2005).

Poltorak, A., et al., "Defective LPS Signaling in C3H/HeJ and C57BL/10ScCr Mice: Mutations in Tlr4 Gene," *Science* 282:2085-2088 (1998).

Popovic, K., et al., "Increased Expression of the Novel Proinflammatory Cytokine HMGB1 is Detected in Cutaneous lupus Erythematosus Lesions," J. Investigative Dermatology 123(2): & 34th Annual Meeting of the European Society for Dermatological Research, Vienna, Austria, Sep. 2004.

Popovic, K., et al., "Increased-Expression of the Novel Proinflammatory Cytokine High Mobility Group Box Chromosomal Protein 1 in Skin Lesions of Patients With Lupus erythematosus," *Arthritis &Rheumatism* 52(11):3639-3645 (Nov. 2005).

Reeves, R. and Nissen, M.S., "The A•T-DNA-binding Domain of Mammalian High Mobility Group I Chromosomal Proteins," J. Biol. Chem., 265(15):8573-8582 (1990).

Riedemann, N.C., et al., "Novel Strategies for the Treatment of Sepsis," *Nature Med.*, 9(5):517-524 (2003).

Rogalla, P., et al., "Mapping and molecular characterization of five HMG1-related DNA sequences," *Cytogenet Cell Genet*, 83:124-129 (1998).

Romine, L.E., et al., "The High Mobility Group Protein 1 Enhances Binding of the Estrogen Receptor DNA Binding Domain to the Estrogen Response Element," *Molecular Endocrinology* 12:664-674 (1998).

Sakamoto, R., et al., "Inhibitory Effect of Glycyrrhizin on the Phosphorylation and DNA-Binding Abilities of High Mobility Group Proteins 1 and 2 in Vitro," *Biol. Pharm. Bull.* 24(8):906-911 (2001).

Schmidt, A.M., et al., "The Multiligand Receptor RAGE as a Progression Factor Amplifying Immune and Inflammatory Responses," *J. Clinical Investigation* 108(7):949-955 (Oct. 2001).

Stedman's Medical Dictionary, 26th ed. (Baltimore, Williams & Wilkins) 1995, p. 283.

Straino, Stefania, et al., "High-Mobility Group Box 1 Protein in Human and Murine Skin: Involvement in Wound Healing," *J. of Investigative Dermatology* 10:1-9 (Jan. 2008).

Swiss-PROT Accession No. P09429, "High Mobility Group Protein 1 (HMG-1) (High Mobility Group Protein B1)," (2006) [online] [retrieved on Mar. 9, 2006], Retrieved from the Internet:<URL:http://www.ncbi.nlm.nih.gov>.

Tabeta, K. et al., "Toll-Like Receptors Confer Responsiveness to Lipopolysaccharide From *Porphyromonas gingivalis* in Human Gingival Fibroblasts," *Infect Immun.* 68(6):3731-3735 (2000).

Taguchi, A., et al., "Blockade of RAGE-amphoterin Signalling Suppresses Tumour Growth and Metastases," *Nature*, 405:354-360 (2000).

Taniguchi, N., et al., "High Mobility Group Box Chromosomal Protein 1 Plays a Role in the Pathogenesis of Rheumatoid arthritis as a Novel Cytokine," *Arthritis Rheum.*, 48(4):971-981 (2003).

Taudte, S., et al., "Interactions Between HMG Boxes," *Protein Eng.*, 14(12):1015-1023 (2001).

Toogood, G.J., et al., "The Immune Response following Small Bowel Transplantation," *Transplantation*, 62 (6):851-855 (1996).

Tsuda, K., et al., "Primary Structure of Non-Histone Protein HMG1 Revealed by the Nucleotide Sequence," *Biochemistry*, 27:6159-6163 (1988).

Tsung, A., et al., "The Nuclear Factor HMGB1 Mediates Hepatic Injury After Murine Liver Ischemia-Reperfusion," Journal of Experimental Medicine 201(7): 1135-1143 (2005).

Waterston, A.M. et al., "TNF Autovaccination Induces Self Anti-TNF Antibodies and Inhibits Metastasis in a Murine melanoma Model," *Br. J. Cancer* 90(6):1279-84 (2004).

Weir, H.M., et al., "Structure of the HMG Box Motif in the B-Domain of HMG1," *EMBO Journal*, 12(4):1311-1319 (1993).

Wisniewski, J.R., et al., "Region of Insect High Mobility Group (HMG)1 Protein Homologous of Helix 2 of the Rat HMG1-B Box is in Close Contact with DNA," *J. Biol. Chem.* 269(46):29261-29264 (1994).

Wood, R.F.M. and Pockley, A.J. review of Friend, P.J., et al., "Phase I Study of an Engineered Agycosylated Humanized CD3 Antibody in Renal Transplant Rejection," *Transplantation*, 68(11):1625-1626 (1999).

Yakushijin, T., et al., "Reduced expression and functional impairment of Toll-like receptor 2 on dendritic cells in chronic hepatitis C virus infection," *Hepatology Research*, 34:156-162 (2006).

Yang H., et al., "HMG-1 Rediscovered as a Cytokine," *Shock* 15:247-53 (2001).

Yang, R-B., et al., "Signaling Events Induced by Lipopolysaccharide-Activated Toll-Like Receptor 2," *J. Immunol.*, 163:639-643 (1999).

Yang, R-B., et al., "Toll-Like Receptor-2 Mediates Lipopolysaccharide-Induced Cellular Signalling," Nature, 395:284-288 (1998).

Yasuda, T., et al., "Significant Increase of Serum High-Mobility Group Box Chromosomal Protein 1 Levels in Patients with Severe Acute Pancreatitis,"*Pancreas*,33(4): 359-363 (2006).

Notification of Transmittal of the International Search Report or the Declaration (ISR) with ISR, PCT/US02/15329, mailed Jun. 20, 2003.

Written Opinion, PCT/US02/15329, mailed Jun. 20, 2003.

Notification of Trasnmittal of International Preliminary Examination Report (IPER) with IPER, PCT/US02/15329, mailed Nov. 29, 2004.

Suppl. Partial European Search Report, EP 02 73 6852, mailed Jul. 26, 2006.

Suppl. Partial ESR (incomplete), EP 00 91 5762, mailed Jun. 4, 2002.

International Search Report (ISR), PCT/US00/03583, mailed May 23, 2001.

Written Opinion (WO), PCT/US00/03583, mailed Oct. 31, 2001.

Partial European Search Report, EP05 07 7852, mailed Aug. 18, 2006.

Partial European Search Report, EP06 07 5291.2, mailed Jan. 22, 2007.

Invitation to Pay Additional Fees, PCT/US2004/029527, mailed May 17, 2005.

Notification of Transmittal of the International Search Report (ISR) and the Written Opinion (WO) of the International Searching Authority, or the Declaration, with ISR and WO, PCT/US2004/029527, mailed May 17, 2005.

Notification Concerning Transmittal of International Preliminary Report on Patentability (IPRP), with IPRP, PCT/US2004/029527, mailed Mar. 23, 2006.

Invitation to Pay Additional Fees, PCT/US2006/027053, mailed Feb. 7, 2007.

Notification of Transmittal of the International Search Report (ISR) and the Written Opinion (WO) of the International Searching Authority, or the Declaration, with ISR and WO, PCT/US2006/027053, mailed May 15, 2007.

Notification Concerning Transmittal of International Preliminary Report on Patentability (IPRP), with IPRP, PCT/US2006/027053, mailed Jan. 31, 2008.

Kabir, S., et al., "Serum Levels of Interleukin-1, Interleukin-6 and Tumour Necrosis Factor-Alpha in Patients With Gastric Carcinoma," *Cancer Letters* 95:207-212 (1995).

Kakumu, S., et al., "Serum Levels of IL-10, IL-15 and Soluble Tumour Necrosis Factor-alpha (TNF-α) Receptors in Type C Chronic Liver Disease," *Clin. Exp. Immunol.*, 109:458-463 (1997).

Kawahara, N., et al., "Enhanced Coexpression of Thioredoxin and High Mobility Group Protein 1 Genes in Human Hepatocellular Carcinoma and the Possible Association With Decreased Sensitivity to Cisplatin," *Cancer Research* 56:5330-5333 (1996).

Xiang, Y., et al., "Expression of High-Mobility Group-1 mRNA in Human Gastrointestinal Adenocarcinoma and Corresponding Non-Cancerous Mucosa," *Int. J. Cancer* (Pred. Oncol.) 74:1-6 (1997).

Abaza, M.-S. I. and Atassi, M. Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J. Protein Chem.* 11(5):433-444 (1992).

Abraham, E., et al., "Cutting Edge: HMG-1 as a Mediator of Acute Lung Inflammation," *J. Immunol.*, 165:2950-2954 (2000).

Andersson, U., et al., "High Mobility Group 1 Protein (HMG-1) Stimulates Proinflammatory Cytokine Synthesis in Human Monocytes," *J. Exp. Med.*, 192:565-570 (2000).

Ayer, L. M., et al., "Antibodies to HMG Proteins in Patients With Drug-Induced Autoimmunity," *Arthritis Rheum.*, 37(1):98-103 (1994).

Banks, G. C., et al., "The HMG-I(Y) A T-hook Peptide Motif Confers DNA-binding Specificity to a Structured Chimeric Protein," *J. Biol. Chem.*, 274(23):16536-16544 (1999).

Baxevanis, A.D., et al., "The HMG-1 Box Protein Family: Classification and Functional Relationships", *Nucleic Acids Res.*, 23(9):1604-1613 (1995).

Benjamini, E., "Antigenicity" in *Immunology, A Short Course*, (NY:Wiley-Liss), p. 40 (1991).

Bianchi, M. E., et al., "Specific Recognition of Cruciform DNA by Nuclear Protein HMG1," *Science*, 243:1056-1059 (1989).

Bianchi, M.E., et al., "The DNA Binding Site of HMG1 Protein is Composed of Two Similar Segments (HMG Boxes), Both of Which Have Counterparts in Other Eukaryotic Regulatory Proteins," *EMBO J.* 11(3):1055-1063 (1992).

Bustin, M. "Revised Nomenclature for High Mobility Group (HMG) Chromosomal Proteins," *Trends Biochem. Sci.*, 26:152-153 (2001).

Bustin, M., et al., "Antigenic Determinants of High Mobility Group Chromosomal Proteins 1 and 2," *Biochem.*, 21:6773-6777 (1982).

Bustin, M., et al., "Immunological Relatedness of High Mobility Group Chromosomal Proteins from Calf thymus,"*J. Biol. Chem.*, 253(5):1694-1699 (1978).

Chou, D. K. H., et al., "Identity of Nuclear High-Mobility-Group Protein, HMG-1, and Sulfoglucuronyl Carbohydrate-Binding Protein, SBP-1, in Brain," *J. Neurochem.*, 77:120-131 (2001).

Clackson, T., et al., "Making Antibody Fragments Using Phage Display Libraries," *Nature*, 352:624-628 (1991).

Colman, P. M., "Effects of Amino Acid Sequence Changes on Antibody-Antigen Interactions," *Res. Immunol.*, 145(1):33-36 (1994).

Czura, C., et al., "Dual Roles for HMGB1: DNA Binding and Cytokine," *J. Endotoxin Res.*, 7(4):315-321 (2001).

Czura, C., et al., "High Mobility Group Box-1 as a Therapeutic Target Downstream of Tumor Necrosis Factor," *J. Infect. Dis.*, 187 (Supp. 2):S391-S396 (2003).

Daston, M. and Ratner, N., "Expression of P30, a Protein with Adhesive Properties, in Schwann Cells and Neurons of the Developing and Regenerating Peripheral Nerve," *J. Cell Biol.*, 112(6):1229-1239 (1991).

Degryse, B., et al., "The High Mobility Group (HMG) Boxes of the Nuclear Protein HMG1 Induce Chemotaxis and Cytoskeleton Reorganization in Rat Smooth Muscle Cells," *J. Cell Biol.*, 152:1197-1206 (2001).

Falciola, L., et al., "High Mobility Group 1 Protein is Not Stably Associated with the Chromosomes of Somatic Cells," *J. Cell Biol.*, 137 (1):19-26 (1997).

Freeman, B. D., et al., "The Role of Inflammation in Sepsis and Septic Shock: A Meta-Analysis of Both Clinical and Preclinical Trials of Anti-Inflammatory Therapies," in *Inflammation: Basic Principals and Clinical Correlates* (John I. Gallin and Ralph Snyderman eds., Lippincott, Williams & Wilkins, Philadelphia, 3rd ed. 1999), pp. 965-975.

GenBank Accession No. AAA20508, "HMG-1," (1994) [online] [retrieved on Mar. 21, 2006]. Retrieved from the Internet: <URL:http://www.ncbi.nlm.nih.gov/entrez/viewer.fcgi?db=protein&val=437102>.

GenBank Accession No. AAA64970, "HMG-1," (1995) [online] [retrieved on Sep. 30, 2004]. Retrieved from the Internet: <URL:http://www.ncbi.nlm.nih.gov/entrez/viewer.fegi?db=protein&val=184251>.

GenBank Accession No. AAB08987, "Non-Histone Chromatin Protein HMG 1 [*Homo sapiens*]," (1996) [online] [retrieved on Mar. 21, 2006]. Retrieved from the Internet: <URL:http://www.ncbi.nlm.nih.gov/entrez/viewer.fcgi?db=protein&val=1435197>.

GenBank Accession No. AB009451, "Alternaria alternata MAT1 Gene, Complete cds," (2002) [online] [retrieved on Mar. 21, 2006]. Retrieved from the Internet: <URL:http://www.ncbi.nlm.nih.gov/entrez/viewer.fcgi?db=nuccore&val=4520345>.

GenBank Accession No. AC010149, "*Homo sapiens* BAC clone RP11-395A23 from 2, complete sequence," (2005) [online] [retrieved on Apr. 18, 2006]. Retrieved from the Internet: <URL:http://www.ncbi.nlm.nih.gov/entrez/viewer.fcgi?db=nuccore&val=14151041>.

GenBank Accession No. AF076674, "*Homo sapiens* high mobility group 1-like protein L1 (HMG1L1) retropseudogene sequence," (1999) [online] [retrieved on Apr. 18, 2006]. Retrieved from the Internet: <URL:http://www.ncbi.nlm.nih.gov/entrez/viewer.fcgi?db=nuccore&val=4884556>.

GenBank Accession No. AF076676, "*Homo sapiens* high mobility group 1-like protein L4 (HMG1L4) retropseudogene sequence," (1999) [online] [retrieved on Apr. 18, 2006]. Retrieved from the Internet: <URL:http://www.ncbi.nlm.nih.gov/entrez/viewer.fcgi?db=nuccore&val=4884558>.

GenBank Accession No. AF107043, "*Homo sapiens* Clone pCL11 DNA-binding Protein SOX14 (SOX14) Gene, Complete cds," (1998) [online] [retrieved on Mar. 21, 2006]. Retrieved from the Internet: <URL:http://www.ncbi.nlm.nih.gov/entrez/viewer.fcgi?db=nuccore&val=4008100>.

GenBank Accession No. AF107044, "*Homo sapiens* Clone pCL4 DNA-binding Protein SOX21 (SOX21) Gene, Complete cds," (1998) [online] [retrieved on Mar. 21, 2006]. Retrieved from the Internet: <URL:http://www.ncbi.nlm.nih.gov/entrez/viewer.fcgi?db=nuccore&val=4008102>.

GenBank Accession No. AF165167, "*Homo sapiens* high mobility group 1-like protein L8 (HMG1L8) retropseudogene, complete sequence," (2001) [online] [retrieved on Apr. 18, 2006]. Retrieved from the Internet: <URL:http://www.ncbi.nlm.nih.gov/entrez/viewer.fcgi?db=nuccore&val=15027608>.

GenBank Accession No. AF165168, "*Homo sapiens* high mobility group 1-like protein L9 (HMG1L9) retropseudogene, complete sequence," (2001) [online] [retrieved on Apr. 18, 2006]. Retrieved from the Internet: <URL:http://www.ncbi.nlm.nih.gov/entrez/viewer.fcgi?db=nuccore&val=15027609>.

GenBank Accession No. AF226675, "*Homo sapiens* Transcription Factor SOX8 mRNA, Complete cds," (2000) [online] [retrieved on Mar. 21, 2006]. Retrieved from the Internet: <URL:http://www.ncbi.nlm.nih.gov/entrez/viewer.fcgi?db=nuccore&val-7025446>.

GenBank Accession No. AF309034, "*Homo sapiens* SOX6 mRNA, Complete cds," (2001) [online] [retrieved on Mar. 21, 2006]. Retrieved from the Internet: <URL:http://www.ncbi.nlm.nih.gov/entrez/viewer.fcgi?db=nuccore&val=13435017>.

GenBank Accession No. AJ001183, "*Homo sapiens* mRNA for Sox10 Protein," (2005) [online] [retrieved on Mar. 21, 2006]. Retrieved from the Internet: <URL:http://www.ncbi.nlm.nih.gov/entrez/viewer.fcgi?db=nuccore&val=2909359>.

GenBank Accession No. CAA31110, "Unnamed Protein Product [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=32327>.

GenBank Accession No. D30765, "*Xenopus laevis* mRNA for HMG-X Protein, Complete cds," (1999) [online] [retrieved on Mar. 21, 2006]. Retrieved from the Internet: <URL:http://www.ncbi.nlm.nih.gov/entrez/viewer.fcgi?db=nuccore&val=639690>.

GenBank Accession No. J04197, "*Rattus norvegicus* 6-phosphofructo-2-kinase/fructose-2, 6-bisphosphatase mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=202557>.

GenBank Accession No. L17131, "*Homo sapiens* High Mobility Group Protein (HMG-I(Y)) Gene Exons 1-8, Complete cds" (1999) [online] [retrieved on Mar. 21, 2006]. Retrieved from the Internet: <URL:http://www.ncbi.nlm.nih.gov/entrez/viewer.fcgi?db=nuccore&val=306868>.

GenBank Accession No. L32859, "Rainbow Trout HMG-I Gene Exons 2-5, Complete cds," (1995) [online] [retrieved on Mar. 21, 2006]. Retrieved from the Internet: <URL:http://www.ncbi.nlm.nih.gov/entrez/viewer.fcgi?db=nuccore&val=609550>.

GenBank Accession No. M23618, "Human HMG-Y Protein Isoform mRNA (HMGI gene), Clone 11D," (1996) [online] [retrieved on Mar. 21, 2006]. Retrieved from the Internet: <URL:http://www.ncbi.nlm.nih.gov/entrez/viewer.fcgi?db=nuccore&val=184258>.

GenBank Accession No. M62810, "Human Mitochondrial Transcription Factor 1 mRNA, Complete cds," (1995) [online] [retrieved on Mar. 21, 2006]. Retrieved from the Internet: <URL:http://www.ncbi.nlm.nih.gov/entrez/viewer.fcgi?db=nuccore&val=188563>.

GenBank Accession No. M74017, "*T. brucei* Rhodesiense HMG1-like Protein mRNA, Complete cds" (1993) [online] [retrieved on Mar. 21, 2006]. Retrieved from the Internet: <URL:http://www.ncbi.nlm.nih.gov/entrez/viewer.fcgi?db=nuccore&val=162108>.

GenBank Accession No. M83665, "Human High Mobility Group 2 Protein (HMG-2) gene, Complete cds," (1994) [online] [retrieved on Sep. 24, 2004]. Retrieved from the Internet: <URL:http://www.ncbi.nlm.nih.gov/entrez/viewer.fcgi?db=nuccore&val=184235>.

GenBank Accession No. M86737, "Human High Mobility Group Box (SSRP1) mRNA, Complete cds," (1994) [online] [retrieved on Mar. 21, 2006]. Retrieved from the Internet: <URL:http://www.ncbi.nlm.nih.gov/entrez/viewer.fcgi?db=nuccore&val=184241>.

GenBank Accession No. NG_000897, "*Homo sapiens* high-mobility group (nonhistone chromosomal) protein 1-like 5 (HMG1L5) pseudogene on chromosome 3," (2006) [online] [retrieved on Apr. 18, 2006]. Retrieved from the Internet: <URL:http://www.ncbi.nlm.nih.gov/entrez/viewer.fcgi?db=nuccore&val=27502364>.

GenBank Accession No. NM_005342, "*Homo sapiens* High-mobility Group Box 3 (HMGB3), mRNA," (2005) [online] [retrieved on Mar. 21, 2006]. Retrieved from the Internet: <URL:http://www.ncbi.nlm.nih.gov/entrez/viewer.fcgi?db=nuccore&val=71143136>.

GenBank Accession No. NM_016957, "*Mus musculus* High Mobility Group Nucleosomal Binding Domain 2 (Hmgn2), mRNA," (2006) [online] [retrieved on Mar. 21, 2006]. Retrieved from the Internet: <URL:http://www.ncbi.nlm.nih.gov/entrez/viewer.fcgi?db=nuccore&val=86198321>.

GenBank Accession No. NP_002119, "High-Mobility Group Box 1 [*Homo sapiens*]," (2006) [online] [retrieved on Mar. 21, 2006]. Retrieved from the Internet: <URL:http://www.ncbi.nlm.nih.gov/entrez/viewer.fcgi?db=protein&val=4504425>.

GenBank Accession No. NP_005333, "High-Mobility Group Box 3 [*Homo sapiens*]," (2005) [online] [retrieved on Mar. 21, 2006]. Retrieved from the Internet: <URL:http://www.ncbi.nlm.nih.gov/entrez/viewer.fcgi?db=protein&val=71143137>.

GenBank Accession No. O00479, "Nonhistone Chromosomal Protein HMG-17-like 3 (Non-Histone Chromosomal Protein) (High-Mobility Group Nucleosome Binding Domain 4)," (2005) [online] [retrieved on Mar. 21, 2006]. Retrieved from the Internet: <URL:http://www.ncbi.nlm.nih.gov/entrez/viewer.fcgi?db=protein&val=20138140>.

GenBank Accession No. P05114, "Nonhistone Chromosomal Protein HMG-14 (High-Mobility Group Nucleosome-Binding Domain 1)," (1987) [online] [retrieved on Mar. 24, 2006]. Retrieved from the Internet: <URL:http://www.ncbi.nlm.nih.gov/entrez/viewer.fcgi?db=protein&val=123101>.

GenBank Accession No. P07155, "High Mobility Group Protein 1 (HMG-1) (Amphoterin) (Heparin-Binding Protein p30)," (2004) [online] [retrieved on Mar. 21, 2006]. Retrieved from the Internet: <URL:http://www.ncbi.nlm.nih.gov/entrez/viewer.fcgi?db=protein&val=1708258>.

GenBank Accession No. P09429, "High Mobility Group Protein 1 (HMG-1) (High Mobility Group Protein B1)," (1989) [online] [retrieved on Mar. 21, 2006]. Retrieved from the Internet: <URL:http://www.ncbi.nlm.nih.gov/entrez/viewer.fcgi?db=protein&val=123369>.

GenBank Accession No. S02826, "Nonhistone Chromosomal Protein HMG-1—human," (1999) [online] [retrieved on Apr. 18, 2006]. Retrieved from the Internet: <URL:http://www.ncbi.nlm.nih.gov/entrez/viewer.fcgi?db=protein&val=88270>.

GenBank Accession No. S29857, "Nonhistone Chromosomal Protein HMG-1—Human," (1999) [online] [retrieved on Mar. 21, 2006]. Retrieved from the Internet: <URL:http://wwvv.ncbi.nlm.nih.gov/entrez/viewer.fcgi?db=protein&val=478813>.

GenBank Accession No. U00431, "*Mus musculus* HMG-1 mRNA, Complete cds" (1994) [online] [retrieved on Mar. 21, 2006]. Retrieved from the Internet: <URL:http://www.ncbi.nlm.nih.gov/entrez/viewer.fcgi?db=nuccore&val=437101>.

GenBank Accession No. U13695, "Human Homolog of Yeast mutL (hPMS1) Gene, Complete cds," (1995) [online] [retrieved on Mar. 21, 2006]. Retrieved from the Internet: <URL:http://www.ncbi.nlm.nih.gov/entrez/viewer.fcgi?db=nuccore&val=535512>.

GenBank Accession No. U36501, "Human SP100-B (SP100-B) mRNA, Complete cds," (1996) [online] [retrieved on Mar. 21, 2006]. Retrieved from the Internet: <URL:http://www.ncbi.nlm.nih.gov/entrez/viewer.fcgi?db=nuccore&val=1173655>.

GenBank Accession No. U51677, "Human Non-histone Chromatin Protein HMG1 (HMG1) Gene Complete cds," (1996) [online] [retrieved on Mar. 21, 2006]. Retrieved from the Internet: <URL:http://www.ncbi.nlm.nih.gov/entrez/viewer.fcgi?db=nuccore&val=1435196>.

GenBank Accession No. X02666, "Trout mRNA for High Mobility Group Protein HMG-T," (2005) [online] [retrieved on Mar. 21, 2006]. Retrieved from the Internet: <URL:http://www.ncbi.nlm.nih.gov/entrez/viewer.fcgi?db=—nuccore&val=64327>.

GenBank Accession No. X13546, "Human HMG-17 Gene for Non-histone Chromosomal Protein HMG-17," (1997) [online] [retrieved on Mar. 21, 2006]. Retrieved from the Internet: <URL:http://www.ncbi.nlm.nih.gov/entrez/viewer.fcgi?db=nuccore&val=32328>.

GenBank Accession No. X53390, "Human mRNA for Upstream Binding Factor (hUBF)," (1999) [online] [retrieved on Mar. 21, 2006]. Retrieved from the Internet: <URL:http://www.ncbi.nlm.nih.gov/entrez/viewer.fcgi?db=nuccore&val=509240>.

GenBank Accession No. X53431, "Yeast Gene for STE11," (2005) [online] [retrieved on Mar. 21, 2006]. Retrieved from the Internet: <URL:http://www.ncbi.nlm.nih.gov/entrez/viewer.fcgi?db=nuccore&val=4553>.

GenBank Accession No. X53772, "*H. sapiens* SRY Gene," (1997) [online] [retrieved on Mar. 21, 2006]. Retrieved from the Internet: <URL:http://www.ncbi.nlm.nih.gov/entrez/viewer.fcgi?db=nuccore&val=36604>.

GenBank Accession No. X58636, "Mouse LEF1 mRNA for Lymphoid Enhancer Binding Factor 1," (1999) [online] [retrieved on Mar. 21, 2006]. Retrieved from the Internet: <URL:http://www.ncbi.nlm.nih.gov/entrez/viewer.fcgi?db=nuccore&val=52887>.

GenBank Accession No. X59869, "Human TCF-1 mRNA for T Cell Factor 1 (Splice Form A)," (2005) [online] [retrieved on Mar. 21, 2006]. Retrieved from the Internet: <URL:http://www.ncbi.nlm.nih.gov/entrez/viewer.fcgi?db=nuccore&val=36785>.

GenBank Accession No. X67668, "*M. musculus* mRNA for High Mobility Group 2 Protein," (2005) [online] [retrieved on Mar. 21, 2006]. Retrieved from the Internet: <URL:http://www.ncbi.nlm.nih.gov/entrez/viewer.fcgi?db=nuccore&val=51338>.

GenBank Accession No. X67668, "*M.musculus* mRNA for high mobility group 2 protein," (2005) [online] [retrieved on Apr. 18, 2006]. Retrieved from the Internet: <URL:http://www.ncbi.nlm.nih.gov/entrez/viewer.fcgi?db=nuccore&val=51338>.

GenBank Accession No. X71135, "*H. sapiens* Sox3 Gene," (2005) [online] [retrieved on Mar. 21, 2006]. Retrieved from the Internet: <URL:http://www.ncbi.nlm.nih.gov/entrez/viewer.fcgi?db=nuccore&val=468790>.

GenBank Accession No. X71138, "*D. melanogaster* HMG-D mRNA," (1993) [online] [retrieved on Mar. 21, 2006]. Retrieved from the Internet: <URL:http://www.ncbi.nlm.nih.gov/entrez/viewer.fcgi?db=nuccore&val=296942>.

GenBank Accession No. X71139, "*D. melanogaster* HMG-Z mRNA," (2005) [online] [retrieved on Mar. 21, 2006]. Retrieved from the Internet: <URL:http://www.ncbi.nlm.nih.gov/entrez/viewer.fcgi?db=nuccore&val=296944>.

GenBank Accession No. X73039, "*H. sapiens* SOX-12 Gene," (2005) [online] [retrieved on Mar. 21, 2006]. Retrieved from the Internet: <URL:http://www.ncbi.nlm.nih.gov/entrez/viewer.fcgi?db=nuccore&val=312151>.

GenBank Accession No. XM_063129, "*Homo sapiens* similar to high mobility group 1 (LOC122441), mRNA," (2002) [online] [retrieved on Apr. 18, 2006]. Retrieved from the Internet: <URL:http://www.ncbi.nlm.nih.gov/entrez/viewer.fcgi?db=nuccore&val=17453404>.

GenBank Accession No. XM_066789, "*Homo sapiens* similar to high mobility group 1 (LOC139603), mRNA," (2002) [online] [retrieved on Apr. 18, 2006]. Retrieved from the Internet: <URL:http://wwW.ncbi.nlm.nih.gov/entrez/viewer.fcgi?db=nuccore&val=17486193>.

GenBank Accession No. Y13436, "*Homo sapiens* Sox1 Gene," (2005) [online] [retrieved on Mar. 21, 2006]. Retrieved from the Internet: <URL:http://www.ncbi.nlm.nih.gov/entrez/viewer.fcgi?db=nuccore&val=4128158>.

GenBank Accession No. Z11540, "*T. aestivum* mRNA for High Mobility Group Protein (HMGW)," (2005) [online] [retrieved on Mar. 21, 2006]. Retrieved from the Internet: <URL:http://www.ncbi.nlm.nih.gov/entrez/viewer.fcgi?db=nuccore&val=21802>.

GenBank Accession No. Z31560, "*H. sapiens* Sox-2 mRNA (partial)," (2005) [online] [retrieved on Mar. 21, 2006]. Retrieved from the Internet: <URL:http://www.ncbi.nlm.nih.gov/entrez/viewer.fcgi?db=nuccore&val=854181>.

GenBank Accession No. Z48008, "*S. cerevisiae* Chromosome IV Cosmid 8119," (2005) [online] [retrieved on Mar. 21, 2006]. Retrieved from the Internet: <URL:http://www.ncbi.nlm.nih.gov/entrez/viewer.fcgi?db=nuccore&val=642799>.

Huttunen, H.J., "Receptor for Advanced Glycation End Products-Binding COOH-Terminal Motif of Amphoterin Inhibits Invasive Migration and Metastasis," *Cancer Res.*, 62(16)4805-4811 (2002).

Imamura, T., et al., "Interaction with p53 Enhances Binding of Cisplatin-Modified DNA by High Mobility Group 1 Protein," *J. Biol. Chem.*, 276(10):7534-7540 (2001).

Ise, T., et al., "Transcription Factor Y-Box Binding Protein 1 Binds Preferentially to Cisplatin-Modified DNA and Interacts With Proliferating Cell Nuclear Antigen," *Cancer Res.*, 59:342-346 (1999).

Jakobovits, A., et al., "Analysis of Homozygous Mutant Chimeric Mice: Deletion of the Immunoglobulin Heavy-Chain Joining Region Blocks B-Cell Development and Antibody Production," *Proc. Natl. Acad. Sci. USA*, 90:2551-2555 (1993).

Jakobovits, A., et al., "Germ-Line Transmission and Expression of a Human-Derived Yeast Artificial Chromosome," *Nature*, 362:255-258 (1993).

Johns, E.W., et al. "History, Definitions and Problems", in The HMG Chromsomal Problems, (Academic Press), London: Chapter 1, pp. 1-7 (1982).

Jung, F., et al., "Antibodies Against a Peptide Sequence Located in the Linker Region of the HMG-1/2 Box Domains in Sera From Patients With Juvenile Rheumatoid Arthritis," *Arthritis Rheum.*, 40(10):1803-1809 (1997).

Kuby, J., *Immunology*, (New York, W.H. Freeman and Company) p. 1 (1992).

Landsman, D., et al., "A Signature for the HMG-1 Box DNA-Binding Proteins", *BioEssays*, 15(8):539-546 (1993).

Lederman, S., et al., "A Single Amino Acid Substitution in a Common African Allele of the CD4 Molecule Ablates Binding of the Monoclonal Antibody OKT," *Mol. Immunol.*, 28(11):1171-1181 (1991).

Li, et al., "beta-Endorphin Omission Analogs: Dissociation of Immunoreactivity from Other Biological Activities," *Proc. Natl. Acad. Sci.*, 77:3211-3214 (1980).

Lotze, M.T., and K. J. Tracey, "High-Mobility Group Box 1 Protein (HMGB1): Nuclear Weapon in the Immune Arsenal", *Nature Rev. Immunol.* 5:331-342 (2005).

Ma, W., et al. "Detection of Anti-Neutrophil Cytoplasmic Antibodies in MRL/Mp-*Ipr/Ipr* Mice and Analysis of Their Target Antigens," *Autoimmunity*, 32(4):281-291 (2000).

Marks, J. D., et al., "By-Passing Immunization: Building High Affinity Human Antibodies by Chain Shuffling," *Bio/Technology*, 10:779-783 (1992).

Melloni, E., et al., "Extracellular Release of the 'Differentiation Enhancing Factor', a HMG1 Protein Type, is an Early Step in Murine Erythroleukemia Cell Differentiation," *FEBS Lett.*, 368:466-470 (1995).

Melloni, E., et al., "Identity in Molecular Structure Between 'Differentiation Enhancing Factor' of Murine Erithroleukemia Cells and the 30 kD Heparin-Binding Protein of Developing Rat Brain," *Biochem. Biophys. Res. Commun.*, 210(1):82-89 (1995).

Merenmies, J., et al., "30-kDa Heparin-Binding Protein of Brain (Amphoterin) Involved in Neurite Outgrowth," *J. Biol. Chem.*, 266(25):16722-16729 (1991).

Miley, P., et al., "High Affinity Binding and Overlapping Localization of Neurocan and Phosphacan/Protein-Tyrosine Phosphatase—$\zeta/\beta$ with Tenascin-R, Amphoterin, and the Heparin-binding Growth-associated Molecule," *J. Biol. Chem.*, 273(12):6998-7005 (1998).

Mohan, P.S., et al., "Sulfoglycolipids Bind to Adhesive Protein Amphoterin (p30) in the Nervous System," *Biochem. Biophys. Res. Commun.*, 182(2):689-696 (1992).

Ohlin, M., et al., "Human Monoclonal Antibodies Against a Recombinant HIV Envelope Antigen Produced by Primary In Vitro Immunization. Characterization and Epitope Mapping," *Immunology*, 68:325-331 (1989).

Ozaki, S., et al., "Epitope Mapping of Autoantibodies to High Mobility Group (HMG) Proteins HMG1 and HMG2," *Clin. Exp. Immunol.*, 120 (Supp. 1):53 (2000).

Parkinnen, J., et al. "Amphoterin, the 30-kDa Protein in a Family of HMG1-type Polypeptides," *J. Biol. Chem.*, 268(26):19726-19738 (1993).

Parkkinen, J., et al., "Interactions of Plasminogen and Tissue Plasminogen Activator (t-PA) with Amphoterin," *J. Biol. Chem.*, 266(25):16730-16735 (1991).

Passalacqua, M., et al., "Stimulated Astrocytes Release High-Mobility Group 1 Protein, an Inducer of Lan-5 Neuroblastoma Cell Differentiation," *Neuroscience*, 82(4):1021-1028 (1998).

Rauvala, H. and Pihlaskari, R., "Isolation and Some Characteristics of an Adhesive Factor of Brain That Enhances Neurite Outgrowth in Central Neurons," *J. Biol. Chem.*, 262(34): 16625-16635 (1987).

Rauvala, H., et al., "The Adhesive and Neurite-Promoting Molecule p30: Analysis of the Amino-Terminal Sequence and Production of Antipeptide Antibodies That Detect p30 at the Surface of Neuroblastoma Cells and of Brain Neurons," *J. Cell Biol.*, 107(6):2293-2305 (1988).

Redlitz, A., et al., "Receptors for Plasminogen and t-PA: An Update," *Baillière's Clinical Haemtology*, 8(2):313-327 (1995).

Reeves, R., "Molecular Biology of HMGA Proteins: Hubs of Nuclear Function," *Gene: An International Journal on Genes and Genomes*, 277(1-2):63-81 (2001).

Romani, M., et al., "Serological Analysis of Species Specificity in the High Mobility Group Chromosomal Proteins," *J. Biol. Chem.*, 254(8):2918-2922 (1979).

Salmivirta, M., et al., "Neurite Growth-Promoting Protein (Amphoterin, p 30) Binds Syndecan," *Exp. Cell Res.*, 200:444-451 (1992).

Scaffidi, P., et al., "Release of Chromatin Protein HMGB1 by Necrotic Cells Triggers Inflammation," *Nature*, 418:191-95 (2002).

Sjögren-Jansson, E., et al., "Production of Human Monoclonal Antibodies in Dialysis Tubing," *Hybridoma*, 10(3):411-419 (1991).

Sobajima, J., et al. "High Mobility Group (HMG) Non-histone Chromosomal Proteins HMG1 and HMG2 are Significant Target Antigens of Perinuclear Anti-Neutrophil Cytoplasmic Antibodies in Autoimmune Hepatitis," *Gut*, 44:867-873 (1999).

Sobajima, J., et al., "Anti-Neutrophil Cytoplasmic Antibodies (ANCA) in Ulcerative colitis: Anti-Cathepsin G and a Novel Antibody Correlate With a Refractory Type," *Clin. Exp. Immunol.*, 105:120-124 (1996).

Sobajima, J., et al., "Prevalence and Characterization of Perinuclear Anti-Neutrophil Cytoplasmic Antibodies (P-ANCA) Directed Against HMG1 and HMG2 in Ulcerative colitis (UC)," *Clin. Exp. Immunol.*, 111:402-407 (1998).

Sobajima, S., et al., "Novel Autoantigens of Perinuclear Anti-Neutrophil Cytoplasmic Antibodies (P-ANCA) in *Ulcerative colitis*: Non-Histone Chromosomal Proteins, HMG1 and HMG2," *Clin. Exp. Immunol.*, 107:135-140 (1997).

Sparatore, B. et al., "Extracellular High-Mobility Group 1 Protein is Essential for Murine Erythroleukemia Cell Differentiation," *Biochem. J.*, 320(Pt 1):253-256 (1996).

Suda, T., et al., "A Novel Activity of HMG Domains: Promotion of the Triple-Stranded Complex Formation Between DNA Containing $(GGA/TCC)_{11}$ and $d(GGA)_{11}$ Oligonucleotides," *Nucleic Acids Res.*, 24(23):4745-4752 (1996).

Tomita, N., et al., "Direct In Vivo Gene Introduction into Rat Kidney," *Bioch. Biophys. Res. Commun.*, 186(1):129-134 (1992).

Tsuneoka, M., et al., "Monoclonal Antibody Against Non-histone Chromosomal Protein High Mobility Group 1 Co-migrates With High Mobility Group 1 Into the Nucleus," *J. Biol. Chem.*, 261(4):1829-1834 (1986).

Uesugi, H., et al., "Prevalence and Characterization of Novel pANCA, Antibodies to the High Mobility Group Non-Histone Chromosomal Proteins HMG1 and HMG2, in Systemic Rheumatic Diseases," *J. Rheumatol.*, 25(4):703-709 (1998).

Vanderbilt, J.N. and Anderson, J.N., "Monoclonal Antibodies as Probes for the Complexity, Phylogeny, and Chromatin Distribution of High Mobility Group Chromosomal Proteins 1 and 2," *J. Biol. Chem.*, 260(16):9336-9345 (1985).

Vassalli, J.-D., et al., "The Plasminogen Activator/Plasmin System", *J. Clin. Invest.*, 88:1067-1072 (1991).

Wang, H., et al., "HMG-1 as a Late Mediator of Endotoxin Lethality in Mice," *Science*, 285:248-251 (1999).

Wang, H., et al., "Proinflammatory Cytokines (Tumor Necrosis Factor and Interleukin 1) Stimulate Release of High Mobility Group Protein-1 by Pituicytes," *Surgery*, 126:389-392(1999).

Wen, L., et al., "A Human Placental cDNA Clone that Encodes Nonhistone Chromosomal Protein HMG-1," *Nucleic Acids Res.*, 17(3):1197-1213 (1989).

Yamada, S., et al., "High Mobility Group Protein 1 (HMGB1) Quantified by Elisa With a Monoclonal Antibody That Does Not Cross-React With HMGB2, " *Clin. Chem.*, 49(9):1535-1537 (2003).

Yamawaki, M., et al., "Generation and Characterization of Anti-Sulfoglucuronosyl Paragloboside Monoclonal Antibody NGR50 and its Immunoreactivity with Peripheral Nerve," *J. Neurosci. Res.*, 44:586-593 (1996).

Zhang, M. and Tracey, K.J., "Tumor Necrosis Factor", in *The Cytokine Handbook*, (Academic Press Limited), Third Edition, pp. 517-547 (1998).

Human HMGB1 Amino Acid Sequence

MGKGDPKKPKPTGKMSSYAFFVQTCREEHKKKHPDASV
(A box)

NFSEFSKKCSERWKTMSAKEKGKFEDMAKADKARYE

REMKTYIPPKGETKKKFKDPNAPKRLPSAFFLFCSEY
(B box)

RPKIKGEHPGLSIGDVAKKLGEMWNNTAADDKQPYE

KKAAKLKEKYEKDIAAYRAKGKPDAAKKGVVKAEKS

KKKKEEEEDEEEEEEEEEEDDDE        SEQ ID NO:1
(Acidic tail)

FIG. 1

MGKGDPKKPKTGKMSSYAFFVQTCREEHKKKHPDASV
NFSEFSKKCSERWKTMSAKEKGKFEDMAKADKARYER
EMKTYIPPKGET

SEQ ID NO:2

FIG. 2A

FKDPNAPKRLPSAFFLFCSEYRPKIKGEHP
GLSIGDVAKKLGEMWNNTAADDKQPYE
KKAAKLKEKYEKDIAAY

SEQ ID NO:3

FIG. 2B

ATGAAGCGACGATGGAAAAAGAATTTCATAGCCGTCTCAGCAGCCAACCGCT
TTAAGAAAATCTCATCNTCCGGGGCACTTCTGGTTCCGCGTGGATCCATCGAG
GGAAGGATGGGCAAAGGAGATCCTAAGAAGCCGAGAGGCAAAATGTCCTCAT
ATGCATTCTTTGTGCAAACCTGCCGGGAGGAGCACAAGAAGAAGCACCCGGA
TGCTTCTGTCAACTTCTCAGAGTTCTCCAAGAAGTGCTCAGAGAGGTGGAAGA
CCATGTCTGCTAAAGAAAAGGGGAAATTTGAAGATATGGCAAAGGCTGACAA
GGCTCGTTATGAAAGAGAAATGAAAACCTACATCCCCCCCAAAGGGGAGACC
AAAAAGAAGTTCAAGGACCCCAATGCCCCCAAGAGGCCTCCTTCGGCCTTCTT
CTTGTTCTGTTCTGAGTACCGCCCAAAAATCAAAGGCGAGCATCCTGGCTTAT
CCATTGGTGATGTTGCGAAGAAACTAGGAGAGATGTGGAACAACACTGCTGC
GGATGACAAGCAGCCCTATGAAAAGAAGGCCGCCAAGCTGAAGGAGAAGTAT
GAGAAGGATATTGCTGCCTACAGAGCTAAAGGAAAACCTGATGCAGCGAAAA
AGGGGGTGGTCAAGGCTGAGAAGAGCAAGAAAAAGAAGGAAGAGGAAGACG
ACGAGGAGGATGAAGAGGATGAGGAAGAGGAGGAAGAAGAGGAAGATGAAG
ATGAAGAAGAAGATGATGATGATGA (SEQ ID NO:4)

FIG. 3A

MkrrwkknfiavsaanrfkkisssgallvprgsIEGRMGKGDPKKPRGKMSSYAFFVQTCREEHK
KKHPDASVNFSEFSKKCSERWKTMSAKEKGKFEDMAKADKARYEREMKTYIPPK
GETKKKFKDPNAPKRPPSAFFLFCSEYRPKIKGEHPGLSIGDVAKKLGEMWNNTA
ADDKQPYEKKAAKLKEKYEKDIAAYRAKGKPDAAKKGVVKAEKSKKKKEEEDD
EEDEEDEEEEEEEDEDEEEDDDDE (SEQ ID NO:5)

FIG. 3B

GAGGTTCAGCTGCAGCAGTCTGGGGCAGAGCTTGTGAAGCCAGGGGCCTCAG
TCAAGTTGTCCTGCACAGCTTCTGGCTTCAACATTAAAGACACCTATATGCACT
GGGTGAAGCAGAGGCCTGAACAGGGCCTGGAGTGGATTGGAAGGATTGATCC
TGCGAATGGTAATACTAAATATGACCCGAAGTTCCAGGGCAAGGCCACTATAA
CAGCAGACACATCCTCCAACACAGCCTACCTGCAGCTCAGCAGCCTGACATCT
GAGGACACTGCCGTCTATTACTGTGCTAGGGGCGCTTACTGGGGCCAAGGGAC
TCTGGTCACTGTCTCTGCA (SEQ ID NO:6)

FIG. 4A

EVQLQQSGAELVKPGASVKLSCTASGFNIKDTYMHWVKQRPEQGLEWIGRIDPAN
GNTKYDPKFQGKATITADTSSNTAYLQLSSLTSEDTAVYYCARGAYWGQGTLVT
VSA (SEQ ID NO:7)

FIG. 4B

GACATTGTGCTGACCCAATCTCCAGCTTCTTTGGCTGTGTCTCTAGGGCAGAG
GGCCACCATCTCCTGCAAGGCCAGCCAAAGTGTTGATTATGATGGTGATAGTT
ATATGAACTGGTACCAACAGAAACCAGGACAGCCACCCAAACTCCTCATCTAT
GCTGCATCCAATCTAGAATCTGGGATCCCAGCCAGGTTTAGTGGCAGTGGGTC
TGGACAGACTTCACCCTCAACATCCATCCTGTGGAGGAGGAGGATGCTGCAA
CCTATTACTGTCAGCAAAGTAATGAGGATCCATTCACGTTCGGCTCGGGGACA
AAGTTGGAAATAAAA (SEQ ID NO:8)

FIG. 4C

DIVLTQSPASLAVSLGQRATISCKASQSVDYDGDSYMNWYQQKPGQPPKLLIYAA
SNLESGIPARFSGSGSGTDFTLNIHPVEEEDAATYYCQQSNEDPFTFGSGTKLEIK
(SEQ ID NO:9)

FIG. 4D

CAGGTCCAGCTGCAGCAGTCTGGACCTGAGCTGGTGAGGCCTGGGACTTCAGT
GAAGATATCCTGCAAGACTTCTGGCTATACCTTCCTCACCTACTGGATGAACT
GGGTGAAGCAGAGGCCTGGACAGGGCCTTGAGTGGATTGGACAGATTTTTCCT
GCAAGTGATAATACTTACTACAATGAGATGTTCAAGGACAAGGCCACATTGAC
TGTAGACACATCCTCCAGCACAGCCTACATTCATCTCAGCAGCCTGACATCTG
AGGACACTGCTGTCTATTTCTGTGCAAGAGAGGACTCTATGGACTACTGGGGT
CAGGGAACCTCAGTCACCGTCAGCTCA (SEQ ID NO:10)

FIG. 5A

QVQLQQSGPELVRPGTSVKISCKTSGYTFL<u>TYWMN</u>WVKQRPGQGLEWIG<u>QIFPAS
DNTYYNEMFKD</u>KATLTVDTSSSTAYIHLSSLTSEDTAVYFCAR<u>EDSMDY</u>WGQGT
SVTVSS (SEQ ID NO:11)

FIG. 5B

GATATTCAGATGACACAGACTACATCCTCCCTGTCTGCCTCTCTGGGAGACAG
AGTCACCGTCAGTTGCAGTGCAAGTCGGGGCATTAACAATTATTTAAACTGGT
ATCAGCAGAAACCAGATGGAACTGTTAAATTCCTGATCTATTACACATCAAGT
TTACACTCAGGAGTCCCATCAAGGTTCAGTGGCAGTGGGTCTGGGACAGATTA
TTCTCTCACCATCAGCAACCTGGAACCTGAAGATATTGCCACTTACTATTGTCA
GCAGTATAGTAAGCTTCCTTGGACGTTCGGTGGAGGCACCAAGCTGGAATTCA
AA (SEQ ID NO:12)

FIG. 5C

DIQMTQTTSSLSASLGDRVTVSC<u>SASRGINNYLN</u>WYQQKPDGTVKFLIY<u>YTSSLHS</u>
GVPSRFSGSGSGTDYSLTISNLEPEDIATYYC<u>QQYSKLPWT</u>FGGGTKLEFK (SEQ ID
NO:13)

FIG. 5D

GAGGTTCAGCTCCAGCAGTCTGGGACTGTGCTGGCAAGGCCTGGGGCTTCCGT
GAAGATGTCCTGCAAGGCTTCTGGCTACAGCTTTACCAGCTACTGGATGCACT
GGGTAAAACAGAGGCCTGGACAGGGTCTAGAATGGATTGGTGCTATTTATCCT
GGAAATCGTGATGCTAGCTACAATCAGAAGTTCAAGGGCAAGGCCAAACTGA
CTGCAGTCACATCCGCCAGCACTGCCTACTTGGAGCTCAGCAGCCTGACAAAT
GAGGACTCTGCGGTCTATTACTGTACAAGGGACTACGGTAGTTTCTACTTTGA
CTACTGGGGCCAAGGCACCACTCTCACAGTCTCCTCA (SEQ ID NO:14)

FIG. 6A

EVQLQQSGTVLARPGASVKMSCKASGYSFT<u>SYWMH</u>WVKQRPGQGLEWIG<u>AIYP
GNRDASYNQKFKG</u>KAKLTAVTSASTAYLELSSLTNEDSAVYYC<u>TRDYGSFYFDY</u>
WGQGTTLTVSS (SEQ ID NO:15)

FIG. 6B

GATATCCAGATGACACAGACTACATCCTCCCTGTCTGCCTCTCTGGGAGACAG
AGTCACCATCAGTTGCAGGGCAAGTCAGGACATTAGCAATTATTTAAACTGGT
ATCAGCAGAAACCAGATGGAACTGTTAAACTCCTGATCTACTACACATCAAGA
TTACACTCAGGAGTCCCATCAAGGTTCAGTGGCAGTGGGTCTGGAACAGATTA
TTCTCTCACCATTAGCAACCTGGAGCAAGAAGATATTGCCACTTACTTTTGCCA
ACAGGGTAATACGCTTCCGTGGACGTTCGGTGGAGGCACCAAGCTGGAAATC
AAA (SEQ ID NO:16)

FIG. 6C

DIQMTQTTSSLSASLGDRVTISC<u>RASQDISNYLN</u>WYQQKPDGTVKLLIY<u>YTSRLHS</u>
GVPSRFSGSGSGTDYSLTISNLEQEDIATYFC<u>QQGNTLPWT</u>FGGGTKLEIK (SEQ ID
NO:17)

FIG. 6D

| Clone Name | Immunogen | Isotype | Purified Ab Binding Domain | in vivo test |
|---|---|---|---|---|
| 6E6-7-1-1 | rat HMGB1-CBP* | IgG1 | A-Box, Whole HMG | CLP; protective |
| 2E11-1-1-2 | rat HMGB1-CBP | IgG1 | B-Box, Whole HMG | CLP; protective |
| 9G2-7-1-1-1 | rat HMGB1-CBP | IgG1 | | CLP; neg |
| 6H9-1-1-2 | rat HMGB1-CBP | IgG1 | A-Box, Whole HMG | |
| 10D4-1-1-1-2 | rat HMGB1-CBP | IgG2b | A-Box, Whole HMG | |
| 1A9-1-2-1-4 | rat HMGB1-CBP | IgG1 | | |
| 3G8-7-2-1-5 | rat HMGB1-CBP | IgG1 | B-Box, Whole HMG | |
| 3-2G7-1-1-1 | rat HMGB1-CBP | IgG2b | A-Box, Whole HMG | |
| 3-2G5-4-1-2 | rat HMGB1-CBP | IgG1 | A-Box, Whole HMG | |
| 4H11 | rat HMGB1-CBP | IgG1 | A-Box, Whole HMG | |
| 7H3 | rat HMGB1-CBP | IgG1, IgG3 | A-Box, Whole HMG | |
| 3-5A6 | rat HMGB1-CBP | IgG2a, IgG2b | B-Box, Whole HMG | |
| 9G1 | rat HMGB1-CBP | IgG1 | B-Box, Whole HMG | |
| 4C9 | rat HMGB1-CBP | IgG1 | A-Box, Whole HMG | |
| 9H3 | rat HMGB1-CBP | IgG1 | B-Box, Whole HMG | |
| 1C3-1-1-1-1 | B-box | IgG1 | B-Box, Whole HMG | |
| 5C12-1-1-1-1 | B-box | IgG1 | B-Box, Whole HMG | |
| 3E10-5-4-1-1 | B-box | IgG1 | B-Box, Whole HMG | |
| 7G8 | B-box | IgG1 | B-Box, Whole HMG | |
| 4A10-1-3-1-1 | B-box | IgG1 | B-Box, Whole HMG | |

*Appears to bind to CBP region left in small percentage of the HMGB-1 immunogen

FIG. 7

```
  1  mgkgdplkpr gkmssyaffv qtcreehkkk hpdasvnfse fskkcserwk tmsakekgkf   rat   # P07155
  1  mgkgdplkpr gkmssyaffv qtcreehkkk hpdasvnfse fskkcserwk tmsakekgkf   mouse #AAA20508
  1  mgkgdplkpt gkmssyaffv qtcreehkkk hpdasvnfse fskkcserwk tmsakekgkf   human #AAA64970
                                A box 61  ednakadkar yeremktyip pkgetkkkfk dpnapkrpps afflfcseyr pkikgehpgl   rat
 61  ednakadkar yeremktyip pkgetkkkfk dpnapkrpps afflfcseyr pkikgehpgl   mouse
 61  ednakadkar yeremktyip pkgetkkkfk dpnapkrlps afflfcseyr pkikgehpgl   human
                                B box 121  sigdvakklg emwnntaadd kqpyekkaak lkekyekdia ayrakgkpda akkgvvkaek   rat
121  sigdvakklg emwnntaadd kqpyekkaak lkekyekdia ayrakgkpda akkgvvkaek   mouse
121  sigdvakklg emwnntaadd kqpyekkaak lkekyekdia ayrakgkpda akkgvvkaek   human 181  skkkkeeedd eedeedeeee eeeede deee dddde       rat   (SEQ ID NO:18)
181  skkkkeeedd eedeedeeee eeeede deec dddde       mouse (SEQ ID NO:18)
181  skkkkeeeed eedeedeccc edeedeeee dddde         human (SEQ ID NO:1)
```

| Peptide Name | Sequence | Molecular Weight | Calculated Mass to Produce 1mM Stock (in mg per 1 ml) | Amount of Peptide Available (mg) |
|---|---|---|---|---|
| huHMGB1-1-18 | biotin-MGKGDPKKPRGKMSSYAF (SEQ ID NO: 19) | 2,323.83 | 2.32 | 25.4 |
| huHMGB1-16-33 | biotin-YAFFVQTCREEHKKKHPD (SEQ ID NO: 20) | 2,602.04 | 2.60 | 21.6 |
| huHMGB1-28-44 | biotin – KKKHPDASVNFSEFSKK (SEQ ID NO: 21) | 2,315.72 | 2.32 | 23.1 |
| huHMGB1-31-48 | biotin – HPDASVNFSEFSKKCSER (SEQ ID NO: 22) | 2,406.73 | 2.41 | 22.4 |
| huHMGB1-46-63 | biotin – SERWKTMSAKEKGKFEDM (SEQ ID NO: 23) | 2,526.99 | 2.53 | 22.6 |
| huHMGB1-61-78 | biotin – EDMAKADKARYEREMKTY (SEQ ID NO: 24) | 2,574.00 | 2.57 | 22.6 |
| huHMGB1-76-93 | biotin – KTYIPPKGETKKKFKDPN (SEQ ID NO: 25) | 2,457.95 | 2.46 | 23.1 |
| huHMGB1-91-108 | biotin – DPNAPKRPPSAFFLFCSE (SEQ ID NO: 26) | 2,361.78 | 2.36 | 21.4 |
| huHMGB1-106-123 | biotin – CSEYRPKIKGEHPGLSIG (SEQ ID NO: 27) | 2,309.75 | 2.31 | 24.1 |
| huHMGB1-121-138 | biotin – SIGDVAKKLGEMWNNTAA (SEQ ID NO: 28) | 2,243.64 | 2.24 | 25.6 |
| huHMGB1-136-153 | biotin – TAADDKQPYEKKAAKLKE (SEQ ID NO: 29) | 2,372.77 | 2.37 | 22.3 |
| huHMGB1-151-168 | biotin – LKEKYEKDIAAYRAKGKP (SEQ ID NO: 30) | 2,446.94 | 2.45 | 25.5 |
| huHMGB1-166-183 | biotin - GKPDAAKKGVVKAEKSKK (SEQ ID NO: 31) | 2,207.70 | 2.21 | 25.9 |
| huHMGB1-179-185 | biotin – EKSKKKK (SEQ ID NO: 32) | 1,213.54 | 1.21 | 21.7 |
| huHMGB1-181-198 | biotin – SKKKKEEEEDEEDEEDEE (SEQ ID NO: 33) | 2,592.68 | 2.59 | 22.2 |
| huHMGB1-196-215 | biotin – DEEEEEDEEDEDEEEDDDDE (SEQ ID NO: 34) | 2,826.60 | 2.83 | 23.1 |
| huHMGB1-9-85 | PRGKMSSYAFFVQTCREEHKKKHPDASVNFSEFSKKCSERWKTMSAKEKGKFEDMAKADKARYEREMKTYIPPKGET (SEQ ID NO: 35) | 9,070.35 | 9.11 | 18.8 |

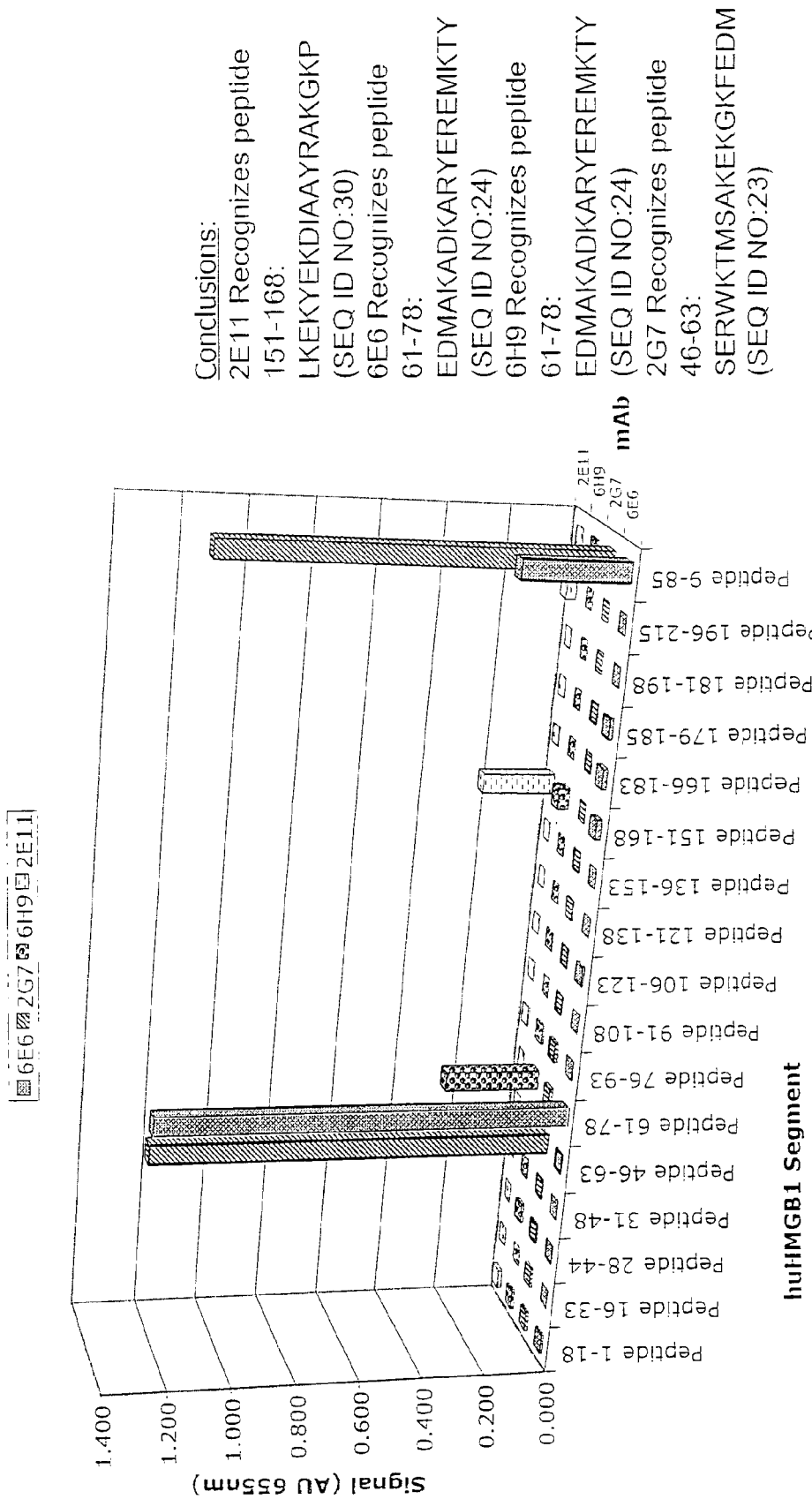

```
CHOHMGB1   ..........................................VNFSEFSKKCSERW
ratHMGB1   MGKGDPKKPRGKMSSYAFFVQTCREEHKKKHPDASVNFSEFSKKCSERW
musHMGB1   MGKGDFKKPRGKMSSYAFFVQTCREEHKKKHPDASVNFSEFSKKCSERW
huHMGB1    MGKGDPKKPRGKMSSYAFFVQTCREEHKKKHPDASVNFSEFSKKCSERW
susHMGB1   MGKGDPKKPRGKMSSYAFFVQTCREEHKKKHPDASVNFSEFSKKCSERW
bosHMGB1   MGKGDPKKPRGKMSSYAFFVQTCREEHKKKHPDASVNFSEFSKKCSERW CHOHMGB1   KTMSAKEKGKFEDMAKADKARYEREMKTYIPPKGETKKKFKDPNAPKRPPSAFFLFCSE
ratHMGB1   KTMSAKEKGKFEDMAKADKARYEREMKTYIPPKGETKKKFKDPNAPKRPPSAFFLFCSE
musHMGB1   KTMSAKEKGKFEDMAKADKARYEREMKTYIPPKGETKKKFKDPNAPKRPPSAFFLFCSE
huHMGB1    KTMSAKEKGKFEDMAKADKARYEREMKTYIPPKGETKKKFKDPNAPKRPPSAFFLFCSE
susHMGB1   KTMSAKEKGKFEDMAKADKARYEREMKTYIPPKGETKKKFKDPNAPKRPPSAFFLFCSE
bosHMGB1   KTMSAKEKGKFEDMAKADKARYEREMKTYIPPKGETKKKFKDPNAPKRPPSAFFLFCSE CHOHMGB1   YRPKIKGEHPGLSIGDVAKKLGEMWNNTAADDKQPYEKKAAKLKEKYEK
ratHMGB1   YRPKIKGEHPGLSIGDVAKKLGEMWNNTAADDKQPYEKKAAKLKEKYEK
musHMGB1   YRPKIKGEHPGLSIGDVAKKLGEMWNNTAADDKQPYEKKAAKLKEKYEK
huHMGB1    YRPKIKGEHPGLSIGDVAKKLGEMWNNTAADDKQPYEKKAAKLKEKYEK
susHMGB1   YRPKIKGEHPGLSIGDVAKKLGEMWNNTAADDKHPYEKKAAKLKEKYEK
bosHMGB1   YRPKIKGEHPGLSIGDVAKKLGEMWNNTAADDKQFYEKKAAKLKEKYEK CHOHMGB1   DIAAYRAKGKPDAAKKGVVKAEKSKKKKEEEDDEEDEEDEEEEEEDEEEEEDEEEDDDE
(SEQ ID NO: 36)
ratHMGB1   DIAAYRAKGKPDAAKKGVVKAEKSKKKKEEEDDEEDEEDEEEEEEEDEEEEEDEEEDDDE
(SEQ ID NO: 18)
musHMGB1   DIAAYRAKGKPDAAKKGVVKAEKSKKKKEEEDDEEDEEDEEEEEEEDEEEEEDEEEDDDE
(SEQ ID NO: 18)
huHMGB1    DIAAYRAKGKPDAAKKGVVKAEKSKKKKEEEDDEEDEEDEEEEEEEDEEEEEDEEEDDDE
(SEQ ID NO: 1)
susHMGB1   DIAAYRAKGKPDAAKKGVVKAEKSKKKKEEEDDEEEDEEDEEEEEEDEEEEEDEEEDDDE
(SEQ ID NO: 37)
bosHMGB1   DIAAYRAKGKPDAAKKGVVKAEKSKKKKEEEDDEEDEEDEEEEEEEDEEEEEDEEEDDDE
(SEQ ID NO: 38)
```

FIG. 17 ccggaattcctcaccATGCACCATCATCACCATCACGGCAAAGGAGATCCTAAGAAGC
CGAGAGGCAAAATGTCATCATATGCATTTTTTGTGCAAACTTGTCGGGAGGAG
CATAAGAAGAAGCACCCAGATGCTTCAGTCAACTTCTCAGAGTTTTCTAAGAA
GTGCTCAGAGAGGTGGAAGACCATGTCTGCTAAAGAGAAAGGAAAATTTGAA
GATATGGCAAAAGCGGACAAGGCCCGTTATGAAAGAGAAATGAAAACCTATA
TCCCTCCCAAAGGGGAGACAAAAAAGAAGTTCAAGGATCCCAATGCACCCAA
GAGGCCTCCTTCGGCCTTCTTCCTCTTCTGCTCTGAGTATCGCCCAAAAATCAA
AGGAGAACATCCTGGCCTGTCCATTGGTGATGTTGCGAAGAAACTGGGAGAG
ATGTGGAATAACACTGCTGCAGATGACAAGCAGCCTTATGAAAAGAAGGCTG
CGAAGCTGAAGGAAAAATACGAAAAGGATATAGCTGCATATCGAGCTAAAGG
AAAGCCTGATGCAGCAAAAAAGGGAGTTGTCAAGGCTGAAAAAAGCAAGAA
AAAGAAGGAAGAGGAGGAAGATGAGGAAGATGAAGAGGATGAGGAGGAGGA
GGAAGATGAAGAAGATGAAGATGAAGAAGAAGATGATGATGATGAAtaatctagag
ca (SEQ ID NO:39)

FIG. 18A

MHHHHHHGKGDPKKPRGKMSSYAFFVQTCREEHKKKHPDASVNFSEFSKKCSER
WKTMSAKEKGKFEDMAKADKARYEREMKTYIPPKGETKKKFKDPNAPKRPPSAF
FLFCSEYRPKIKGEHPGLSIGDVAKKLGEMWNNTAADDKQPYEKKAAKLKEKYE
KDIAAYRAKGKPDAAKKGVVKAEKSKKKKEEEEDEEDEEDEEEEDEEDEDEEE
DDDDE (SEQ ID NO:40)

FIG. 18B

CAGGTTCAGCTGCAGCAGTCTGGGGCTGAGCTGGTGAGGCCTGGGTCCTCAGT
GAAGATTTCCTGCAAGGCTTCTGGCTATGCATTCAGTAGCTACTGGATGAACT
GGGTGAAGCAGAGGCCTGGACAGGGTCTTGAGTGGATTGGACAGATTTATCCT
GGAGATGGTGATACTAACTACAATGGAAAGTTCAAGGGTAAAGCCACACTGA
CTTCAGACAAATCCTCCAGCACAGCCTACATGCAGCTCAGCAGCCTAACATCT
GAGGACTCTGCGGTCTATTTCTGTGCAAGAAGGGAGCCTTATGGTAGCTACGT
GGGGTTTGGTTTCTGGGGCCAAGGGACTCTGGTCACTGTCTCTGCA (SEQ ID
NO:41 )

FIG. 19A

QVQLQQSGAELVRPGSSVKISCKASGYAFS<u>SYWMN</u>WVKQRPGQGLEWIG<u>QIYPG
DGDTNYNGKFKG</u>KATLTSDKSSSTAYMQLSSLTSEDSAVYFCAR<u>REPYGSYVGFG
F</u>WGQGTLVTVSA (SEQ ID NO:42)

FIG. 19B

GAAAATGTTCTCACCCAGTCTCCAGCAATCATGTCTGCATCTCCAGGGGAAAA
GGTCACCATGACCTGCAGTGCCAGTTCAAGTGTAAGTTACATGCACTGGTACC
AGCAAAAGTCAAGCACCTCCCCCAAACTCTGGATTTATGACACATCCAAACTG
GCTTCTGGAGTCCCAGGTCGCTTCAGTGGCAGTGGGTCTGGAAACTCTTACTCT
CTCACGATCAGCAGCATGGAGGCTGAAGATGTTGCCACTTATTACTGTTTTCA
GGGGAGTGGGTACCCACCCACGTTCGGAGGGGGGACCAAGCTGGAAATAAAA
(SEQ ID NO:43)

FIG. 19C

ENVLTQSPAIMSASPGEKVTMTC<u>SASSSVSYMH</u>WYQQKSSTSPKLWIY<u>DTSKLAS</u>
GVPGRFSGSGSGNSYSLTISSMEAEDVATYYC<u>FQGSGYPPT</u>FGGGTKLEIK (SEQ
ID NO:44)

FIG. 19D

| Peptide ID | Sequence | Binds 2G7? |
|---|---|---|
| Human HMGB1-46-63-scr (SEQ ID NO: 45) | RMKEESSAKDGWFTEMKK | NO |
| Human HMGB1-40-57 (SEQ ID NO: 46) | EFSKKCSERWKTMSAKEK | NO |
| Human HMGB1-46-63-B (SEQ ID NO:23) | SERWKTMSAKEKGKFEDM | YES |
| Human HMGB1-53-70 (SEQ ID NO:47) | SAKEKGKFEDMAKADKAR | YES |
| Human HMGB2-46-63-B (SEQ ID NO:48) | SERWKTMSAKEKSKFEDM | NO |

FIG.23 scr = scrambled

| Peptide ID | Sequence | Binds 6E6? |
|---|---|---|
| Human HMGB1-61-78_scr (SEQ ID NO:49) | AKDYMEARKDTEYKMARE | NO |
| Human HMGB1-53-70 (SEQ ID NO:47) | SAKEKGKFEDMAKADKAR<br>‖‖‖‖‖‖‖‖‖ | NO |
| Human HMGB1-61-78-B (SEQ ID NO:24) | B-EDMAKADKARYEREMKTY<br>‖‖‖‖‖‖‖‖‖ | YES |
| Human HMGB1-67-84 (SEQ ID NO:50) | DKARYEREMKTYIPPKGE | YES |

FIG. 24 scr = scrambled

| Peptide ID | Sequence | Binds 2E11? |
|---|---|---|
| Human HMGB1-151-168_scr (SEQ ID NO:51) | KEYREPKYAIKAKKGLDA | NO |
| Human HMGB1-143-160 (SEQ ID NO:52) | PYEKKAAKLKEKYEKDIA | NO |
| Human HMGB1-151-168-B (SEQ ID NO:30) | B-LKEKYEKDIAAYRAKGKP | YES |
| Human HMGB1-157-174 (SEQ ID NO:53) | KDIAAYRAKGKPDAAKKG | NO |

FIG. 25 scr = scrambled

Effect of various concentrations of 2G7 on survival in CLP model

| Dose | 6E6 (dosed qd days 1 & 3) N = 1 expt | Control IgG | 2G7 (dosed qd day 1) N = 2 expts | Control IgG |
|---|---|---|---|---|
| 100 ug/mouse (4 mg/kg) | 73 | 40 | | |
| 10 ug/mouse (0.4 mg/kg) | 82 | | 85.7 | 40 |
| 1 ug/mouse (0.04 mg/kg) | 60 | | 61.9 | |
| 0.1 ug/mouse (0.004 mg/kg) | | | 55 | |

FIG. 29

MGKGDPNKPRGKMSSYAFFVQTCREEHKKKHPDSSVNFAEFSKKCSERWKTMS
AKEKSKFEDMAKSDKARYDREMKNYVPPKGDKKGKKKDPNAPKRPPSAFFLFCS
EHRPKIKSEHPGLSIGDTAKKLGEMWSEQSAKDKQPYEQKAAKLKEKYEKDIAAY
RAKGKSEAGKKGPGRPTGSKKKNEPEDEEEEEEEDEDEEEEDEDEE (SEQ ID
NO:54)

FIG. 30 mgkgdpkkpr gkmssyaffv qtcreehkkk hpdasvnfse fskkcserwk tmsakekgkf
edmakadkar veremktyip pkgetkkkfk dpnapkrpps afflfcseyr pkikgehpgl
sigdvakklg emwnntaadd kqpyekkaak lkekyekdia ayrakgkpda akkgvvkaek
skkkkeeeed eedeedeeee edeededeee dddde (SEQ ID NO:74)

FIG. 31A

A Box:
pr gkmssyaffv qtcreehkkkhpdasvnfse fskkcserwk tmsakekgkf
edmakadkar veremktyip pkget (SEQ ID NO:75)

FIG. 31B

B Box:
fk dpnapkrpps afflfcseyr pkikgehpgl
sigdvakklg emwnntaadd kqpyekkaak lkekyekdia ay(SEQ ID NO:76)

FIG. 31C

All antibodies were used as cultured supernatants.

US 7,632,500 B2

MONOCLONAL ANTIBODIES AGAINST HMGB1

RELATED APPLICATION

This application is a divisional of U.S. application Ser. No. 10/938,992 now U.S. Pat. No. 7,288,250, filed Sep. 10, 2004, which claims the benefit of U.S. Provisional Application No. 60/502,568, filed Sep. 11, 2003.

The entire teachings of the above applications are incorporated herein by reference.

BACKGROUND OF THE INVENTION

Inflammation is often induced by proinflammatory cytokines, such as tumor necrosis factor (TNF), interleukin (IL)-1α, IL-1β, IL-6, macrophage migration inhibitory factor (MIF), and other compounds. These proinflammatory cytokines are produced by several different cell types, most importantly immune cells (for example, monocytes, macrophages and neutrophils), but also non-immune cells such as fibroblasts, osteoblasts, smooth muscle cells, epithelial cells, and neurons. These proinflammatory cytokines contribute to various disorders during the early stages of an inflammatory cytokine cascade.

The early proinflammatory cytokines (e.g., TNF, IL-1, etc.) mediate inflammation, and induce the late release of high mobility group box 1 (HMGB1; also known as HMG-1 and HMG1), a protein that accumulates in serum and mediates delayed lethality and further induction of early proinflammatory cytokines. HMGB1 was first identified as the founding member of a family of DNA-binding proteins, termed high mobility group box (HMGB) proteins, which are critical for DNA structure and stability. It was identified as a ubiquitously expressed nuclear protein that binds double-stranded DNA without sequence specificity. The HMGB1 molecule has three domains: two DNA binding motifs termed HMGB A and HMGB B boxes, and an acidic carboxyl terminus. The two HMGB boxes are highly conserved 80 amino acid, L-shaped domains. HMG boxes are also expressed in other transcription factors including the RNA polymerase I transcription factor human upstream-binding factor and lymphoid-specific factor.

Recent evidence has implicated HMG1 as a cytokine mediator of delayed lethality in endotoxemia (Andersson, U., et al., *J. Exp. Med.* 192(4):565-570 (2000)). That work demonstrated that bacterial endotoxin (lipopolysaccharide (LPS)) activates monocytes/macrophages to release HMG1 as a late response to activation, resulting in elevated serum HMG1 levels that are toxic. Antibodies against HMG1 prevent lethality of endotoxin even when antibody administration is delayed until after the early cytokine response. Like other proinflammatory cytokines, HMG1 is a potent activator of monocytes. Intratracheal application of HMG1 causes acute lung injury, and anti-HMG1 antibodies protect against endotoxin-induced lung edema (Abraham, E., et al., *J. Immunol.* 165:2950-2954 (2000)). Serum HMG1 levels are elevated in critically ill patients with sepsis or hemorrhagic shock, and levels are significantly higher in non-survivors as compared to survivors.

HMG1 has also been implicated as a ligand for RAGE, a multi-ligand receptor of the immunoglobulin superfamily. RAGE is expressed on endothelial cells, smooth muscle cells, monocytes, and nerves, and ligand interaction transduces signals through MAP kinase, P21 ras, and NF-kB. The delayed kinetics of HMG1 appearance during endotoxemia makes it a potentially good therapeutic target, but little is known about the molecular basis of HMG1 signaling and toxicity.

Therefore, given the importance of HMGB proteins in mediating inflammation, it would be useful to identify antibodies that bind HMGB for diagnostic and therapeutic purposes.

SUMMARY OF THE INVENTION

In various embodiments, the present invention is drawn to antibodies or antigen-binding fragments thereof that bind to a vertebrate high mobility group box (HMGB) polypeptide, methods of detecting and/or identifying an agent that binds to an HMGB polypeptide, methods of treating a condition in a subject characterized by activation of an inflammatory cytokine cascade and methods of detecting an HMGB polypeptide in a sample.

In one embodiment, the invention is an antibody or antigen-binding fragment thereof that specifically binds to a vertebrate HMGB A box but does not specifically bind to non-A box epitopes of HMGB, wherein the antibody or antigen-binding fragment inhibits release of a proinflammatory cytokine from a vertebrate cell treated with an HMGB protein.

In certain embodiments, the invention is an antibody produced by murine hybridoma 6E6 HMGB1 mAb, murine hybridoma 6H9 HMGB1 mAb, murine hybridoma 2G7 HMGB1 mAb, murine hybridoma 2E11 HMGB1 mAb, or murine hybridoma 10D4 HMGB1 mAb. In other embodiments, the invention is an antibody or antigen-binding fragment thereof, wherein the binding of the antibody or antigen-binding fragment to a vertebrate HMGB polypeptide can be inhibited by 6E6 HMGB1 mAb, 6H9 HMGB1 mAb, 2G7 HMGB1 mAb, 2E11 HMGB1 mAb and/or 10D4 HMGB1 mAb. In still other embodiments, the invention is an antibody or antigen-binding fragment thereof, wherein the antibody or antigen-binding fragment has the epitopic specificity of 6E6 HMGB1 mAb, 6H9 HMGB1 mAb, 2G7 HMGB1 mAb, 2E11 HMGB1 mAb and/or 10D4 HMGB1 mAb.

In certain embodiments, the invention is an antibody or antigen-binding fragment that binds to a peptide consisting of amino acid residues 46 to 63 of SEQ ID NO:1, amino acid residues 61 to 78 of SEQ ID NO:1 and/or amino acid residues 151 to 168 of SEQ ID NO:1. In one embodiment, the invention is an antibody or antigen-binding fragment, wherein the binding of the antibody or antigen-binding fragment to a peptide consisting of amino acid residues 46 to 63 of SEQ ID NO:1, can be inhibited by 2G7 HMGB1 mAb. In another embodiment, the invention is an antibody or antigen-binding fragment, wherein the binding of the antibody or antigen-binding fragment to a peptide consisting of amino acid residues 61 to 78 of SEQ ID NO:1, can be inhibited by 6E6 HMGB1 mAb and/or 6H9 HMGB1 mAb. In yet another embodiment, the invention is an antibody or antigen-binding fragment, wherein the binding of the antibody or antigen-binding fragment to a peptide consisting of amino acid residues 151 to 168 of SEQ ID NO:1, can be inhibited by 2E11 HMGB1 mAb.

In certain embodiments, the invention is an antibody or antigen-binding fragment that comprises the light chain CDRs (CDR1, CDR2 and CDR3) and the heavy chain CDRs (CDR1, CDR2 and CDR3) of an antibody selected from the group consisting of 6E6 HMGB1 mAb, 6H9 HMGB1 mAb, 2G7 HMGB1 mAb, 10D4 HMGB1 mAb and 2E11 HMGB1 mAb.

In other embodiments, the invention is murine hybridoma 6E6 HMGB1 mAb, murine hybridoma 6H9 HMGB1 mAb, murine hybridoma 2G7 HMGB1 mAb, murine hybridoma 2E11 HMGB1 mAb or murine hybridoma 10D4 HMGB1 mAb.

In another embodiment, the invention is an isolated cell that produces an antibody or antigen-binding fragment that specifically binds to a vertebrate HMGB A box but does not specifically bind to non-A box epitopes of HMGB. In other embodiments, the invention is an isolated cell that produces 6E6 HMGB1 mAb, 6H9 HMGB1 mAb, 2G7 HMGB1 mAb, 2E11 HMGB1 mAb or 10D4 HMGB1 mAb. In still other embodiments, the invention is an isolated cell that produces an antibody or antigen-binding fragment thereof, wherein the binding of the antibody or antigen-binding fragment to a vertebrate HMGB polypeptide can be inhibited by 6E6 HMGB1 mAb, 6H9 HMGB1 mAb, 2G7 HMGB1 mAb, 2E11 HMGB1 mAb and/or 10D4 HMGB1 mAb. In still other embodiments, the invention is an isolated cell that produces an antibody or antigen-binding fragment that has the epitopic specificity of 6E6 HMGB1 mAb, 6H9 HMGB1 mAb, 2G7 HMGB1 mAb, 2E11 HMGB1 mAb and/or 10D4 HMGB1 mAb.

In other embodiments, the invention is a composition that comprises an antibody or antigen-binding fragment of the invention and a pharmaceutically-acceptable excipient.

In another embodiment, the invention is a method of detecting and/or identifying an agent that binds to a vertebrate HMGB polypeptide comprising combining an antibody or antigen-binding fragment of the invention, a test agent and a composition comprising a vertebrate HMGB polypeptide. In the method, the formation of a complex between the antibody or antigen-binding fragment and the HMGB polypeptide is detected or measured and a decrease in complex formation, as compared to a suitable control, indicates that the test agent binds to the HMGB polypeptide.

In another embodiment, the invention is a method of treating a condition in a subject characterized by activation of an inflammatory cytokine cascade comprising administering to the subject an antibody or antigen-binding fragment of the invention.

In certain embodiments, the condition is sepsis, arthritis or lupus.

In another embodiment, the invention is a method of detecting a vertebrate HMGB polypeptide in a sample. In the method, a sample is contacted with an antibody or antigen-binding fragment of the invention, under conditions suitable for binding of the antibody or fragment to HMGB polypeptide present in the sample. If antibody-HMGB complexes or antigen-binding fragment-HMGB complexes are detected, their presence is indicative of HMGB polypeptide in the sample.

In another embodiment, the invention is a test kit for use in detecting the presence of a vertebrate HMGB polypeptide or a portion thereof in a sample. The test kit comprises an antibody or antigen-binding fragment of the invention and one or more ancillary reagents suitable for detecting the presence of a complex between the antibody or antigen-binding fragment and the HMGB polypeptide.

BRIEF DESCRIPTION OF THE DRAWINGS

FIG. 1 is the amino acid sequence of a human (*Homo sapiens*) HMGB1 polypeptide (SEQ ID NO:1). The underlined amino acid residues delineate the A box, B box and acidic tail domains of the HMGB1 polypeptide.

FIG. 2A is the amino acid sequence of a polypeptide comprising an A box of human (*Homo sapiens*) HMGB1 (SEQ ID NO:2). The underlined amino acid residues delineate the A box of the HMGB1 polypeptide, which is the same for human, rat and mouse.

FIG. 2B is the amino acid sequence of a B box of a human (*Homo sapiens*) HMGB1 polypeptide (SEQ ID NO:3). The underlined amino acid residues delineate the B box of the HMGB1 polypeptide, which is the same for human, rat and mouse.

FIG. 3A is the nucleotide sequence encoding the recombinant CBP-Rat HMGB1 peptide (SEQ ID NO:4) that was used as an immunogen to generate monoclonal antibodies.

FIG. 3B is the encoded amino acid sequence of the recombinant CBP-Rat HMGB1 peptide (SEQ ID NO:5) that was used as an immunogen to generate monoclonal antibodies. The CBP affinity tag, which was removed by thrombin cleavage, is indicated in lower case letters and the normal translation initiation amino acid (i.e., M) of HMGB1 is underlined.

FIG. 4A is the nucleotide sequence encoding the $V_H$ domain of 6E6 HMGB1 mAb (SEQ ID NO:6).

FIG. 4B is the encoded amino acid sequence of the $V_H$ domain of 6E6 HMGB1 mAb (SEQ ID NO:7); CDRs are underlined.

FIG. 4C is the nucleotide sequence encoding the $V_K$ domain of 6E6 HMGB1 mAb (SEQ ID NO:8).

FIG. 4D is the encoded amino acid sequence of the $V_K$ domain of 6E6 HMGB1 mAb (SEQ ID NO:9); CDRs are underlined.

FIG. 5A is the nucleotide sequence encoding the $V_H$ domain of 2E11 HMGB1 mAb (SEQ ID NO:10).

FIG. 5B is the encoded amino acid sequence of the $V_H$ domain of 2E11 HMGB1 mAb (SEQ ID NO:11); CDRs are underlined.

FIG. 5C is the nucleotide sequence encoding the $V_K$ domain of 2E11 HMGB1 mAb (SEQ ID NO:12).

FIG. 5D is the encoded amino acid sequence of the $V_K$ domain of 2E11 HMGB1 mAb (SEQ ID NO:13); CDRs are underlined.

FIG. 6A is the nucleotide sequence encoding the $V_H$ domain of 10D4 HMGB1 mAb (SEQ ID NO:14).

FIG. 6B is the encoded amino acid sequence of the $V_H$ domain of 10D4 HMGB1 mAb (SEQ ID NO:15); CDRs are underlined.

FIG. 6C is the nucleotide sequence encoding the $V_K$ domain of 10D4 HMGB1 mAb (SEQ ID NO:16).

FIG. 6D is the encoded amino acid sequence of the $V_K$ domain of 10D4 HMGB1 mAb (SEQ ID NO:17); CDRs are underlined.

FIG. 7 is a table summarizing characteristics of various anti-HMGB1 monoclonal antibodies. Clone names, the immunogen used to generate the monoclonal antibody (either rat HMGB1-CBP (SEQ ID NO:5 (see FIG. 3B) or the B box of a human HMGB1 polypeptide (SEQ ID NO:3 (see FIG. 2B)), the isotype, binding domains for the antibodies and results of in vivo CLP assays are indicated.

FIG. 12 is an amino acid sequence alignment of HMGB1 polypeptide sequences from rat (SEQ ID NO:18; labeled "rat #P07155" or "rat" (GenBank Accession No. P07155)), mouse (*Mus musculus*) (SEQ ID NO:18; labeled "mouse #AAA20508" or "mouse" (GenBank Accession No. AAA20508)) and human (*Homo sapiens*) (SEQ ID NO:1; labeled "human #AAA64970" or "human" (GenBank Accession No. AAA64970)). The A box and B box domains are underlined and labeled as indicated.

FIG. 13A is a table depicting individual peptides corresponding to particular regions of human HMGB1, their respective amino acid sequences, molecular weights, calculated masses required to produce a 1 mM stock solution and available amounts.

FIG. 13B is a histogram depicting the results of HMGB1 peptide binding experiments. Biotinylated peptides corresponding to particular 18 amino acid regions of human HMGB1 and a longer peptide corresponding to amino acid residues 9-85 of human HMGB1 (listed in FIG. 13A) were prepared and analyzed for binding to particular anti-HMGB1 monoclonal antibodies (i.e., 2E11 HMGB1 mAb (2E11), 6E6 HMGB1 mAb (6E6), 6H9 HMGB1 mAb (6H9) and 2G7 HMGB1 mAb (2G7)) by ELISA.

FIG. 17 is a sequence alignment of HMGB1 polypeptide sequences of an HMGB1 polypeptide expressed in CHO cells (CHOHMGB1; SEQ ID NO:36); rat (ratHMGB1; SEQ ID NO:18), mouse (musHMGB1; SEQ ID NO:18), human (huHMGB1; SEQ ID NO:74), pig (susHMGB1; SEQ ID NO:37) and cow (bosHMGB1; SEQ ID NO:38)

FIG. 18A is a nucleotide sequence of a human recombinant HMGB1 polypeptide containing a 5' 6 HIS tag (rec-HMGB1-His$_6$; SEQ ID NO:39). Cloning sequences are indicated in lower case.

FIG. 18B is the encoded amino acid sequence of the human recombinant HMGB1 polypeptide containing a 5' 6 HIS tag (rec-HMGB1-His$_6$; SEQ ID NO:40).

FIG. 19A is the nucleotide sequence encoding the V$_H$ domain of 2G7 HMGB1 mAb (SEQ ID NO:41).

FIG. 19B is the encoded amino acid sequence of the V$_H$ domain of 2G7 HMGB1 mAb (SEQ ID NO:42); CDRs are underlined.

FIG. 19C is the nucleotide sequence encoding the V$_K$ domain of 2G7 HMGB1 mAb (SEQ ID NO:43).

FIG. 19D is the encoded amino acid sequence of the V$_K$ domain of 2G7 HMGB1 mAb (SEQ ID NO:44); CDRs are underlined.

FIG. 23 is a table depicting the results of HMGB1 and HMGB2 peptide binding experiments. Listed in the table are various peptides, their respective amino acid sequences and whether the peptides bind 2G7 HMGB1 mAb. The listed peptides include: a peptide corresponding to amino acid residues 40-57 of human HMGB1 (labeled "Human HMGB1-40-57"), a peptide corresponding to amino acid residues 46-63 of human HMGB1 (labeled "Human HMGB1-46-63-B), a peptide corresponding to amino acid residues 53-70 of human HMGB1 (labeled "Human HMGB1-53-70"), a peptide corresponding to amino acid residues 46-63 of human HMGB2 (labeled "Human HMGB2-46-63-B"), and a peptide consisting of a scrambled amino acid sequence, wherein the amino acid residues that were scrambled were those of amino acid residues 46-63 of human HMGB1 (labeled "Human HMGB1-46-63-scr").

FIG. 24 is a table depicting the results of HMGB1 peptide binding experiments. Listed in the table are various peptides, their respective amino acid sequences and whether the peptides bind 6E6 HMGB1 mAb. The listed peptides include: a peptide corresponding to amino acid residues 53-70 of human HMGB1 (labeled "Human HMGB1-53-70"), a peptide corresponding to amino acid residues 61-78 of human HMGB1 (labeled "Human HMGB1-61-78-B"), a peptide corresponding to amino acid residues 67-84 of human HMGB1 (labeled "Human HMGB1-67-84"), and a peptide consisting of a scrambled amino acid sequence, wherein the amino acid residues that were scrambled were those of amino acid residues 61-78 of human HMGB1 (labeled "Human HMGB1-61-78_scr").

FIG. 25 is a table depicting the results of HMGB1 peptide binding experiments. Listed in the table are various peptides, their respective amino acid sequences and whether the peptides bind 2E11 HMGB1 mAb. The listed peptides include: a peptide corresponding to amino acid residues 143-160 of human HMGB1 (labeled "Human HMGB1-143-160"), a peptide corresponding to amino acid residues 151-168 of human HMGB1 (labeled "Human HMGB1-151-168-B"), a peptide corresponding to amino acid residues 157-174 of human HMGB1 (labeled "Human HMGB1-157-174"), and a peptide consisting of a scrambled amino acid sequence, wherein the amino acid residues that were scrambled were those of amino acid residues 151-168 of human HMGB1 (labeled "Human HMGB1-151-168_scr").

FIG. 29 is a table summarizing CLP survival percentages in mice administered various doses (either 4 mg/kg, 0.4 mg/kg, 0.04 mg/kg or 0.004 mg/kg) of 6E6 HMGB1 mAb (6E6), 2G7 HMGB1 mAb (2G7), or control IgG.

FIG. 30 is the amino acid sequence of a human (*Homo sapiens*) HMGB2 polypeptide (SEQ ID NO:54; GenBank Accession No. M83665).

FIG. 31A is the amino acid sequence of a human (*Homo sapiens*) HMGB1 polypeptide (SEQ ID NO:74).

FIG. 31B is an A box of a human (*Homo sapiens*) HMGB1 polypeptide (SEQ ID NO:75).

FIG. 31C is a B box of a human (*Homo sapiens*) HMGB1 polypeptide (SEQ ID NO:76).

DETAILED DESCRIPTION OF THE INVENTION

Figure 8:
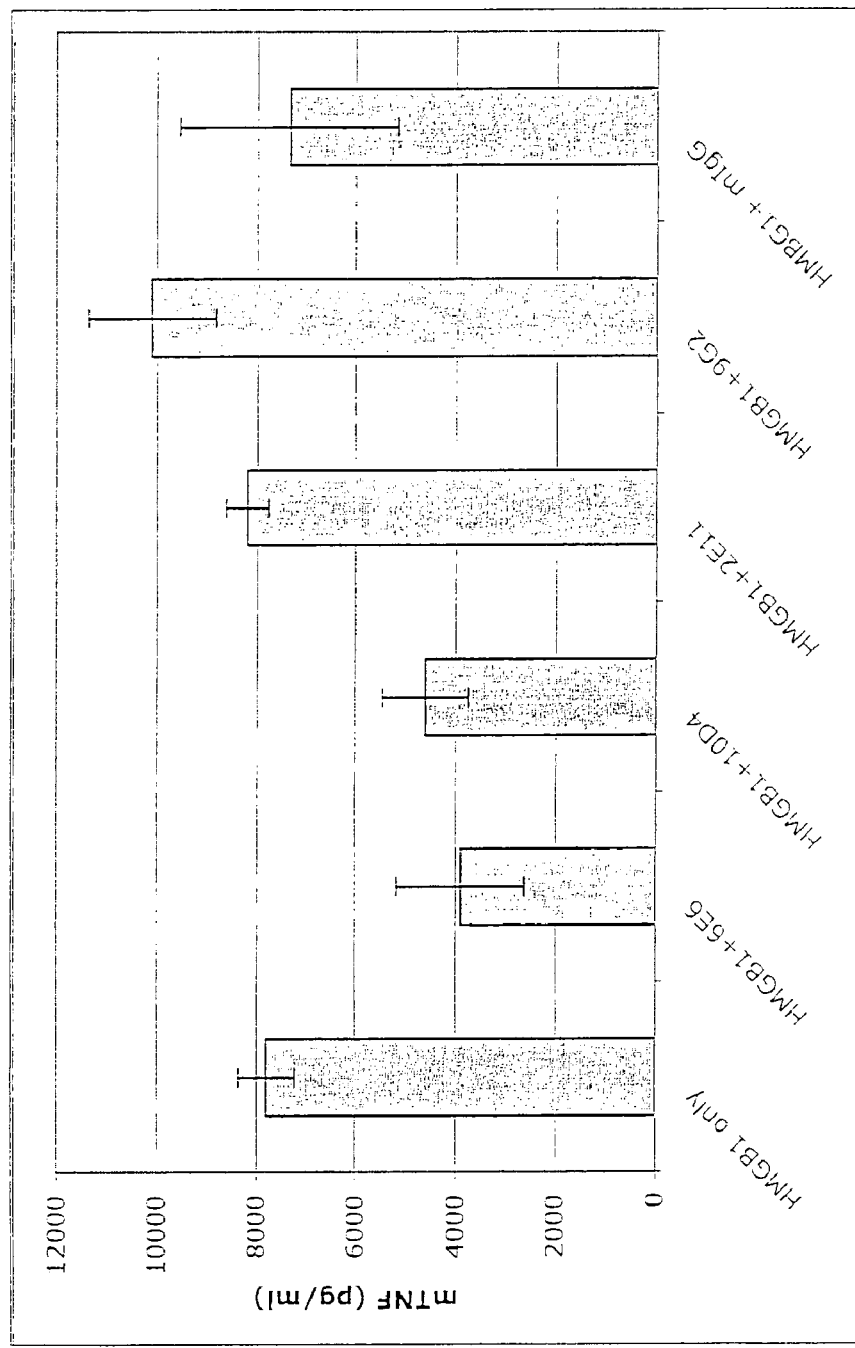
FIG. 8 is a histogram depicting inhibition of TNF release by particular anti-HMGB1 monoclonal antibodies. Mouse TNF was induced by stimulating RAW 264.7 cells with 0.1 µg/ml of recombinant CBP-Rat HMGB1 peptide (SEQ ID NO:5). Where indicated, 20 µg/ml of 6E6 HMGB1 mAb (6E6), 10D4 HMGB1 mAb (10D4), 2E11 HMGB1 mAb (2E11), 9G2 HMGB1 mAb (9G2) or mouse IgG control antibody (mIgG) were added. All samples were done in duplicate and error bars are indicated.

In various embodiments, the present invention is drawn to antibodies or antigen-binding fragments thereof that bind to a vertebrate high mobility group box (HMGB) polypeptide, methods of detecting and/or identifying an agent that binds to an HMGB polypeptide, methods of treating a condition in a subject characterized by activation of an inflammatory cytokine cascade and methods of detecting an HMGB polypeptide in a sample.

Antibodies and Antibody Producing Cells

In one embodiment, the present invention encompasses antibodies or antigen-binding fragments thereof that bind to HMGB polypeptides. The antibodies of the invention can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. In one embodiment, the antibody or antigen-binding fragment is a monoclonal antibody or antigen-binding fragment thereof. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

The term "antibody" as used herein also encompasses functional fragments of antibodies, including fragments of chimeric, humanized, primatized, veneered or single chain antibodies. Functional fragments include antigen-binding fragments of antibodies that bind to an HMGB polypeptide (e.g., a mammalian HMGB polypeptide (e.g. a mammalian HMGB1 polypeptide)). For example, antibody fragments capable of binding to an HMGB polypeptide or a portion thereof, include, but are not limited to Fv, Fab, Fab' and F(ab')$_2$ fragments. Such fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0519596 A1. See also, Newman, R. et al., *BioTechnology,* 10: 1455-1460 (1992), regarding primatized antibody, and Ladner et al., U.S. Pat. No. 4,946,778 and Bird, R. E. et al., *Science,* 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., *Nucl. Acids Res.,* 17: 5404 (1989)); Sato, K., et al., *Cancer Research,* 53: 851-856 (1993); Daugherty, B. L. et al., *Nucleic Acids Res.,* 19(9): 2471-2476 (1991); and Lewis, A. P. and J. S. Crowe, *Gene,* 101: 297-302 (1991)). Using these or other suitable methods, variants can also be readily produced. In one embodiment, cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213).

The antibody can be a humanized antibody comprising one or more immunoglobulin chains (e.g., an antibody comprising a CDR of nonhuman origin (e.g., one or more CDRs derived from an antibody of nonhuman origin) and a framework region derived from a light and/or heavy chain of human origin (e.g., CDR-grafted antibodies with or without framework changes)). In one embodiment, the antibody or antigen-binding fragment thereof comprises the light chain CDRs (CDR1, CDR2 and CDR3) and heavy chain CDRs (CDR1, CDR2 and CDR3) of a particular immunoglobulin. In another embodiment, the antibody or antigen-binding fragment further comprises a human framework region.

The antibodies described herein can also be conjugated to an agent. In one embodiment, the agent is a label, for example, a radioisotope, an epitope label (tag), an affinity label (e.g., biotin, avidin), a spin label, an enzyme, a fluorescent group or a chemiluminescent group. Labeled antibodies or antigen-binding fragments of the present invention can be used, e.g., in the diagnostic and/or prognostic methods described herein. In another embodiment, the antibody is conjugated to a drug, toxin or anti-inflammatory agent. Conjugation of a drug, toxin or anti-inflammatory agent to the anti-HMGB antibodies and antigen-binding fragments of the invention allows for targeting of these agents to sites of HMGB expression and/or activity. Drugs and toxins that can be conjugated to the antibodies of the present invention include, for example, chemotherapeutic agents (e.g., mitomycin C, paxlitaxol, methotrexate, 5-fluorouracil, cisplatin, cyclohexamide), toxins (e.g., ricin, gelonin) and other agents described herein (e.g., the agents described for combination therapy). Anti-inflammatory agents that can be conjugated include, e.g., those described herein.

Antibodies that are specific for an HMGB polypeptide (e.g., a mammalian HMGB polypeptide) can be raised against an appropriate immunogen, such as an isolated and/or recombinant HMGB polypeptide or a portion thereof (including synthetic molecules, such as synthetic peptides). Antibodies can also be raised by immunizing a suitable host (e.g., mouse) with cells that express an HMGB polypeptide, such as GH3 pituicytes, macrophage cells (e.g., RAW 246.7 cells, human macrophage cells), peripheral blood mononuclear cells (PBMCs (e.g., human PBMCs)), primary T cells (e.g., human primary T cells), adrenal cells (e.g., rat adrenal PC-12 cells, human adrenal cells), and kidney cells (e.g., rat primary kidney cells, human primary kidney cells). In addition, cells expressing a recombinant HMGB polypeptide (e.g., a mammalian HMGB polypeptide), such as transfected cells, can be used as an immunogen or in a screen for an antibody that binds thereto (See e.g., Chuntharapai et al., *J. Immunol.,* 152: 1783-1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., *Nature,* 256: 495-497 (1975) and *Eur. J. Immunol.* 6: 511-519 (1976); Milstein et al., *Nature* 266: 550-552 (1977), Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer '94), Ausubel, F. M. et al., Eds., (John Wiley & Sons: New York, N.Y.), Chapter 11, (1991)). Generally, as exemplified herein, a hybridoma is produced by fusing a suitable immortal cell line (e.g., a myeloma cell line such as SP2/0, P3X63Ag8.653 or a heteromyeloma) with antibody-producing cells. Antibody-producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells that produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods that select recombinant antibody from a library (e.g., a phage display library). Transgenic animals capable of producing a repertoire of human antibodies (e.g., XENOMOUSE™ (transgenic mouse, Abgenix, Fremont, Calif.)) can be produced using suitable methods (see e.g., Jakobovits et al., *Proc. Natl. Acad. Sci. USA,* 90: 2551-2555 (1993); Jakobovits et al., *Nature,* 362: 255-258 (1993)). Additional methods that are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

In one embodiment, the antibody or antigen-binding fragment thereof has specificity for an HMGB polypeptide (e.g., a mammalian HMGB polypeptide). In a particular embodiment, the antibody or antigen-binding fragment thereof has specificity for an HMGB1 polypeptide (e.g., a human HMGB1 polypeptide such as depicted in SEQ ID NO:1 and/or SEQ ID NO:74). In another embodiment, the antibody or antigen-binding fragment thereof is an IgG or an antigen-binding fragment of an IgG. In another embodiment, the antibody or antigen-binding fragment thereof is an IgG1 or an antigen-binding fragment of an IgG1. In still other embodiments, the antibody or antigen-binding fragment thereof is an IgG2a, IgG2b, IgG3 antibody, or an antigen-binding fragment of any of the foregoing.

In another embodiment, the antibody or antigen-binding fragment can bind to an HMGB polypeptide and inhibit (reduce or prevent) one or more functions of the HMGB polypeptide. Such HMGB functions include, e.g., increasing inflammation (see, e.g., PCT Publication No. WO 02/092004), increasing release of a proinflammatory cytokine from a cell (see, e.g., PCT Publication No. WO 02/092004), binding to RAGE, binding to TLR2, chemoattraction (see, e.g., Degryse et al., *J. Cell Biol.* 152(6):1197-1206 (2001); the entire teachings of which are incorporated herein by reference), and activation of antigen presenting cells (see, e.g., WO 03/026691; the entire teachings of which are incorporated herein by reference).

In one embodiment, the antibody is a human antibody or an antigen-binding fragment thereof. In another embodiment, the antibody is a humanized antibody or an antigen-binding fragment thereof. In yet another embodiment, the antibody or antigen-binding fragment can inhibit binding of a polypeptide (e.g., RAGE, TLR2) to an HMGB polypeptide and/or inhibit one or more functions mediated by binding of the HMGB polypeptide and the other polypeptide.

In certain embodiments, the antibodies or antigen-binding fragments thereof specifically bind to HMGB epitopes or antigenic determinants (e.g., HMGB epitopes, HMGB A box epitopes, HMGB B box epitopes). As described herein, an antibody or antigen-binding fragment thereof can be screened without undue experimentation for the ability to inhibit release of a proinflammatory cytokine using standard methods. Anti-HMGB A-box antibodies and anti-HMGB B box antibodies that can inhibit the production of a proinflammatory cytokine and/or the release of a proinflammatory cytokine from a cell, and/or inhibit a condition characterized by activation of an inflammatory cytokine cascade, are within the scope of the present invention. In one embodiment, the antibody or antigen-binding fragment of the invention can inhibit the production of TNF, IL-1β, and/or IL-6. In another embodiment, the antibody or antigen-binding fragment of the invention can inhibit the production of TNF (e.g., TNF-α).

As described herein, monoclonal antibodies designated "6E6 HMGB1 mAb", "2E11 HMGB1 mAb", "6H9 HMGB1 mAb", "10D4 HMGB1 mAb" and "2G7 HMGB1 mAb", all of which bind to HMGB1 have been produced. In addition, other monoclonal antibodies designated "9G2 HMGB1 mAb", "1A9 HMGB1 mAb", "3G8 HMGB1 mAb", "2G5 HMGB1 mAb", "4H11 HMGB1 mAb", "7H3 HMGB1 mAb", "3-5A6 HMGB1 mAb", "9G1 HMGB1 mAb", "4C9 HMGB1 mAb", "9H3 HMGB1 mAb", "1C3 HMGB1 mAb", "5C12 HMGB1 mAb", "3E10 HMGB1 mAb", "7G8 HMGB1 mAb" and "4A10 HMGB1 mAb" have been produced. All but 9G2 HMGB1 mAb and 1A9 HMGB1 mAb have been shown to bind HMGB1. 9G2 HMGB1 mAb and 1A9 HMGB1 mAb appear to bind to the CBP region of the immunogen (which is not cleaved in a small percentage of the immunogen).

6E6 HMGB1 mAb, also referred to as 6E6-7-11- or 6E6, can be produced by murine hybridoma 6E6 HMGB1 mAb, which was deposited on Sep. 3, 2003, on behalf of Critical Therapeutics, Inc., 675 Massachusetts Avenue, 14th Floor, Cambridge, Mass. 02139, U.S.A., at the American Type Culture Collection, 10801 University Boulevard, Manassas, Va. 20110, U.S.A., under Accession No. PTA-5433. The invention relates to murine hybridoma 6E6 HMGB1 mAb, to the antibody it produces and to nucleic acids encoding the antibody.

2E11 HMGB1 mAb, also referred to as 2E11-1-1-2 or 2E11, can be produced by murine hybridoma 2E11 HMGB1 mAb, which was deposited on Sep. 3, 2003, on behalf of Critical Therapeutics, Inc., 675 Massachusetts Avenue, 14th Floor, Cambridge, Mass. 02139, U.S.A., at the American Type Culture Collection, 10801 University Boulevard, Manassas, Va. 20110, U.S.A., under Accession No. PTA-5431. The invention relates to murine hybridoma 2E11 HMGB1 mAb, to the antibody it produces and to nucleic acids encoding the antibody.

6H9 HMGB1 mAb, also referred to as 6H9-1-1-2 or 6H9, can be produced by murine hybridoma 6H9 HMGB1 mAb, which was deposited on Sep. 3, 2003, on behalf of Critical Therapeutics, Inc., 675 Massachusetts Avenue, 14th Floor, Cambridge, Mass. 02139, U.S.A., at the American Type Culture Collection, 10801 University Boulevard, Manassas, Va. 20110, U.S.A., under Accession No. PTA-5434. The invention relates to murine hybridoma 6H9 HMGB1 mAb, to the antibody it produces and to nucleic acids encoding the antibody.

10D4 HMGB1 mAb, also referred to as 10D4-1-1-1-2 or 10D4, can be produced by murine hybridoma 10D4 HMGB1 mAb, which was deposited on Sep. 3, 2003, on behalf of Critical Therapeutics, Inc., 675 Massachusetts Avenue, 14th Floor, Cambridge, Mass. 02139, U.S.A., at the American Type Culture Collection, 10801 University Boulevard, Manassas, Va. 20110, U.S.A., under Accession No. PTA-5435. The invention relates to murine hybridoma 10D4 HMGB1 mAb, to the antibody it produces and to nucleic acids encoding the antibody.

2G7 HMGB1 mAb, also referred to as 3-2G7-1-1-1 or 2G7, can be produced by murine hybridoma 2G7 HMGB1 mAb, which was deposited on Sep. 3, 2003, on behalf of Critical Therapeutics, Inc., 675 Massachusetts Avenue, 14th Floor, Cambridge, Mass. 02139, U.S.A., at the American Type Culture Collection, 10801 University Boulevard, Manassas, Va. 20110, U.S.A., under Accession No. PTA-5432. The invention relates to murine hybridoma 2G7 HMGB1 mAb, to the antibody it produces and to nucleic acids encoding the antibody.

For cultivation of the above identified murine hybridomas (e.g., 6E6 HMGB1 mAb, 6H9 HMGB1 mAb, 2G7 HMGB1 mAb, 10D4 HMGB1 mAb, 2G7 HMGB1 mAb), DMEM, 10% FCS, 1% IL-6, 1% L-glutamine and 1% Pen-Strep should be added.

9G2 HMGB1 mAb, also referred to as 9G2-7-1-1-1 or 9G2, can be produced by murine hybridoma 9G2 HMGB1 mAb. The invention relates to murine hybridoma 9G2 HMGB1 mAb, to the antibody it produces, and to nucleic acids encoding the antibody.

1A9 HMGB1 mAb, also referred to as 1A9-1-2-1-4 or 1A9, can be produced by murine hybridoma 1A9 HMGB1 mAb. The invention relates to murine hybridoma 1A9 HMGB1 mAb, to the antibody it produces, and to nucleic acids encoding the antibody.

3G8 HMGB1 mAb, also referred to as 3G8-7-2-1-5 or 3G8, can be produced by murine hybridoma 3G8 HMGB1 mAb. The invention relates to murine hybridoma 3G8 HMGB1 mAb, to the antibody it produces, and to nucleic acids encoding the antibody.

2G5 HMGB1 mAb, also referred to as 3-2G5-4-1-2 or 2G5, can be produced by murine hybridoma 2G5 HMGB1 mAb. The invention relates to murine hybridoma 2G5 HMGB1 mAb, to the antibody it produces, and to nucleic acids encoding the antibody.

4H11 HMGB1 mAb, also referred to as 4H11, can be produced by murine hybridoma 4H11 HMGB mAb. The invention relates to murine hybridoma 4H11 HMGB1 mAb, to the antibody it produces, and to nucleic acids encoding the antibody.

7H3 HMGB1 mAb, also referred to as 7H3, can be produced by murine hybridoma 7H3 HMGB1 mAb. The invention relates to murine hybridoma 7H3 HMGB1 mAb, to the antibody it produces, and to nucleic acids encoding the antibody.

3-5A6 HMGB1 mAb, also referred to as 3-5A6 or 5A6, can be produced by murine hybridoma 3-5A6 HMGB1 mAb. The invention relates to murine hybridoma 3-5A6 HMGB1 mAb, to the antibody it produces, and to nucleic acids encoding the antibody.

9G1 HMGB1 mAb, also referred to as 9G1, can be produced by murine hybridoma 9G1 HMGB1 mAb. The invention relates to murine hybridoma 9G1 HMGB1 mAb, to the antibody it produces, and to nucleic acids encoding the antibody.

4C9 HMGB1 mAb, also referred to as 4C9, can be produced by murine hybridoma 4C9 HMGB1 mAb. The invention relates to murine hybridoma 4C9 HMGB1 mAb, to the antibody it produces, and to nucleic acids encoding the antibody. 9H3 HMGB1 mAb, also referred to as 9H3, can be produced by murine hybridoma 9H3 HMGB1 mAb. The invention relates to murine hybridoma 9H3 HMGB1 mAb, to the antibody it produces, and to nucleic acids encoding the antibody.

1C3 HMGB1 mAb, also referred to as 1C3-1-1-1-1 or 1C3, can be produced by murine hybridoma 1C3 HMGB1 mAb. The invention relates to murine hybridoma 1C3 HMGB1 mAb, to the antibody it produces, and to nucleic acids encoding the antibody.

5C12 HMGB1 mAb, also referred to as 5C12-1-1-1-1 or 5C12, can be produced by murine hybridoma 5C12 HMGB1 mAb. The invention relates to murine hybridoma 5C12 HMGB1 mAb, to the antibody it produces, and to nucleic acids encoding the antibody.

3E10 HMGB1 mAb, also referred to as 3E10-5-4-1-1 or 3E10, can be produced by murine hybridoma 3E10 HMGB1 mAb. The invention relates to murine hybridoma 3E10 HMGB1 mAb, to the antibody it produces, and to nucleic acids encoding the antibody.

7G8 HMGB1 mAb, also referred to as 7G8, can be produced by murine hybridoma 7G8 HMGB1 mAb. The invention relates to murine hybridoma 7G8 HMGB1 mAb, to the antibody it produces, and to nucleic acids encoding the antibody.

4A10 HMGB1 mAb, also referred to as 4A10-1-3-1-1 or 4A10, can be produced by murine hybridoma 4A10 HMGB1 mAb. The invention relates to murine hybridoma 4A10 HMGB1 mAb, to the antibody it produces, and to nucleic acids encoding the antibody.

In one embodiment, the antibody or antigen-binding fragment thereof is selected from the group consisting of 6E6 HMGB1 mAb, 6H9 HMGB1 mAb, 2G7 HMGB1 mAb, 10D4 HMGB1 mAb, 2E11 HMGB1 mAb and an antigen-binding fragment of any of the foregoing.

In another embodiment, the antibody or antigen-binding fragment has the same or similar epitopic specificity of an antibody or antigen-binding fragment selected from the group consisting of 6E6 HMGB1 mAb, 6H9 HMGB1 mAb, 2G7 HMGB1 mAb, 10D4 HMGB1 mAb, 2E11 HMGB1 mAb and/or an antigen-binding fragment of any of the foregoing. Antibodies or antigen-binding fragments with an epitopic specificity that is the same as, or similar to, that of 6E6 HMGB1 mAb, 6H9 HMGB1 mAb, 2G7 HMGB1 mAb, 10D4 HMGB1 mAb and/or 2E11 HMGB1 mAb can be identified by a variety of suitable methods. For example, an antibody with the same or similar epitopic specificity as, e.g., 6E6 HMGB1 mAb, can be identified based upon the ability to compete with 6E6 HMGB1 mAb for binding to a HMGB polypeptide (e.g., a mammalian HMGB polypeptide (e.g., a mammalian HMGB1 polypeptide)). In another example, the binding of, e.g., 6E6 HMGB1 mAb, and the binding of an antibody with the same or similar epitopic specificity for a HMGB polypeptide can be inhibited by a single peptide (e.g., a natural peptide, a synthetic peptide). In various embodiments, the peptide can comprise, e.g., 9 to about 50 amino acids, 9 to about 40 amino acids, 9 to about 30 amino acids, 9 to about 25 amino acids or 9 to about 20 amino acids.

As exemplified herein, 18 amino acid peptides corresponding to particular regions of the human HMGB1 polypeptide were shown to bind to various HMGB1 monoclonal antibodies. The studies described herein mapped epitopes within HMGB1 that bind to particular HMGB1 antibodies.

For example, 2E11 HMGB1 mAb was shown to bind a peptide corresponding to amino acids 151-168 of human HMGB1 (amino acid residues 151-168 of SEQ ID NO:1; i.e., LKEKYEKDIAAYRAKGKP (SEQ ID NO:30)). Additional studies suggest that 2E11 HMGB1 mAb recognizes an epitope that is present within amino acid residues 156-161, 155-161, 155-162, 156-162 and/or 156-163, of HMGB1 (see Example 14).

6E6 HMGB1 mAb and 6H9 HMGB1 mAb were shown to bind to a peptide corresponding to amino acids 61-78 of human HMGB1 (amino acid residues 61-78 of SEQ ID NO:1; i.e., EDMAKADKARYEREMKTY (SEQ ID NO:24)). Additional studies demonstrated that 6E6 HMGB1 mAb recognizes an epitope that is present within amino acid residues 67-78 of HMGB1 (see Example 13).

2G7 HMGB1 mAb was shown to bind a peptide corresponding to amino acids 46-63 of human HMGB1 (amino acid residues 46-63 of SEQ ID NO:1; i.e., SERWKTMSAKEKGKFEDM (SEQ ID NO:23)) (see Example 10). Further studies demonstrated that 2G7 HMGB1 mAb recognizes an epitope that is present within amino acid residues 53-63 of HMGB1 (see Example 12). In addition, 2G7 HMGB1 mAb does not bind to amino acid residues 46-63 of HMGB2 (SEQ ID NO:48), notwithstanding only a single amino acid difference between the HMGB1 46-63 peptide and the HMGB2 46-63 peptide (see Example 12). Thus, in one embodiment, the antibodies or antigen-binding fragments of the invention bind to HMGB1 but not to HMGB2. In other embodiments, the antibodies or antigen-binding fragments of the invention bind to both HMGB1 and HMGB2.

These 18 amino acid peptides, or other peptides corresponding to particular regions of HMGB1, could be used in epitopic studies to determine if an antibody or antigen-binding fragment inhibited binding of the peptide to an antibody known to bind that peptide (e.g., 6E6 HMGB1 mAb, 6H9 HMGB1 mAb, 2G7 HMGB1 mAb, 10D4 HMGB1 mAb, 2E11 HMGB1 mAb, others antibodies described herein). Thus, for example, an antibody or antigen-binding fragment to be tested for its epitopic specificity could be assayed with, e.g., 2E11 HMGB1 mAb and a peptide corresponding to amino acids 151-168 of human HMGB1 (which 2E11 HMGB1 mAb is known to bind).

In another example, an antibody with the same or similar epitopic specificity as an antibody of the invention (e.g., 6E6 HMGB1 mAb, 6H9 HMGB1 mAb, 2G7 HMGB1 mAb, 10D4 HMGB1 mAb and/or 2E11 HMGB1 mAb) can be identified using a chimeric HMGB polypeptide (see e.g., Banks, G. C., et al., *J. Biol. Chem.* 274(23):16536-16544 (1999)).

In one embodiment, the antibody or antigen-binding fragment can compete with 6E6 HMGB1 mAb, 6H9 HMGB1 mAb, 2G7 HMGB1 mAb, 10D4 HMGB1 mAb, 2E11

HMGB1 mAb and/or an antigen-binding fragment of any of the foregoing, for binding to an HMGB polypeptide (e.g., a mammalian HMGB polypeptide (e.g., a mammalian HMGB1 polypeptide)). Such inhibition of binding can be the result of competition for the same or similar epitope or steric interference (e.g., where antibodies bind overlapping epitopes or adjacent epitopes). Inhibition by 6E6 HMGB1 mAb, 6H9 HMGB1 mAb, 2G7 HMGB1 mAb, 10D4 HMGB1 mAb, 2E11 HMGB1 mAb, and/or an antigen-binding fragment of any of the foregoing, can also be due to a change in the conformation of the HMGB polypeptide that is induced upon antibody binding to the HMGB polypeptide.

In another embodiment, the antibody or antigen-binding fragment thereof is selected from the group consisting of 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, 4A10 HMGB1 mAb, and an antigen-binding fragment of any of the foregoing.

In one embodiment, the antibody or antigen-binding fragment has the epitopic specificity of an antibody or antigen-binding fragment selected from the group consisting of 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, 4A10 HMGB1 mAb, and an antigen-binding fragment of any of the foregoing. As described above, antibodies or antigen-binding fragments with an epitopic specificity that is the same as, or similar to, one or more of these antibodies or antigen-binding fragments can be identified by a variety of suitable methods (e.g., using methods described herein and/or known in the art).

In another embodiment, the antibody or antigen-binding fragment can compete with 3G8 HMGB1 mAb, 2G5 HMGB1 mAb, 4H11 HMGB1 mAb, 7H3 HMGB1 mAb, 3-5A6 HMGB1 mAb, 9G1 HMGB1 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb, 4A10 HMGB1 mAb, and/or an antigen-binding fragment of any of the foregoing, for binding to an HMGB polypeptide (e.g., a mammalian HMGB polypeptide). As described above, inhibition of binding can be the result of competition for the same or similar epitope or steric interference (e.g., where antibodies bind overlapping epitopes or adjacent epitopes). Inhibition can also be due to a change in the conformation of the HMGB polypeptide that is induced upon binding of the antibody or antigen-binding fragment to the HMGB polypeptide.

In one embodiment, the antibody or antigen-binding fragment thereof comprises the six CDRs (light chain CDRs (CDR1, CDR2 and CDR3) and heavy chain CDRs (CDR1, CDR2 and CDR3)) of an antibody selected from the group consisting of 6E6 HMGB1 mAb, 6H9 HMGB1 mAb, 2G7 HMGB1 mAb, 10D4 HMGB1 mAb and 2E11 HMGB1 mAb. In another embodiment, the antibody is a humanized antibody that comprises the light chain CDRs (CDR1, CDR2 and CDR3) and heavy chain CDRs (CDR1, CDR2 and CDR3) of an antibody selected from the group consisting of 6E6 HMGB1 mAb, 6H9 HMGB1 mAb, 2G7 HMGB1 mAb, 10D4 HMGB1 mAb and 2E11 HMGB1 mAb. In other embodiments, the antibody or antigen-binding fragment thereof comprises the six CDRs (light chain CDRs (CDR1, CDR2 and CDR3) and heavy chain CDRs (CDR1, CDR2 and CDR3)) of any other antibody described herein.

In another embodiment, the antibody or antigen-binding fragment thereof comprises from one to six of the light chain and heavy chain CDRs of an antibody of the invention (e.g., 6E6 HMGB1 mAb, 6H9 HMGB1 mAb, 2G7 HMGB1 mAb, 10D4 HMGB1 mAb, 2E11 HMGB1 mAb). For example, the antibody or antigen-binding fragment can comprise one, two, three, four, five or six, of the light chain and heavy chain CDRs. In another embodiment, the antibody or antigen-binding fragment thereof comprises at least one light chain CDR or heavy chain CDR from one antibody of the invention and at least one light chain CDR or heavy chain CDR from a different antibody of the invention (e.g., 6E6 HMGB1 mAb, 6H9 HMGB1 mAb, 2G7 HMGB1 mAb, 10D4 HMGB1 mAb, 2E11 HMGB1 mAb). For example, an antibody or antigen-binding fragment could comprise one or more CDRs from 6E6 HMGB1 mAb and one or more CDRs from 6H9 HMGB1 mAb. Antibodies and antigen-binding fragments combining other combinations of CDRs from different antibodies of the invention are also encompassed.

In another embodiment, the antibody or antigen-binding fragment thereof comprises the six CDRs (light chain CDRs (CDR1, CDR2 and CDR3) and heavy chain CDRs (CDR1, CDR2 and CDR3)) of an antibody selected from the group consisting of 3G8 HMGB1 mAb, 2G5 HMGB1 mAb, 4H11 HMGB1 mAb, 7H3 HMGB1 mAb, 3-5A6 HMGB1 mAb, 9G1 HMGB11 mAb, 4C9 HMGB1 mAb, 9H3 HMGB1 mAb, 1C3 HMGB1 mAb, 5C12 HMGB1 mAb, 3E10 HMGB1 mAb, 7G8 HMGB1 mAb and 4A 10 HMGB1 mAb. In another embodiment, the antibody or antigen-binding fragment thereof comprises from one to six of the light chain and heavy chain CDRs of one of these antibodies.

In certain embodiments, the antibody or antigen-binding fragment comprises one or more CDRs that are at least 80% identical, at least 90% identical, or at least 95% identical, to a CDR of an antibody of the invention (e.g., 6E6 HMGB1 mAb, 6H9 HMGB1 mAb, 2G7 HMGB1 mAb, 10D4 HMGB1 mAb, 2E11 HMGB1 mAb). In other embodiments, the antibody or antigen-binding fragment comprises one or more CDRs that are at least 80% similar, at least 90% similar, or at least 95% similar, to a CDR of an antibody of the invention. Methods for determining sequence identity and similarity of two polypeptides are described herein and/or are well known in the art.

The invention also relates to a bispecific antibody, or functional fragment thereof (e.g., F(ab')$_2$), which binds to an HMGB polypeptide and at least one other antigen (e.g., tumor antigen, viral antigen). In a particular embodiment, the bispecific antibody, or functional fragment thereof, has the same or similar epitopic specificity as 6E6 HMGB1 mAb, 6H9 HMGB1 mAb, 2G7 HMGB1 mAb, 10D4 HMGB1 mAb and/or 2E11 HMGB1 mAb, and at least one other antibody. Bispecific antibodies can be secreted by triomas and hybrid hybridomas. Generally, triomas are formed by fusion of a hybridoma and a lymphocyte (e.g., antibody-secreting B cell) and hybrid hybridomas are formed by fusion of two hybridomas. Each of the fused cells (i.e., hybridomas, lymphocytes) produces a monospecific antibody. However, triomas and hybrid hybridomas can produce an antibody containing antigen-binding sites that recognize different antigens. The supernatants of triomas and hybrid hybridomas can be assayed for bispecific antibody using a suitable assay (e.g., ELISA), and bispecific antibodies can be purified using conventional methods. (see, e.g., U.S. Pat. No. 5,959,084 (Ring et al.), U.S. Pat. No. 5,141,736 (Iwasa et al.), U.S. Pat. Nos. 4,444,878, 5,292,668, 5,523,210 (all to Paulus et al.) and U.S. Pat. No. 5,496,549 (Yamazaki et al.)).

In one embodiment, the invention relates to an isolated cell that produces an antibody or an antigen-binding fragment of the invention. In a particular embodiment, the isolated antibody-producing cell of the invention is an immortalized cell, such as a hybridoma, heterohybridoma, lymphoblastoid cell or a recombinant cell. The antibody-producing cells of the present invention have uses other than for the production of antibodies. For example, the cell of the present invention can be fused with other cells (such as suitably drug-marked human myeloma, mouse myeloma, human-mouse heteromyeloma or human lymphoblastoid cells) to produce, for example, additional hybridomas, and thus provide for the transfer of the genes encoding the antibody. In addition, the cell can be used as a source of nucleic acids encoding the anti-HMGB immunoglobulin chains, which can be isolated and expressed (e.g., upon transfer to other cells using any suitable technique (see e.g., Cabilly et al., U.S. Pat. No. 4,816,567, Winter, U.S. Pat. No. 5,225,539)). For instance, clones comprising a sequence encoding a rearranged anti-HMGB light and/or heavy chain can be isolated (e.g., by PCR). In addition, cDNA libraries can be prepared from mRNA isolated from an appropriate cell line, and cDNA clones encoding an anti-HMGB immunoglobulin chain(s) can be isolated. Thus, nucleic acids encoding the heavy and/or light chains of the antibodies, or portions thereof, can be obtained and used for the production of the specific immunoglobulin, immunoglobulin chain, or variants thereof (e.g., humanized immunoglobulins) in a variety of host cells or in an in vitro translation system. For example, the nucleic acids, including cDNAs, or derivatives thereof encoding variants such as a humanized immunoglobulin or immunoglobulin chain, can be placed into suitable prokaryotic or eukaryotic vectors (e.g., expression vectors) and introduced into a suitable host cell by an appropriate method (e.g., transformation, transfection, electroporation, infection), such that the nucleic acid is operably linked to one or more expression control elements (e.g., in the vector or integrated into the host cell genome), to produce a recombinant antibody-producing cell. Thus, in certain embodiments, the invention is a nucleic acid that encodes an antibody or antigen-binding fragment of the invention. In other embodiments, the invention is a vector that comprises a nucleic acid encoding an antibody or antigen-binding fragment of the invention.

HMGB Polypeptides, HMGB A Boxes and HMGB B Boxes

As described, in one embodiment the invention is an antibody or antigen-binding fragment thereof that binds to an HMGB polypeptide.

As used herein, an "HMGB polypeptide" is a polypeptide that has at least 60%, more preferably, at least 70%, 75%, 80%, 85%, or 90%, and most preferably at least 95% sequence identity, to a sequence selected from the group consisting of SEQ ID NO:1, SEQ ID NO:18 and SEQ ID NO:74 (as determined, for example, using the BLAST program and parameters described herein). In one embodiment, the HMGB polypeptide increases inflammation and/or increases release of a proinflammatory cytokine from a cell. In another embodiment, the HMGB polypeptide has one of the above biological activities. Typically, the HMGB polypeptide has both of the above biological activities.

The term "polypeptide" refers to a polymer of amino acids, and not to a specific length; thus, peptides, oligopeptides and proteins are included within the definition of a polypeptide. In one embodiment, the HMGB polypeptide is a mammalian HMGB polypeptide, for example, a mammalian HMGB polypeptide (e.g., a human HMGB1 polypeptide). In another embodiment, the HMGB polypeptide contains a B box DNA binding domain and/or an A box DNA binding domain and/or an acidic carboxyl terminus as described herein.

Other examples of HMGB polypeptides are described in GenBank Accession Numbers AAA64970, AAB08987, P07155, AAA20508, S29857, P09429, NP_002119, CAA31110, S02826, U00431, X67668, NP_005333, NM_016957, and J04179, the entire teachings of which are incorporated herein by reference. Additional examples of HMGB polypeptides include, but are not limited to mammalian HMG1 ((HMGB1) as described, for example, in GenBank Accession Number U51677), HMG2 ((HMGB2) as described, for example, in GenBank Accession Number M83665), HMG-2A ((HMGB3, HMG-4) as described, for example, in GenBank Accession Numbers NM_005342 and NP_005333), HMG14 (as described, for example, in GenBank Accession Number P05114), HMG17 (as described, for example, in GenBank Accession Number X13546), HMGI (as described, for example, in GenBank Accession Number L17131), and HMGY (as described, for example, in GenBank Accession Number M23618); nonmammalian HMG T1 (as described, for example, in GenBank Accession Number X02666) and HMG T2 (as described, for example, in GenBank Accession Number L32859) (rainbow trout); HMG-X (as described, for example, in GenBank Accession Number D30765) (Xenopus); HMG D (as described, for example, in GenBank Accession Number X71138) and HMG Z (as described, for example, in GenBank Accession Number X71139) (Drosophila); NHP10 protein (HMG protein homolog NHP 1) (as described, for example, in GenBank Accession Number Z48008) (yeast); non-histone chromosomal protein (as described, for example, in GenBank Accession Number O00479) (yeast); HMG 1/2 like protein (as described, for example, in GenBank Accession Number Z11540) (wheat, maize, soybean); upstream binding factor (UBF-1) (as described, for example, in GenBank Accession Number X53390); PMS1 protein homolog 1 (as described, for example, in GenBank Accession Number U13695); single-strand recognition protein (SSRP, structure-specific recognition protein) (as described, for example, in GenBank Accession Number M86737); the HMG homolog TDP-1 (as described, for example, in GenBank Accession Number M74017); mammalian sex-determining region Y protein (SRY, testis-determining factor) (as described, for example, in GenBank Accession Number X53772); fungal proteins: mat-1 (as described, for example, in GenBank Accession Number AB009451), ste 11 (as described, for example, in GenBank Accession Number X53431) and Mc 1; SOX 14 (as described, for example, in GenBank Accession Number AF107043) (as well as SOX 1 (as described, for example, in GenBank Accession Number Y13436), SOX 2 (as described, for example, in GenBank Accession Number Z31560), SOX 3 (as described, for example, in GenBank Accession Number X71135), SOX 6 (as described, for example, in GenBank Accession Number AF309034), SOX 8 (as described, for example, in GenBank Accession Number AF226675), SOX 10 (as described, for example, in GenBank Accession Number AJ001183), SOX 12 (as described, for example, in GenBank Accession Number X73039) and SOX 21 (as described, for example, in GenBank Accession Number AF107044)); lymphoid specific factor (LEF-1) (as described, for example, in GenBank Accession Number X58636); T-cell specific transcription factor (TCF-1) (as described, for example, in GenBank Accession Number X59869); MTT1 (as described, for example, in GenBank Accession Number M62810); and SP100-HMG nuclear autoantigen (as described, for example, in GenBank Accession Number U36501).

Other examples of HMGB proteins are polypeptides encoded by HMGB nucleic acid sequences having GenBank Accession Numbers NG_000897 (HMG1L10) (and in particular by nucleotides 658-1305 of NG_000897); AF076674 (HMG1L1) (and in particular by nucleotides 1-633 of AF076674; AF076676 (HMG1L4) (and in particular by nucleotides 1-564 of AF076676); AC010149 (HMG sequence from BAC clone RP11-395A23) (and in particular by nucleotides 75503-76117 of AC010149); AF165168 (HMG1 L9) (and in particular by nucleotides 729-968 of AF165168); XM_063129 (LOC122441) (and in particular by nucleotides 319-558 of XM_063129); XM_066789 (LOC139603) (and in particular by nucleotides 1-258 of XM_066789); and AF165167 (HMG1L8) (and in particular by nucleotides 456-666 of AF165167).

The antibodies and antigen-binding fragments of the invention bind to an HMGB polypeptide (e.g., one or more of the HMGB polypeptides listed above). In one embodiment, the antibody or antigen-binding fragment thereof binds to a vertebrate HMGB polypeptide. In another embodiment, the antibody or antigen-binding fragment thereof binds to a mammalian HMGB polypeptide (e.g., rat HMGB, mouse HMGB, human HMGB). In still another embodiment, the antibody or antigen-binding fragment thereof binds to a mammalian HMGB1 polypeptide (e.g., rat HMGB1, mouse HMGB1, human HMGB1). In a particular embodiment, the antibody or antigen-binding fragment thereof binds to a human HMGB1 polypeptide (e.g., the human HMGB1 polypeptide depicted as SEQ ID NO:1 or SEQ ID NO:74).

The compositions and methods of the present invention also feature antibodies to the high mobility group B (HMGB) A box. In one embodiment, the antibody or antigen-binding fragment thereof binds to an HMGB A box but does not specifically bind to non-A box epitopes of HMGB. In another embodiment, the antibody or antigen-binding fragment thereof binds to a vertebrate HMGB A box but does not specifically bind to non-A box epitopes of HMGB. In another embodiment, the antibody or antigen-binding fragment thereof binds to a mammalian (e.g., human, rat, mouse) HMGB A box but does not specifically bind to non-A box epitopes of HMGB. In still another embodiment, the antibody or antigen-binding fragment thereof binds to the A box of a HMGB1 polypeptide (e.g., a mammalian HMGB1 polypeptide (e.g., human HMGB1, rat HMGB1, mouse HMGB1)) but does not specifically bind to non-A box epitopes of HMGB1.

As used herein, an "HMGB A box", also referred to herein as an "A box" or "HMG A box", is a protein or polypeptide that has at least 50%, 60%, 70%, 75%, 80%, 85%, 90% or 95%, sequence identity to an HMGB A box (e.g., an HMGB A box described herein). In one embodiment, the HMGB A box has one or more of the following biological activities: inhibiting inflammation mediated by HMGB and/or inhibiting release of a proinflammatory cytokine from a cell (see, e.g., PCT Publication No. WO 02/092004; the entire teachings of which are incorporated herein by reference). In one embodiment, the HMGB A box polypeptide has one of the above biological activities. Typically, the HMGB A box polypeptide has both of the above biological activities. In one embodiment, the A box has at least 50%, 60%, 70%, 75%, 80%, 85%, 90%, or 95%, sequence identity to the A box depicted in FIG. 2A (residues 9-85 of SEQ ID NO:2) or FIG. 31B (SEQ ID NO:75). In another embodiment, the A box comprises or consists of the amino acid sequence in the corresponding region of an HMGB protein in a mammal. An HMGB A box is also a recombinantly-produced polypeptide having the same amino acid sequence as the A box sequences described herein. The HMGB A box is preferably a vertebrate HMGB A box, for example, a mammalian HMGB A box, more preferably, a mammalian HMGB1 A box, for example, a human HMGB1 A box, and most preferably, the HMGB1 A box comprising or consisting of the sequence of the A box depicted in FIG. 2A (residues 9-85 of SEQ ID NO:2) or FIG. 31B (SEQ ID NO:75).

An HMGB A box often has no more than about 85 amino acids and no fewer than about 4 amino acids. In other embodiments, an HMGB A box can comprise from 10-85 amino acids, 20-85 amino acids, 30-85 amino acids or 40-85 amino acids. Examples of polypeptides having A box sequences within them include, but are not limited to the HMGB polypeptides described above. The A box sequences in such HMGB polypeptides can be determined and isolated using methods described herein, for example, by sequence comparisons to A boxes described herein and testing for biological activity using methods described herein and/or other methods known in the art.

Additional examples of HMGB A box polypeptide sequences include the following sequences: PDASVNFSEF SKKCSERWKT MSAKEKGKFE DMAKADKARY EREMKTYIPP KGET (human HMGB1; SEQ ID NO:55); DSSVNFAEF SKKCSERWKT MSAKEKSKFE DMAKSDKARY DREMKNYVPP KGDK (human HMGB2; SEQ ID NO:56); PEVPVNFAEF SKKCSERWKT VSGKEKSKFD EMAKADKVRY DREMKDYGPA KGGK (human HMGB3; SEQ ID NO:57); PDASVNFSEF SKKCSERWKT MSAKEKGKFE DMAKADKARY EREMKTYIPP KGET (HMG1L10; SEQ ID NO:58); SDASVNFSEF SNKCSERWK MSAKEKGKFE DMAKADKTHY ERQMKTYIPP KGET (HMG1L1; SEQ ID NO:59); PDASVNFSEF SKKCSERWKA MSAKDKGKFE DMAKVDKADY EREMKTYIPP KGET (HMG1L4; SEQ ID NO:60); PDASVKFSEF LKKCSETWKT IFAKEKGKFE DMAKADKAHY EREMKTYIPP KGEK (HMG sequence from BAC clone RP11-395A23; SEQ ID NO:61); PDASINFSEF SQKCPETWKT TIAKEKGKFE DMAKADKAHY EREMKTYIPP KGET (HMG1L9; SEQ ID NO:62); PDASVNSSEF SKKCSERWKTMPTKQGKFE DMAKADRAH (HMG1L8; SEQ ID NO:63); PDASVNFSEF SKKCLVRGKT MSAKEKGQFE AMARADKARY EREMKTYIP PKGET (LOC122441; SEQ ID NO:64); LDASVSFSEF SNKCSERWKT MSVKEKGKFE DMAKADKACY EREMKIYPYL KGRQ (LOC139603; SEQ ID NO:65); and GKGDPKKPRG KMSSYAFFVQ TCREEHKKKH PDASVNFSEF SKKCSERWKT MSAKEKGKFE DMAKADKARY EREMKTYIPP KGET (human HMGB1 A box; SEQ ID NO:66).

The compositions and methods of the present invention also feature antibodies to the high mobility group B (HMGB) B box. In one embodiment, the antibody or antigen-binding fragment thereof binds to an HMGB B box but does not specifically bind to non-B box epitopes of HMGB. In another embodiment, the antibody or antigen-binding fragment thereof binds to a vertebrate HMGB B box but does not specifically bind to non-B box epitopes of HMGB. In another embodiment, the antibody or antigen-binding fragment thereof binds to a mammalian (e.g., human, rat, mouse) HMGB B box but does not specifically bind to non-B box epitopes of HMGB. In still another embodiment, the antibody or antigen-binding fragment thereof binds to the B box of a HMGB1 polypeptide (e.g., a mammalian HMGB1 polypeptide (e.g., human HMGB1, rat HMGB1, mouse HMGB1)) but does not specifically bind to non-B box epitopes of HMGB1.

As used herein, an "HMGB B box", also referred to herein as a "B box" or "an HMG B box", is a polypeptide that has at least 60%, 65%, 70%, 75%, 80%, 85%, 90%, or 95%, sequence identity to an HMGB1 polypeptide (e.g., an HMGB B box described herein). In one embodiment, the HMGB1 box has one or more of the following biological activities: increasing inflammation and/or increasing release of a proinflammatory cytokine from a cell (see, e.g., PCT Publication No. WO 02/092004). In one embodiment, the HMGB B box polypeptide has one of the above biological activities. Typically, the HMGB B box polypeptide has both of the above biological activities. In one embodiment, the HMGB B box has at least 50%, 60%, 70%, 75%, 80%, 85%, 90% or 95%, sequence identity to the B box depicted in FIG. 2B (SEQ ID NO:3) or FIG. 31C (SEQ ID NO:76). In another embodiment, the B box comprises or consists of the amino acid sequence in the corresponding region of an HMGB protein in a mammal. An HMGB B box is also a recombinantly-produced polypeptide having the same amino acid sequence as the B box sequences described herein. The HMGB B box is preferably a vertebrate HMGB B box, for example, a mammalian HMGB B box, more preferably, a mammalian HMGB1 B box, for example, a human HMGB1 B box, and most preferably, the HMGB1 B box comprising or consisting of the sequence of the B box depicted in FIG. 2B (SEQ ID NO:3) or FIG. 31C (SEQ ID NO:76).

An HMGB B box often has no more than about 85 amino acids and no fewer than about 4 amino acids. Examples of polypeptides having B box sequences within them include, but are not limited to, the HMGB polypeptides described above. The B box sequences in such polypeptides can be determined and isolated using methods described herein, for example, by sequence comparisons to B boxes described herein and testing for biological activity.

Examples of additional HMGB B box polypeptide sequences include the following sequences: FKDPNAPKRP PSAFFLFCSE YRPKIKGEHP GLSIGDVAKK LGEMWNNTAA DDKQPYEKKA AKLKEKYEKD IAAY (human HMGB1; SEQ ID NO:67); KKDPNAPKRP PSAFFLFCSE HRPKIKSEHP GLSIGDTAKK LGEMWSEQSA KDKQPYEQKA AKLKEKYEKD IAAY (human HMGB2; SEQ ID NO:68); FKDPNAPKRL PSAFFLFCSE YRPKIKGEHP GLSIGDVAKK LGEMWNNTAA DDKQPYEKKA AKLKEKYEKD IAAY (HMG1L10; SEQ ID NO:69); FKDPNAPKRP PSAFFLFCSE YHPKIKGEHP GLSIGDVAKK LGEMWNNTAA DDKQPGEKKA AKLKEKYEKD IAAY (HMG1L1; SEQ ID NO:70); FKDSNAPKRP PSAFLLFCSE YCPKIKGEHP GLPISDVAKK LVEMWNNTFA DDKQLCEKKA AKLKEKYKKD TATY (HMG1L4; SEQ ID NO:71); FKDPNAPKRP PSAFFLFCSE YRPKIKGEHP GLSIGDVVKK LAGMWNNTAA ADKQFYEKKA AKLKEKYKKD IAAY (HMG sequence from BAC clone RP1'-359A23; SEQ ID NO:72); and FKDPNAPKRP PSAFFLFCSE YRPKIKGEHP GLSIGDVAKK LGEMWNNTAA DDKQPYEKKA AKLKEKYEKD IAAYRAKGKP DAAKKGVVKA EK (human HMGB1 box; SEQ ID NO:73).

As described herein, an HMGB polypeptide, an HMGB A box, and an HMGB B box, either naturally occurring or non-naturally occurring, encompass polypeptides that have sequence identity to the HMGB polypeptides, HMGB A boxes, and/or HMGB B boxes, described herein. As used herein, two polypeptides (or a region of the polypeptides) are substantially homologous or identical when the amino acid sequences are at least about 60%, 70%, 75%, 80%, 85%, 90%, or 95% or more, homologous or identical. The percent identity of two amino acid sequences (or two nucleic acid sequences) can be determined by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions× 100). In certain embodiments, the length of the HMGB polypeptide, HMGB A box polypeptide, or HMGB B box polypeptide, aligned for comparison purposes is at least 30%, preferably at least 40%, more preferably at least 60%, and even more preferably at least 70%, 80%, 90%, or 100%, of the length of the reference sequence, for example, the sequences described herein corresponding to an HMGB polypeptide (e.g., SEQ ID NO:1; SEQ ID NO:18, SEQ ID NO:74), an HMGB A box polypeptide (e.g., residues 9-85 of SEQ ID NO:2, SEQ ID NO:75) or an HMGB B box polypeptide (e.g., SEQ ID NO:3, SEQ ID NO:76). The actual comparison of the two sequences can be accomplished by well-known methods, for example, using a mathematical algorithm. A preferred, non-limiting example of such a mathematical algorithm is described in Karlin et al. (*Proc. Natl. Acad. Sci. USA*, 90:5873-5877 (1993)). Such an algorithm is incorporated into the BLASTN and BLASTX programs (version 2.2) as described in Schaffer et al. (*Nucleic Acids Res.*, 29:2994-3005 (2001)). When utilizing BLAST and Gapped BLAST programs, the default parameters of the respective programs (e.g., BLASTN; available at the Internet site for the National Center for Biotechnology Information) can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Another non-limiting example of a mathematical algorithm utilized for the comparison of sequences is the algorithm of Myers and Miller, CABIOS (1989). Such an algorithm is incorporated into the ALIGN program (version 2.0), which is part of the GCG (Accelrys, San Diego, Calif.) sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti (Comput. Appl. Biosci., 10: 3-5, 1994); and FASTA described in Pearson and Lipman (Proc. Natl. Acad. Sci USA, 85: 2444-2448, 1988).

In another embodiment, the percent identity between two amino acid sequences can be accomplished using the GAP program in the GCG software package (Accelrys, San Diego, Calif.) using either a Blossom 63 matrix or a PAM250 matrix, and a gap weight of 12, 10, 8, 6, or 4, and a length weight of 2, 3, or 4. In yet another embodiment, the percent identity between two nucleic acid sequences can be accomplished using the GAP program in the GCG software package (Accelrys, San Diego, Calif.), using a gap weight of 50 and a length weight of 3.

Inhibiting Release of Proinflammatory Cytokines and Methods of Treatment

In one embodiment, the present invention is a method of inhibiting release of a proinflammatory cytokine from a mammalian cell. In one embodiment, the method comprises treating the cell with an antibody or antigen-binding fragment of the present invention. Suitable antibodies or antigen-binding fragments are those described herein and include, e.g., 6E6 HMGB1 mAb, 6H9 HMGB1 mAb, 2G7 HMGB1 mAb, 10D4 HMGB1 mAb, 2E11 HMGB1 mAb, an antibody having the epitopic specificity of 6E6 HMGB1 mAb, 6H9 HMGB1 mAb, 2G7 HMGB1 mAb, 10D4 HMGB1 mAb and/or 2E11 HMGB1 mAb, an antibody that can compete with 6E6 HMGB1 mAb, 6H9 HMGB1 mAb, 2G7 HMGB1 mAb, 10D4 HMGB1 mAb and/or 2E11 HMGB1 mAb for binding to a vertebrate high mobility group box (HMGB) polypeptide, and an antigen-binding fragment of any of the foregoing.

As used herein, a "cytokine" is a soluble protein or peptide that is naturally produced by mammalian cells and that regulates immune responses and mediates cell-cell interactions. Cytokines can, either under normal or pathological conditions, modulate the functional activities of individual cells and tissues. A proinflammatory cytokine is a cytokine that is capable of causing one or more of the following physiological reactions associated with inflammation or inflammatory conditions: vasodilation, hyperemia, increased permeability of vessels with associated edema, accumulation of granulocytes and mononuclear phagocytes, and deposition of fibrin. In some cases, the proinflammatory cytokine can also cause apoptosis. For example, in chronic heart failure, it has been shown that TNF stimulates cardiomyocyte apoptosis (Pulkki, *Ann. Med.* 29:339-343 (1997); and Tsutsui, et al., *Immunol. Rev.* 174:192-209 (2000)). Nonlimiting examples of proinflammatory cytokines are tumor necrosis factor (TNF), interleukin (IL)-1α, IL-1β, IL-6, IL-8, IL-18, interferon ỹ, HMG-1, platelet-activating factor (PAF), and macrophage migration inhibitory factor (MIF).

In another embodiment, the invention is a method of treating a condition in a subject, wherein the condition is characterized by activation of an inflammatory cytokine cascade comprising administering to the subject an antibody or antigen-binding fragment of the present invention. Suitable antibodies or antigen-binding fragments are those described herein and include, e.g., 6E6 HMGB1 mAb, 6H9 HMGB1 mAb, 2G7 HMGB1 mAb, 10D4 HMGB1 mAb, 2E11 HMGB1 mAb, an antibody having the epitopic specificity of 6E6 HMGB1 mAb, 6H9 HMGB1 mAb, 2G7 HMGB1 mAb, 10D4 HMGB1 mAb and/or 2E11 HMGB1 mAb, an antibody that can compete with 6E6 HMGB1 mAb, 6H9 HMGB1 mAb, 2G7 HMGB1 mAb, 10D4 HMGB1 mAb and/or 2E11 HMGB1 mAb for binding to a vertebrate high mobility group box (HMGB) polypeptide, and an antigen-binding fragment of any of the foregoing.

In one embodiment, the method of treatment comprises administering to a subject an effective amount of an antibody or antigen-binding fragment of the invention. As used herein, an "effective amount" or "therapeutically effective amount" is an amount sufficient to prevent or decrease an inflammatory response, and/or to ameliorate and/or decrease the longevity of symptoms associated with an inflammatory response. The amount of the composition of the invention that will be effective in the treatment, prevention or management of a particular condition can be determined, for example, by administering the composition to an animal model such as, e.g., the animal models disclosed herein and/or known to those skilled in the art. In addition, in vitro assays may optionally be employed to help identify optimal dosage ranges.

Selection of the preferred effective dose can be determined (e.g., via clinical trials) by a skilled artisan based upon the consideration of several factors that are known to one of ordinary skill in the art. Such factors include, e.g., the condition or conditions to be treated, the severity of the subject's symptoms, the choice of antibody or antigen-binding fragment to be administered, the subject's age, the subject's body mass, the subject's immune status, the response of the individual subject, and other factors known by the skilled artisan to reflect the accuracy of administered pharmaceutical compositions.

Figure 16:
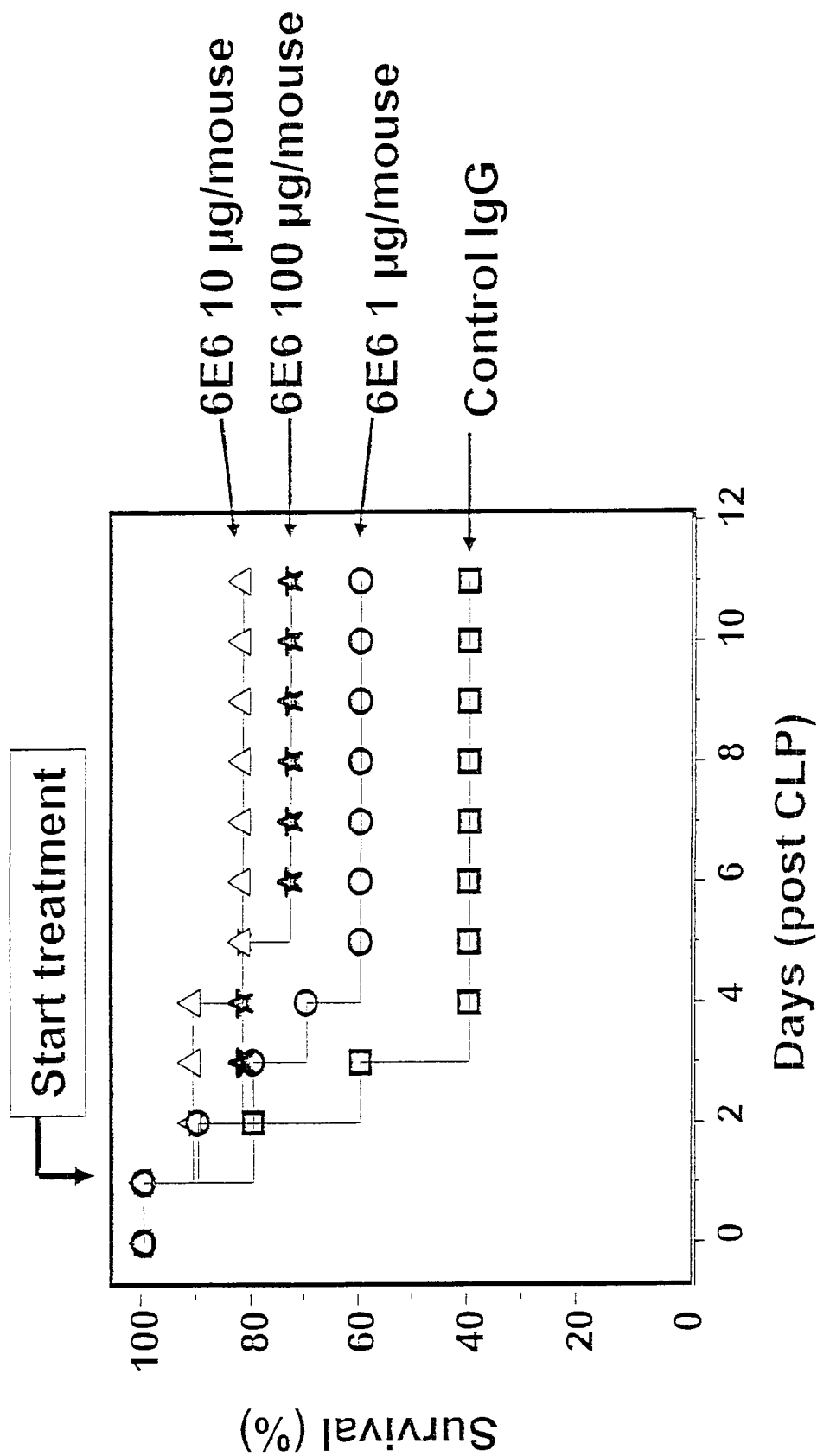
FIG. 16 is a graph depicting a dose response curve for anti-HMGB1 monoclonal antibody 6E6 HMGB1 mAb (6E6; at doses of 1 μg/mouse, 10 μg/mouse or 100 μg/mouse as labeled) or a control IgG antibody (Control IgG) on survival of mice over time (days) after cecal ligation and puncture (CLP).

The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems. For example, as exemplified herein, using an in vivo cecal ligation and puncture (CLP) assay, a dose response assay for anti-HMGB1 monoclonal antibody 6E6 HMGB1 mAb (at doses of 1 μg/mouse, 10 μg/mouse or 100 μg/mouse) was conducted (FIG. 16).

For antibodies, the dosage administered to a subject (e.g., a human patient) is typically 0.1 mg/kg to 100 mg/kg of the subject's body weight. Preferably, the dosage administered to a subject is between 0.1 mg/kg and 20 mg/kg of the subject's body weight, more preferably 1 mg/kg to 10 mg/kg of the subject's body weight. In certain embodiments of the invention, the dosage is at least 1 mg/kg, or at least 5 mg/kg, or at least 10 mg/kg, or at least 50 mg/kg, or at least 100 mg/kg, or at least 150 mg/kg, of the subject's body weight. Generally, human and humanized antibodies have a longer half-life within the human body than antibodies from other species due to the immune response to foreign polypeptides. Thus, lower dosages of human antibodies and less frequent administration is often possible. For example, an effective amount of an antibody can range from about 0.01 mg/kg to about 5 or 10 mg/kg administered daily, weekly, biweekly or monthly.

Methods for determining whether an antibody or antigen-binding fragment inhibits an inflammatory condition are known to one skilled in the art. For example, inhibition of the release of a proinflammatory cytokine from a cell can be measured according to methods known to one skilled in the art. For example, as described and exemplified herein, TNF release from a cell can be measured using a standard murine fibroblast L929 (ATCC, American Type Culture Collection, Rockville, Md.) cytotoxicity bioassay (Bianchi et al., *Journal of Experimental Medicine* 183:927-936 (1996)) with the minimum detectable concentration of 30 pg/ml. The L929 cytotoxicity bioassay is carried out as follows. RAW 264.7 cells are cultured in RPMI 1640 medium (Life Technologies, Grand Island, N.Y.) supplemented with 10% fetal bovine serum (Gemini, Catabasas, Calif.), and penicillin and streptomycin (Life Technologies). Polymyxin (Sigma, St. Louis, Mo.) is added at 100 units/ml to suppress the activity of any contaminating LPS. Cells are incubated with the antibodies described herein in OPTI-MEM® I medium (cell culture medium) for 8 hours, and conditioned supernatants (containing TNF that has been released from the cells) are collected. TNF that is released from the cells is measured by a standard murine fibroblast L929 (ATCC) cytotoxicity bioassay (Bianchi et al., supra) with the minimum detectable concentration of 30 pg/ml. Recombinant mouse TNF can be obtained from R & D Systems Inc. (Minneapolis, Minn.) and used as a control in these experiments. Methods for measuring release of other cytokines from cells are also known in the art.

An inflammatory condition that is suitable for the methods of treatment described herein can be one in which the inflammatory cytokine cascade is activated. In one embodiment, the inflammatory cytokine cascade causes a systemic reaction, such as with endotoxic shock. In another embodiment, the inflammatory condition is mediated by a localized inflammatory cytokine cascade, as in rheumatoid arthritis. Nonlimiting examples of inflammatory conditions that can be usefully treated using the antibodies and antigen-binding fragments of the present invention include, e.g., diseases involving the gastrointestinal tract and associated tissues (such as ileus, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, coeliac disease, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogenital system and associated tissues (such as septic abortion, epididymitis, vaginitis, prostatitis, and urethritis); diseases involving the respiratory system and associated tissues (such as bronchitis, emphysema, rhinitis, cystic fibrosis, pneumonitis, adult respiratory distress syndrome, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as stenosis, restenosis, vasulitis, angitis, endocarditis, arteritis, atherosclerosis, thrombophlebitis, pericarditis, congestive heart failure, myocarditis, myocardial ischemia, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fascitis, Paget's disease, gout, periodontal disease, rheumatoid arthritis, and synovitis); other autoimmune and inflammatory disorders (such as myasthenia gravis, thyroiditis, systemic lupus erythematosus, Goodpasture's syndrome, Behcets's syndrome, allograft rejection, graft-versus-host disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease.

In one embodiment, the condition is selected from the group consisting of sepsis, allograft rejection, arthritis (e.g., rheumatoid arthritis), asthma, atherosclerosis, restenosis, lupus, adult respiratory distress syndrome, chronic obstructive pulmonary disease, psoriasis, pancreatitis, peritonitis, burns, myocardial ischemia, organic ischemia, reperfusion ischemia, Behcet's disease, graft versus host disease, Crohn's disease, ulcerative colitis, ileus, multiple sclerosis, and cachexia. In another embodiment, the condition is selected from the group consisting of sepsis, arthritis (e.g., rheumatoid arthritis), asthma, lupus, psoriasis, inflammatory bowel disease and Crohn's disease.

Preferably the antibodies and antigen-binding fragments are administered to a patient in need thereof in an amount sufficient to inhibit release of proinflammatory cytokine from a cell and/or to treat an inflammatory condition. In one embodiment, release of the proinflammatory cytokine is inhibited by at least 10%, 20%, 25%, 50%, 75%, 80%, 90%, or 95%, as assessed using methods described herein or other methods known in the art.

The terms "therapy", "therapeutic" and "treatment", as used herein, refer to ameliorating symptoms associated with a disease or condition, for example, an inflammatory disease or an inflammatory condition, including preventing or delaying the onset of the disease symptoms, and/or lessening the severity or frequency of symptoms of the disease or condition. The terms "subject" and "individual" are defined herein to include animals such as mammals, including but not limited to, primates, cows, sheep, goats, horses, dogs, cats, rabbits, guinea pigs, rats, mice or other bovine, ovine, equine, canine, feline, rodent, or murine species. In one embodiment, the animal is a human.

In one embodiment, an excipient can be included with the antibodies and antigen-binding fragments of the invention. The excipient can be selected based on the expected route of administration of the antibodies or antigen-binding fragments in therapeutic applications. The route of administration of the composition depends on the condition to be treated. For example, intravenous injection may be preferred for treatment of a systemic disorder such as endotoxic shock, and oral administration may be preferred to treat a gastrointestinal disorder such as a gastric ulcer. As described above, the dosage of the antibody or antigen-binding fragment to be administered can be determined by the skilled artisan without undue experimentation in conjunction with standard dose-response studies. Depending on the condition, the antibody or antigen-binding fragment can be administered orally, parenterally, intranasally, vaginally, rectally, lingually, sublingually, bucally, intrabucally and transdermally to the patient.

Accordingly, antibodies or antigen-binding fragments designed for oral, lingual, sublingual, buccal and intrabuccal administration can be made without undue experimentation by means well known in the art, for example, with an inert diluent and/or edible carrier. The antibodies or antigen-binding fragments may be enclosed in gelatin capsules or compressed into tablets. For the purpose of oral therapeutic administration, the antibodies or antigen-binding fragments of the present invention may be incorporated with excipients and used in the form of tablets, troches, capsules, elixirs, suspensions, syrups, wafers, chewing gums, and the like.

Tablets, pills, capsules, troches, and the like, may also contain binders, recipients, disintegrating agent, lubricants, sweetening agents, and flavoring agents. Some examples of binders include microcrystalline cellulose, gum tragacanth, and gelatin. Examples of excipients include starch and lactose. Some examples of disintegrating agents include alginic acid, corn starch, and the like. Examples of lubricants include magnesium stearate and potassium stearate. An example of a glidant is colloidal silicon dioxide. Some examples of sweetening agents include sucrose, saccharin, and the like. Examples of flavoring agents include peppermint, methyl salicylate, orange flavoring, and the like. Materials used in preparing these various compositions should be pharmaceutically pure and non-toxic in the amounts used.

The antibodies and antigen-binding fragments of the present invention can be administered parenterally such as, for example, by intravenous, intramuscular, intrathecal or subcutaneous injection. Parenteral administration can be accomplished by incorporating the antibodies and antigen-binding fragments of the present invention into a solution or suspension. Such solutions or suspensions may also include sterile diluents, such as water for injection, saline solution, bacteriostatic saline (saline containing about 0.9% mg/ml benzyl alcohol), phosphate-buffered saline (referred to herein as PBS), Hank's solution, Ringer's-lactate, fixed oils, polyethylene glycols, glycerine, propylene glycol, and other synthetic solvents. Parenteral formulations may also include antibacterial agents (e.g., benzyl alcohol, methyl parabens), antioxidants (e.g., ascorbic acid, sodium bisulfite), and chelating agents (e.g., EDTA). Buffers, such as acetates, citrates or phosphates and agents for the adjustment of tonicity such as sodium chloride and dextrose, may also be added. The parenteral preparation can be enclosed in ampules, disposable syringes, or multiple dose vials made of glass or plastic.

Rectal administration includes administering the antibodies and antigen-binding fragments into the rectum or large intestine. This can be accomplished using suppositories or enemas. Suppository formulations can be made by methods known in the art. For example, suppository formulations can be prepared by heating glycerin to about 120° C., dissolving the antibody or antigen-binding fragment in the glycerin, mixing the heated glycerin, after which purified water may be added, and pouring the hot mixture into a suppository mold.

Transdermal administration includes percutaneous absorption of the antibody or antigen-binding fragment through the skin. Transdermal formulations include patches, ointments, creams, gels, salves, and the like.

The antibodies and antigen-binding fragments of the present invention can be administered nasally to a subject. As used herein, nasally administering or nasal administration, includes administering the antibodies or antigen-binding fragments to the mucous membranes of the nasal passage or nasal cavity of the subject. Pharmaceutical compositions for nasal administration of an antibody or antigen-binding fragment include therapeutically effective amounts of the antibody or antigen-binding fragment. Well-known methods for nasal administration include, for example, as a nasal spray, nasal drop, suspension, gel, ointment, cream, or powder. Administration of the antibody or antigen-binding fragment may also take place using a nasal tampon or nasal sponge.

As described above, a variety of routes of administration are possible including, for example, oral, dietary, topical, transdermal, rectal, parenteral (e.g., intravenous, intraarterial, intramuscular, subcutaneous, intradermal injection), and inhalation (e.g., intrabronchial, intranasal, oral inhalation, intranasal drops). Administration can be local or systemic as indicated. The preferred mode of administration can vary depending upon the antibody or antigen-binding fragment to be administered and the particular condition (e.g., disease) being treated, however, oral or parenteral administration is generally preferred.

If desired, the antibodies or antigen-binding fragments described herein can be administered with one or more additional agents (e.g., agents used to treat an inflammatory condition). The antibodies or antigen-binding fragments thereof and additional agent(s) can be present in a single composition or administered as separate compositions. If administered as separate compositions, the antibodies or antigen-binding fragments thereof and additional agent(s) can be co-administered or administered separately.

In one embodiment, the antibodies or antigen-binding fragments of the invention are administered with an anti-inflammatory agent. Such agents are known to one of skill in the art. In one embodiment, the agent is an antagonist of an early sepsis mediator. As used herein, an early sepsis mediator is a proinflammatory cytokine that is released from cells soon (i.e., within 30-60 min.) after induction of an inflammatory cytokine cascade (e.g., exposure to LPS). Nonlimiting examples of these cytokines are IL-1α, IL-1β, IL-6, PAF, and MIF. Also included as early sepsis mediators are receptors for these cytokines (for example, tumor necrosis factor receptor type 1) and enzymes required for production of these cytokines, for example, interleukin-1β converting enzyme). Antagonists of any early sepsis mediator, now known or later discovered, can be useful for these embodiments by further inhibiting an inflammatory cytokine cascade.

Nonlimiting examples of antagonists of early sepsis mediators are antisense compounds that bind to the mRNA of the early sepsis mediator, preventing its expression (see, e.g., Ojwang et al., *Biochemistry* 36:6033-6045 (1997); Pampfer et al., *Biol. Reprod.* 52:1316-1326 (1995); U.S. Pat. No. 6,228,642; Yahata et al., *Antisense Nucleic Acid Drug Dev.* 6:55-61 (1996); and Taylor et al., *Antisense Nucleic Acid Drug Dev.* 8:199-205 (1998)), ribozymes that specifically cleave the mRNA of the early sepsis mediator (see, e.g., Leavitt et al., *Antisense Nucleic Acid Drug Dev.* 10:409-414 (2000); Kisich et al., *J. Immunol.* 163(4):2008-2016 (1999); and Hendrix et al., *Biochem. J.* 314 (Pt. 2):655-661 (1996)), and antibodies that bind to the early sepsis mediator and inhibit their action (see, e.g., Kam and Targan, *Expert Opin. Pharmacother.* 1:615-622 (2000); Nagahira et al., *J. Immunol. Methods* 222:83-92 (1999); Lavine et al., *J. Cereb. Blood Flow Metab.* 18:52-58 (1998); and Holmes et al., *Hybridoma* 19:363-367 (2000)). An antagonist of an early sepsis mediator, now known or later discovered, is envisioned as within the scope of the invention. The skilled artisan can determine the amount of early sepsis mediator to use for inhibiting any particular inflammatory cytokine cascade without undue experimentation with routine dose-response studies.

Other agents that can be administered with the antibodies and antigen-binding fragments of the invention include, e.g., VITAXIN™ (investigational monoclonal antibody) and other antibodies targeting αvβ3 integrin (see, e.g., U.S. Pat. No. 5,753,230, PCT Publication Nos. WO 00/78815 and WO 02/070007; the entire teachings of all of which are incorporated herein by reference) and anti-IL-9 antibodies (see, e.g., PCT Publication No. WO 97/08321; the entire teachings of which are incorporated herein by reference).

In one embodiment, the antibodies and antigen-binding fragments of the invention are administered with inhibitors of TNF biological activity e.g., inhibitors of TNF-α biological activity). Such inhibitors of TNF activity include, e.g., peptides, proteins, synthesized molecules, for example, synthetic organic molecules, naturally-occurring molecule, for example, naturally occurring organic molecules, nucleic acid molecules, and components thereof. Preferred examples of agents that inhibit TNF biological activity include infliximab (REMICADE®; Centocor, Inc., Malvern, Pa.), etanercept (ENBREL®; Immunex; Seattle, Wash.), adalimumab (D2E7; Abbot Laboratories, Abbot Park Ill.), CDP870 (Pharmacia Corporation; Bridgewater, N.J.) CDP571 (Celltech Group plc, United Kingdom), Lenercept (Roche, Switzerland), and Thalidomide.

In certain embodiments, the present invention is directed to a composition comprising the antibody or antigen-binding fragments described herein, in a pharmaceutically-acceptable excipient. As described above, the excipient included with the antibody or antigen-binding fragment in these compositions is selected based on the expected route of administration of the composition. Suitable pharmaceutically-acceptable excipients include those described above and known to those of skill in the art.

In one embodiment, the invention is directed to aptamers of HMGB (e.g., aptamers of HMGB1). As is known in the art, aptamers are macromolecules composed of nucleic acid (e.g., RNA, DNA) that bind tightly to a specific molecular target (e.g., an HMGB protein, an HMGB box (e.g., an HMGB A box, an HMGB B box), an HMGB polypeptide and/or an HMGB epitope as described herein). A particular aptamer may be described by a linear nucleotide sequence and is typically about 15-60 nucleotides in length. The chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Selection of apatmers that can bind HMGB or a fragment thereof (e.g., HMGB1 or a fragment thereof) can be achieved through methods known in the art. For example, aptamers can be selected using the SELEX (Systematic Evolution of Ligands by Exponential Enrichment) method (Tuerk, C., and Gold, L., *Science* 249:505-510 (1990)). In the SELEX method, a large library of nucleic acid molecules (e.g., $10^{15}$ different molecules) is produced and/or screened with the target molecule (e.g., an HMGB protein, an HMGB box (e.g., an HMGB A box, an HMGB B box), an HMGB polypeptide and/or an HMGB epitope as described herein). The target molecule is allowed to incubate with the library of nucleotide sequences for a period of time. Several methods, known in the art, can then be used to physically isolate the aptamer target molecules from the unbound molecules in the mixture, which can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this iterative selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure, thereby producing aptamers truncated to their core binding domain. See Jayasena, S. D. *Clin. Chem.* 45:1628-1650 (1999) for review of aptamer technology; the entire teachings of which are incorporated herein by reference).

In particular embodiments, the aptamers of the invention have the binding specificity and/or functional activity described herein for the antibodies of the invention. Thus, for example, in certain embodiments, the present invention is drawn to aptamers that have the same or similar binding specificity as described herein for the antibodies of the invention (e.g., binding specificity for a vertebrate HMGB polypeptide, fragment of a vertebrate HMGB polypeptide (e.g., HMGB A box, HMGB B box), epitopic region of a vertebrate HMGB polypeptide (e.g., epitopic region of HMGB1 that is bound by one or more of the antibodies of the invention)). In particular embodiments, the aptamers of the invention can bind to an HMGB polypeptide or fragment thereof and inhibit one or more functions of the HMGB polypeptide. As described herein, function of HMGB polypeptides include, e.g., increasing inflammation, increasing release of a proinflammatory cytokine from a cell, binding to RAGE, binding to TLR2, chemoattraction In a particular embodiment, the aptamer binds HMGB1 (e.g., human HMGB1 (e.g., as depicted in SEQ ID NO:1 or SEQ ID NO:74)) or a fragment thereof (e.g., A box (e.g., residues 9-85 of SEQ ID NO:2, SEQ ID NO:75), B box (e.g., SEQ ID NO:3, SEQ ID NO:76), HMGB1 antibody binding epitope as described herein) and inhibits one or more functions of the HMGB polypeptide (e.g., inhibits release of a proinflammatory cytokine from a vertebrate cell treated with HMGB).

Methods of Diagnosis and/or Prognosis

In another embodiment, the invention further provides diagnostic and/or prognostic methods for detecting a vertebrate high mobility group box (HMGB) polypeptide in a sample. In one embodiment of the method, a sample is contacted with an antibody or antigen-binding fragment of the present invention, under conditions suitable for binding of the antibody or fragment to an HMGB polypeptide present in the sample. The method further comprises detecting antibody-HMGB complexes or antigen-binding fragment-HMGB complexes, wherein detection of antibody-HMGB complexes or antigen-binding fragment-HMGB complexes is indicative of the presence of an HMGB polypeptide in the sample. Suitable antibodies or antigen-binding fragments for use in these methods include those described herein, e.g., 6E6 HMGB1 mAb, 6H9 HMGB1 mAb, 2G7 HMGB1 mAb, 10D4 HMGB1 mAb, 2E11 HMGB1 mAb, an antigen-binding fragment of any of the foregoing.

In another embodiment, the antibody or antigen-binding fragment comprises a detectable label. Labels suitable for use in detection of a complex between an HMGB polypeptide (e.g., a mammalian HMGB polypeptide) and an antibody or antigen-binding fragment include, for example, a radioisotope, an epitope label (tag), an affinity label (e.g., biotin, avidin), a spin label, an enzyme, a fluorescent group or a chemiluminescent group.

As described, the antibodies and antigen-binding fragments described herein can be used to detect or measure expression of an HMGB polypeptide. For example, antibodies of the present invention can be used to detect or measure an HMGB polypeptide in a biological sample (e.g., cells, tissues or body fluids from an individual such as blood, serum, leukocytes (e.g., activated T lymphocytes), bronchioalveolar lavage fluid, saliva, bowel fluid, synovial fluid, biopsy specimens). In one embodiment, the sample is blood or serum. For example, a sample (e.g., tissue and/or fluid) can be obtained from an individual and a suitable assay can be used to assess the presence or amount of an HMGB polypeptide. Suitable assays include immunological and immunochemical methods such as flow cytometry (e.g., FACS analysis) and immunosorbent assays, including enzyme-linked immunosorbent assays (ELISA), radioimmunoassay (RIA), chemiluminescence assays, immunoblot (e.g., western blot), immunocytochemistry and immunohistology. Generally, a sample and an antibody or antigen-binding fragment of the present invention are combined under conditions suitable for the formation of a complex between an HMGB polypeptide and the antibody or antigen-binding fragment thereof, and the formation of said complex is assessed (directly or indirectly). In one embodiment, diagnosis and/or prognosis is done using ELISA and/or western blot analysis.

As is known in the art, the presence of an increased level of an HMGB polypeptide (e.g., HMGB1) in a sample (e.g., a tissue sample) obtained from an individual can be a diagnostic and/or prognostic indicator for monitoring the severity and predicting the likely clinical course of sepsis for a subject exhibiting symptoms associated with conditions characterized by activation of the inflammatory cascade (see U.S. Pat. No. 6,303,321, the entire teachings of which are incorporated herein by reference). Thus, in one embodiment, the antibodies and antigen-binding fragments of the invention can be used in diagnostic and prognostic methods for monitoring the severity and/or predicting the likely clinical course of an inflammatory condition associated with HMGB expression (e.g., the conditions described herein). In certain embodiments, the diagnostic and/or prognostic methods comprise measuring the concentration of HMGB in a sample, preferably a serum sample, and comparing that concentration to a standard for HMGB representative of a normal concentration range of HMGB in a like sample, whereby higher levels of HMGB are indicative of poor prognosis or the likelihood of toxic reactions. The diagnostic method may also be applied to other tissue or fluid compartments such as cerebrospinal fluid or urine.

In another embodiment, the invention is a test kit for use in detecting the presence of a vertebrate high mobility group box (HMGB) polypeptide or portion thereof in a sample. Such test kits can comprise, e.g., an antibody or antigen-binding fragment of the invention and one or more ancillary reagents suitable for detecting the presence of a complex between the antibody or antigen-binding fragment and an HMGB polypeptide or portion thereof. The antibody and antigen-binding fragments of the present invention can be provided in lyophilized form, either alone or in combination with additional antibodies specific for other epitopes. The antibodies or antigen-binding fragments thereof, which can be labeled or unlabeled, can be included in the kits with adjunct ingredients (e.g., buffers, such as Tris (Tris(hydroxymethyl)aminomethane), phosphate and carbonate, stabilizers, excipients, biocides and/or inert proteins, e.g., bovine serum albumin). For example, the antibodies or antigen-binding fragments can be provided as a lyophilized mixture with the adjunct ingredients, or the adjunct ingredients can be separately provided for combination by the user. Generally these adjunct materials will be present in less than about 5% by weight based on the amount of active antibody, and usually will be present in a total amount of at least about 0.001% by weight based on antibody concentration. Where a second antibody or antigen-binding fragment capable of binding to the anti-HMGB antibody or antigen-binding fragment is employed, such antibody or fragment can be provided in the kit, for instance in a separate vial or container. The second antibody or antigen-binding fragment, if present, is typically labeled, and can be formulated in an analogous manner with the antibody formulations described above. The antibodies, antigen-binding fragments and/or ancillary reagent of the kit can be packaged separately or together within suitable containment means (e.g., bottle, box, envelope, tube). When the kit comprises a plurality of individually packaged components, the individual packages can be contained within a single larger containment means (e.g., bottle, box, envelope, tube).

Methods of Screening

In another embodiment, the invention is a method of detecting or identifying an agent that binds to an HMGB polypeptide (e.g., a mammalian HMGB polypeptide (e.g., an HMGB1 polypeptide)). In one embodiment, the method of detecting or identifying an agent that binds to an HMGB polypeptide is a competitive binding assay in which the ability of a test agent to inhibit the binding of an antibody or antigen-binding fragment of the invention is assessed. For example, the antibody or antigen-binding fragment can be labeled with a suitable label as described herein, and the amount of labeled antibody or antigen-binding fragment required to saturate the HMGB polypeptide present in the assay can be determined. For example, a saturating amount of labeled antibody or antigen-binding fragment and various amounts of a test agent can be contacted with an HMGB polypeptide under conditions suitable for binding, and complex formation determined. In this type of assay, a decrease in the amount of complex formed between the labeled antibody or antigen-binding fragment and HMGB polypeptide indicates that the test agent binds to the HMGB polypeptide. In another embodiment, the HMGB polypeptide can be labeled. Suitable labels for labeling antibodies, antigen-binding fragments and/or HMGB polypeptides include those described above.

A variety of agents, such as proteins (e.g., antibodies), peptides, peptidomimetics, small organic molecules, nucleic acids and the like, can be tested for binding to an HMGB polypeptide (e.g., a mammalian HMGB polypeptide (e.g., an HMGB1 polypeptide)). According to the method of the present invention, agents can be individually screened or one or more agents can be tested simultaneously. Where a mixture of compounds is tested, the compounds selected by the processes described can be separated (as appropriate) and identified using suitable methods (e.g., sequencing, chromatography). The presence of one or more compounds (e.g., a ligand, inhibitor, promoter) in a test sample can also be determined according to these methods.

Agents that bind to an HMGB polypeptide and that are useful in the therapeutic methods described herein can be identified, for example, by screening libraries or collections of molecules, such as, the Chemical Repository of the National Cancer Institute, in assays described herein or using other suitable methods. Libraries, such as combinatorial libraries, of compounds (e.g., organic compounds, recombinant or synthetic peptides, "peptoids", nucleic acids) produced by combinatorial chemical synthesis or other methods can be tested (see e.g., Zuckerman, R. N. et al, *J. Med. Chem.*, 37: 2678-2685 (1994) and references cited therein; see also, Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a library carry unique tags, identification of individual compounds by chromatographic methods is possible.

The present invention will now be illustrated by the following Examples, which are not intended to be limiting in any way. The relevant teachings of all publications cited herein that have not explicitly been incorporated herein by reference, are incorporated herein by reference in their entirety.

EXAMPLE 1

Materials and Methods

Generation of Monoclonal Antibodies to HMGB1

BALB/c mice were intraperitoneally immunized with 20 µg of recombinant CBP-Rat HMGB1 (CBP linked to amino acids 1-215 of rat HMGB1; nucleotide sequence of CBP-Rat HMGB1 is depicted as SEQ ID NO:4 and the amino acid sequence is depicted as SEQ ID NO:5 (see FIGS. 3A and 3B)) mixed with Freund's adjuvant at two-week intervals for 6 weeks. A final boost of 10 µg of the CBP-Rat HMGB1 in PBS was given intravenously after 8 weeks. Four days after the final boost, spleens from the mice were isolated and used for fusion. Fusion was carried out using standard hybridoma technique. The spleen was gently pushed through a cell strainer to obtain a single cell suspension. After extensive washing, spleen cells were mixed with SP2/0 myeloma cells. Polyethylene glycol (PEG) was added slowly, followed by media over a period of five minutes. The cells were washed and resuspended in DMEM containing 20% FCS and HAT, transferred to 96 well plates and incubated at 37° C. with 10% $CO_2$ for 10-14 days.

In other experiments, a human HMGB1 B box polypeptide (SEQ ID NO:3; FIG. 2B) was used as an immunogen. Five female BALB/c mice were intraperitoneally immunized with 10 µg/injection of HMGB1 B box mixed with Freund's adjuvant at three-week intervals. A bleed was obtained from the mice 1 week after each boost. Three weeks after the third boost, a final intravenous injection (10 µg/mouse) of the rat HMGB1 B box was given. 72 hours after the final boost, hybridoma fusions were carried out as described above. Hybridomas were cultured in DMEM with 20% FBS, HAT, CondiMed and 1% pen/strep. Positive clones were identified by taking optical readings and identifying those with readings five times that of background.

Antibodies to the CBP-Rat HMGB1 and human HMGB1 B box were screened by limiting dilution and ELISA. ELISA plates were coated with recombinant HMGB1 at 3 µg/ml overnight and blocked with phosphate buffered saline (PBS) supplemented with 1% bovine serum albumin (BSA). Supernatants from the hybridomas were added to the ELISA plates and incubated at room temperature for 30 minutes. The plates were then washed and anti-mouse Ig conjugated with horseradish peroxidase was added. After 30 minutes of incubation at room temperature, the plates were washed and developed. Cells from positive cells were transferred to 24-well plates and cloned by limiting dilution.

HMGB1 Stimulated TNF Release

The mouse macrophage cell line RAW 264.7 (available from the American Type Culture Collection (ATCC), Manassas, Va.) was incubated with various concentrations of HMGB1 for 4 hours at 37° C. in serum-free OPTI-MEM® (cell culture medium; Invitrogen, Carlsbad, Calif.). The supernatants were harvested and TNF level was measured using an ELISA kit (R&D Systems, Minneapolis, Minn.). The assay was also performed using heparinized whole blood. In this case, HMGB1 was diluted in OPTI-MEM® (cell culture medium), added to 100 µl of whole blood to give a final volume of 200 µl, and placed in a U-bottom 96-well plate. The plates were then incubated for 4 hours at 37° C. and plasma was harvested for ELISA analysis.

To screen for blocking mAbs to HMGB1, purified mAbs were diluted in OPTI-MEM® (cell culture medium) and mixed with rat HMGB1 at room temperature. After five minutes, the mixture was transferred into tissue culture wells containing RAW 264.7 cells. The plates were then incubated for 4 hours at 37° C. and supernatants were harvested for ELISA analysis.

SDS-Polyacrylamide Gel Electrophoresis, Western Blot Analysis and Selectivity of HMGB1 Monoclonal Antibodies For detection of HMGB1 with the HMGB1 mAbs, samples were mixed with 4× NUPAGE® LDS Sample Buffer (protein analysis sample buffer), 10× NUPAGE® Sample Reducing Agent (protein analysis reducing agent, Invitrogen, Carlsbad, Calif.). The samples were heated in boiling water for 5 minutes, immediately chilled on ice and loaded on an SDS-polyacrylamide gel. Western blot analysis was performed using standard techniques.

Figure 11:
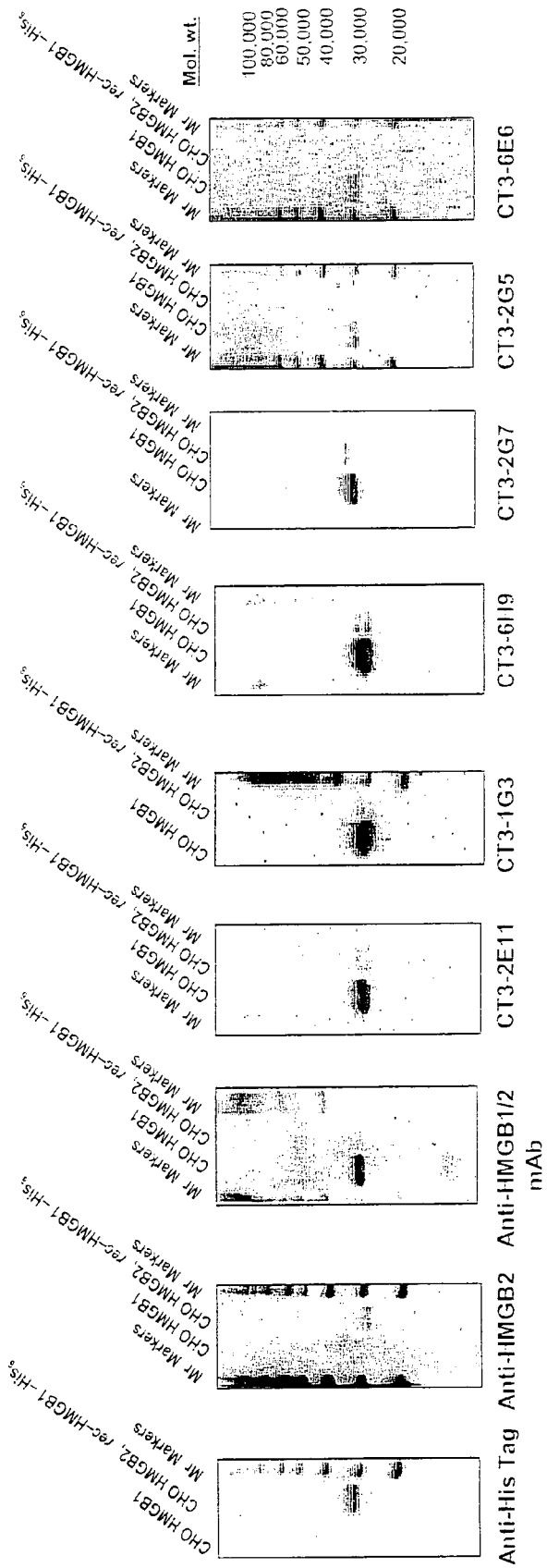
FIG. 11 depicts a series of individual Western blots of samples containing either CHO HMGB1 or CHO HMGB2 and possibly recombinant HMGB1-His$_6$ (labeled as CHO HMGB2, rec-HMGB1-His$_6$), which were probed with either an anti-His Tag antibody (Anti-His Tag), an anti-HMGB2 antibody (Anti-HMGB2), an anti-HMGB1/2 monoclonal antibody (Anti-HMGB1/2 mAb) or particular anti-HMGB1 monoclonal antibodies (i.e., 2E11 HMGB1 mAb (CT3-2E11), 1G3 HMGB1 mAb (CT3-1G3), 6H9 HMGB1 mAb (CT3-6H9), 2G7 HMGB1 mAb (CT3-2G7), 2G5 HMGB1 mAb (CT3-2G5) and 6E6 HMGB1 mAb (CT3-6E6)).

For the experiments determining selectivity of the HMGB1 monoclonal antibodies (i.e., selectivity for HMGB1 and/or HMGB2), western blot analysis was performed on samples containing non-recombinant (i.e., natural) HMGB1 from Chinese Hamster Ovary (CHO) cells (FIG. 11; labeled as CHO HMGB1; SEQ ID NO:36) or samples containing non-recombinant (i.e., natural) HMGB2 from Chinese Hamster Ovary (CHO) cells and some detectable recombinant human HMGB1-$His_6$ (FIG. 11; labeled as CHO HMGB2, rec-HMGB1-$His_6$). FIGS. 18A and 18B depict the nucleotide and encoded amino acid sequences of the human recombinant HMGB1 polypeptide containing a 5' 6 HIS tag (rec-HMGB1-$His_6$; SEQ ID NOs:39 and 40).

For the samples containing CHO HMGB1, samples contained ~2.5-5 ng/µl of non-recombinant (i.e., natural) HMGB1 from Chinese Hamster Ovary (CHO) cells. 20 µl of the sample (i.e., ~50-100 ng of HMGB1) was loaded on a gel and subjected to SDS-PAGE. To isolate CHO HMGB1 polypeptide, CHO cells were lysed and subsequently cleared by centrifugation. Anion exchange chromatography and heparin-affinity chromatography were then performed and fractions containing peak HMGB1 immunoreactivity but no detectable HMGB2 immunoreactivity were pooled and used as the source of CHO HMGB1.

For the samples containing non-recombinant (i.e., natural) HMGB2 from Chinese Hamster Ovary (CHO) cells and some detectable recombinant HMGB1-$His_6$ (FIG. 11; labeled as CHO HMGB2, rec-HMGB1-$His_6$), CHO cells transfected with a recombinant HMGB1-$His_6$-expressing plasmid were utilized. To isolate CHO HMGB2 polypeptide, CHO cells were lysed and subsequently cleared by centrifugation. Anion exchange chromatography and heparin-affinity chromatography were then performed and fractions containing peak HMGB2 immunoreactivity, but no detectable natural HMGB1 immunoreactivity, were pooled and used as the source of CHO HMGB2. In some cases, the pooled CHO HMGB2 fractions contained detectable amounts of recombinant HMGB-1-$His_6$ polypeptide, however, this recombinant HMGB-1-$His_6$ polypeptide was easily distinguished from HMGB2 based on its decreased mobility (and apparent higher molecular weight) when subjected to SDS-PAGE. Using the gel systems that generated the Western blots depicted in FIG. 11, non-recombinant CHO HMGB2 has an apparent molecular weight of ~27,000, non-recombinant CHO HMGB1 has an apparent molecular weight of ~29,000 and recombinant HMGB-1-$His_6$ has an apparent molecular weight of ~31,000. For the CHO HMGB2, rec-HMGB1-$His_6$ samples, 20 µl of the sample (i.e., ~10-20 ng of HMGB2) was loaded and subjected to SDS-PAGE.

For the western blots depicted in FIG. 11, either an anti-His Tag antibody (Santa Cruz, Calif.; 2 µg/ml), an anti-HMGB2 antibody (Pharmingen, San Diego, Calif.; 2 µg/ml), an anti-HMGB1/2 mAb (MBL International, Watertown, Mass.; 2 µg/ml) or particular anti-HMGB1 monoclonal antibodies (e.g., 2E11 HMGB1 mAb (CT3-2E11), 1G3 HMGB1 mAb (CT3-1G3), 6H9 HMGB1 mAb (CT3-6H9), 2G7 HMGB1 mAb (CT3-2G7), 2G5 HMGB1 mAb (CT3-2G5) and 6E6 HMGB1 mAb (CT3-6E6); 2 µg/ml for each) were used.

Sequencing of Monoclonal Antibodies

Total RNA was isolated from hybridoma cells using RNE-ASY® MiniKit (RNA purification kit; Qiagen, Valencia, Calif.) as described in the kit protocol. The first strand of cDNA synthesis was performed using PROTOSCRIPT® First Strand cDNA Synthesis kit (cDNA synthesis kit; New England Biolabs, Catalog #E6500S) as designed in the kit protocol. 5 µl of cDNA was added to a PCR reaction (as described in the protocol for Mouse Ig-Primer Set, Catalog #69831-3, Novagen, Madison, Wis.) containing 25 pmoles of the appropriate 5' primers (as described in the Novagen Ig-primer set protocol as MuIgGV$_H$5'-A, MuIgGV$_H$5'-B. MuIg-GV$_H$5'-C, MuIgGV$_H$5'-D, MuIgGV$_H$5'-E, MuIgGV$_H$5'-F for heavy chain and MuIgGV$_L$5'-A, MuIgGV$_L$5'-B, MuIgGV$_L$5'-C, MuIgGV$_L$5'-D, MuIgGV$_L$5'-E, MuIgGV$_L$5'-F and MuIg-GV$_L$5'-G for light chain) and 3' primers (as described in the Novagen Ig-primer set protocol as MuIgGV$_H$3'-2 for heavy chain and MuIgGV$_L$3'-2 for light chain). The PCR reaction conditions were 1 minute at 94° C., 1 minute at 50° C. and 2 minutes at 72° C. for 35 cycles, followed by an extension at 72° C. for 6 minutes. PCR products were cloned into vector TOPO (bacterial cloning vector; Invitrogen, San Diego, Calif.). DNA sequence analysis was performed by Genaissance Pharmaceuticals (New Haven, Conn.).

HMGB1 Peptide Binding Experiments

Biotinylated peptides bound to REACTI-BIND™ Streptavidin-Coated Plates (96-well coated plates; Pierce, Rockford, Ill., Catalog #15501) and non-biotinylated peptides bound to poly-D-lysine coated ELISA plates were used in anti-peptide ELISAs. Biotinylated peptides corresponding to particular 18 amino acid regions of human HMGB1, as well as a longer peptide corresponding to amino acid residues 9-85 of human HMGB1, were prepared and analyzed for binding to particular anti-HMGB1 monoclonal antibodies by ELISA. These peptides, and their respective sequences, are depicted in FIG. 13A. Poly-D-lysine coated plates were prepared by adding 60-100 µl/well of 0.1 mg/ml solution of poly-D-lysine in water. Plates were then incubated at room temperature for 5 minutes and were rinsed with water to remove the solution.

Briefly, using the molecular weight of the respective peptide, 1 mM peptide solutions were prepared in pyrogen-free water and diluted in 1× phosphate buffered saline. Plate wells were washed three times with 200 µl of PBS and 100 µl of the various peptide solutions were added to designated wells. The plates were then covered and incubated for 60 minutes at room temperature. The wells were then washed three times with PBS, 0.05% polyoxyethylenesorbitan (referred to herein as TWEEN 20™) using a volume greater than 100 µl. 200 µl of blocking buffer (5% nonfat dry milk in PBS, 0.05% TWEEN 20™) was added to each of the wells. The plates were covered and incubated for 60 minutes at room temperature. The wells were then washed three times with PBS, 0.05% TWEEN 20™ using a volume greater than 100 µl.

100 µl of the primary antibody (e.g., 2E11 HMGB1 mAb; 6E6 HMG31 mAb, 6H9 HMGB1 mAb, 2G7 HMGB1 mAb; 2 µg/ml in blocking buffer) was added to the designated wells and the plates were covered and incubated for 30 minutes at room temperature. The wells were then washed three times with PBS, 0.05% TWEEN 20™ using a volume greater than 100 µl.

100 µl of the goat anti-mouse horseradish peroxidase (HRP)-conjugated secondary antibody (Jackson ImmunoResearch Laboratories, West Grove, Pa., Catalog No. 115-035-071; used at a 1:2000 dilution) was added to each of the wells. The plates were covered, incubated for 30 minutes at room temperature and subsequently washed three times with times with PBS, 0.05% TWEEN 20™ using a volume greater than 100 µl. The plates were developed by adding 50 µl of 1×TMB (Sigma, St. Louis, Mo.) to each well, incubating for 10 minutes at room temperature and reading the absorbance at 655 nm using MICROPLATE MANAGER® (data collection software) and a BIORAD® Model 680 Plate Reader (microplate reader). Average background signal was subtracted from each of the sample signals.

Cecal Ligation and Puncture

Cecal ligation and puncture (CLP) was performed as described previously (Fink and Heard, J. Surg. Res. 49:186-196 (1990); Wichmann et al., Crit. Care Med. 26:2078-2086 (1998); and Remick et al., Shock 4:89-95 (1995)). Briefly, BALB/c mice were anesthetized with 75 mg/kg ketamine (Fort Dodge, Fort Dodge, Iowa) and 20 mg/kg of xylazine (Bohringer Ingelheim, St. Joseph, Mo.) intramuscularly. A midline incision was performed, and the cecum was isolated. A 6-0 prolene suture ligature was placed at a level 5.0 mm from the cecal tip away from the ileocecal valve.

The ligated cecal stump was then punctured once with a 22-gauge needle, without direct extrusion of stool. The cecum was then placed back into its normal intra-abdominal position. The abdomen was then closed with a running suture of 6-0 prolene in two layers, peritoneum and fascia separately to prevent leakage of fluid. All animals were resuscitated with a normal saline solution administered sub-cutaneously at 20 ml/kg of body weight. Each mouse received a subcutaneous injection of imipenem (0.5 mg/mouse) (Primaxin, Merck & Co., Inc., West Point, Pa.) 30 minutes after the surgery. Animals were then allowed to recuperate. Mortality was recorded for up to 1 week after the procedure; survivors were followed for 2 weeks to ensure no late mortalities had occurred.

Starting the day after the CLP procedure, 100 µg of particular anti-HMGB1 monoclonal antibodies (i.e., 6E6 HMGB1 mAb (mAB (6E6)); 2E11 HMGB1 mAb (mAB (2E11)); 9G2 HMGB1 mAb (mAB (9G2)) and a control IgG antibody were intraperitoneally administered to the mice once or twice a day for a total of 5 treatments. For the data presented in FIG. 16, various doses (1 µg/mouse, 10 µg/mouse or 100 µg/mouse) of 6E6 HMGB1 mAb or a control IgG antibody were intraperitoneally administered.

HMGB1 ELISA

Two ELISA methods were performed using various HMGB1 monoclonal antibodies.

HMGB1 ELISA with Monoclonal (Capture)+Polyclonal (Detector) Antibody Pairs

In the first method, ELISA plates were coated with a number of purified anti-HMGB1 mAbs (e.g., 2E11 HMGB1 mAb, 2G5 HMGB1 mAb, 2G7 HMGB1 mAb, 6E6 HMGB1 mAb), and incubated overnight at 4° C. The plates were then blocked with PBS, 1% BSA for one hour at 37° C. After washing, recombinant rat HMGB1 was added at the indicated concentrations, and the plates were incubated at room temperature for 1 hour. The plates were then washed and incubated with rabbit polyclonal antibodies against HMGB1 at 2 µg/ml (see U.S. Pat. Nos. 6,303,321, 6,448,223 and 6,468, 533). After 1 hour at room temperature, the plates were washed and incubated for 30 minutes with goat anti-rabbit Ig-HPR (Jackson ImmunoResearch Laboratories, West Grove, Pa.) diluted at 1:1000 in PBS. After washing, the plates were developed with TMB (Invitrogen, San Diego, Calif.) and absorbance at 655 nm was measured using a plate reader.

HMGB1 ELISA with Monoclonal Antibody Pairs (Detection with 6E6 HMGB1 mAb)

ELISA plates were coated and blocked, and recombinant rat HMGB1 was subsequently added as described above. After washing away the unbound HMGB1 polypeptide, biotinylated 6E6 HMGB1 mAb was added at 2 µg/ml and incubated for 1 hour at room temperature. Streptavidin-HRP was used to detect bound 6E6 HMGB1 mAb and the plates were developed with TMB as described above.

EXAMPLE 2

Identification and Characterization of Anti-HMGB1 Monoclonal Antibodies

A number of novel anti-HMGB1 monoclonal antibodies have been isolated and purified from immunizations with either recombinant full-length rat HMGB1 (SEQ ID NO:4; FIGS. 3A and 3B) or with a B-box polypeptide of human HMGB1 (SEQ ID NO:3; FIG. 2B). A table summarizing characteristics (clone name, immunogen, isotype, purified antibody binding domain, and results of in vivo CLP assays) of these antibodies is depicted in FIG. 7.

EXAMPLE 3

Determination of Selectivity of Anti-HMGB1 Monoclonal Antibodies

Experiments (e.g., ELISA, Western blot analysis) to determine the selectivity of the HMGB1 monoclonal antibodies revealed that particular anti-HMGB1 monoclonal antibodies are able to bind to the A box portion of HMGB1, the B box portion of HMGB1 and/or the whole HMGB1 protein. For example, as depicted in FIG. 7, anti-HMGB1 monoclonal antibodies were identified that can bind to the A box of HMGB1 (e.g., 6E6 HMGB1 mAb, 6H9 HMGB1 mAb, 10D4 HMGB1 mAb, 2G7 HMGB1 mAb, 2G5 HMGB1 mAb, 4H11 HMGB1 mAb, 7H3 HMGB1 mAb, 9H3 HMGB1 mAb). Other monoclonal antibodies were identified that bind to the B box of HMGB1 (e.g., 2E11 HMGB1 mAb, 3G8 HMGB1 mAb, 3-5A6 HMGB1 mAb, 9G1 HMGB1 mAb, 4C9 HMGB1 mAb, 1C3 HMGB1 mAb, 5C12 HMGB1 mAb, 3E10 HMGB1 mAb, 7G8 HMGB1 mAb, 4A 10 HMGB1 mAb).

EXAMPLE 4

Determination of Nucleotide and Amino Acid Sequences of Anti-HMGB1 Monoclonal Antibodies For particular HMGB1 monoclonal antibodies (6E6 HMGB1 mAb, 2E11 HMGB1 mAb, 10D4 HMGB1 mAb, 2G7 HMGB1 mAb), nucleotide and encoded amino acid sequences of $V_H$ domains and $V_K$ domains, including CDRs, were also obtained (FIGS. 4A-4D, 5A-5D, 6A-6D and 19A-19D).

EXAMPLE 5

Inhibition of TNF Release by Anti-HMGB1 Monoclonal Antibodies

Figure 9:
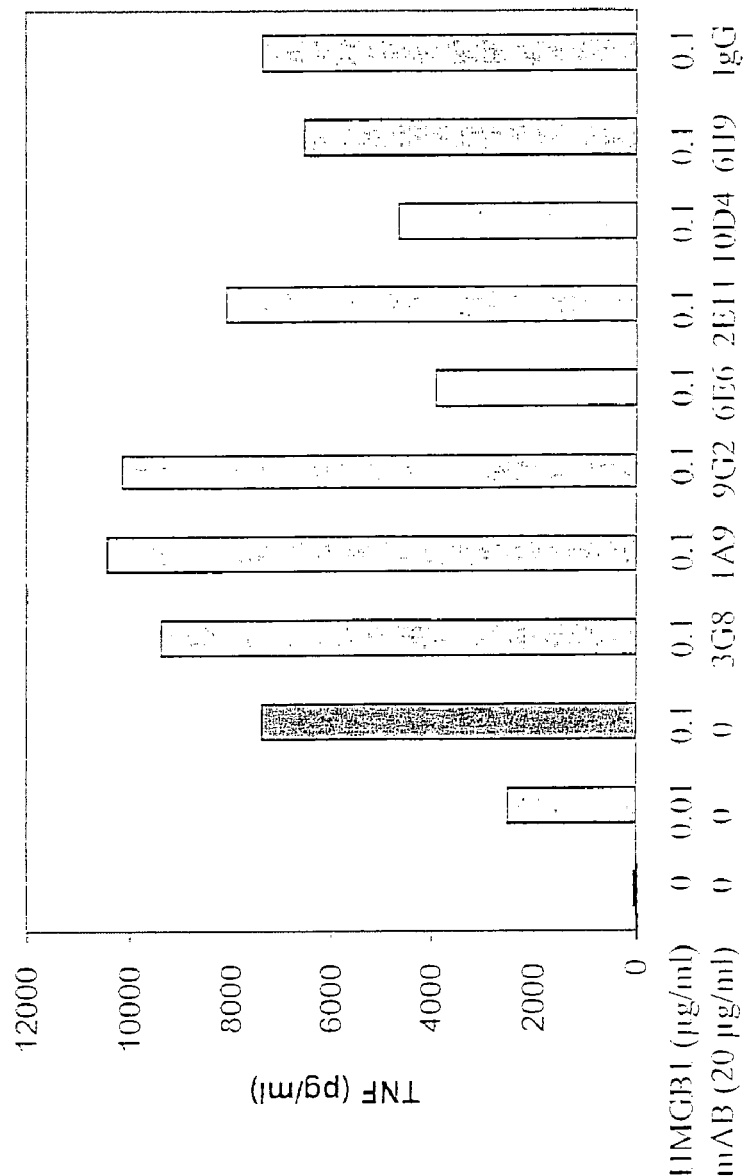
FIG. 9 is a histogram depicting inhibition of TNF release by various anti-HMGB1 monoclonal antibodies. Mouse TNF was induced by stimulating RAW 264.7 cells with 0.01 µg/ml or 0.1 µg/ml of recombinant CBP-Rat HMGB1 peptide (SEQ ID NO:5). Where indicated, 20 μg/ml of 3G8 HMGB1 mAb (3G8), 1A9 HMGB1 mAb (1A9), 9G2 HMGB1 mAb (9G2), 6E6 HMGB1 mAb (6E6), 2E11 HMGB1 mAb (2E11), 10D4 HMGB1 mAb (10D4), 6H9 HMGB1 mAb (6H9) or mouse IgG control antibody (IgG) were added.

The ability of particular HMGB1 monoclonal antibodies to inhibit TNF release was assessed. The results of this study are shown in FIGS. 8 and 9, which are histograms depicting TNF released by RAW 264.7 cells administered only HMGB1, HMGB1 plus particular HMGB1 monoclonal antibodies, or a control IgG antibody. FIG. 8 depicts the results of inhibition of HMGB1-mediated TNF release for 6E6 HMGB1 mAb, 10D4 HMGB1 mAb, 2E11 HMGB1 mAb, 9G2 HMGB1 mAb, and a control IgG antibody. FIG. 9 depicts the results of inhibition of HMGB1-mediated TNF release for 3G8 HMGB1 mAb, 1A9 HMGB1 mAb, 9G2 HMGB1 mAb, 6E6 HMGB1 mAb, 2E11 HMGB1 mAb, 10D4 HMGB1 mAb, 6H9 HMGB1 mAb, or a control IgG antibody. As depicted in FIGS. 8 and 9, particular HMGB1 monoclonal antibodies (e.g., 6E6 HMGB1 mAb, 10D4 HMGB1 mAb) inhibited TNF release, indicating that such antibodies could be used to modulate one or more HMGB functions (e.g., as described herein). For example, these blocking antibodies could be used to neutralize the biological activity of HMGB1 (e.g., HMGB1-mediated activation of the cytokine cascade).

EXAMPLE 6

Figure 10:
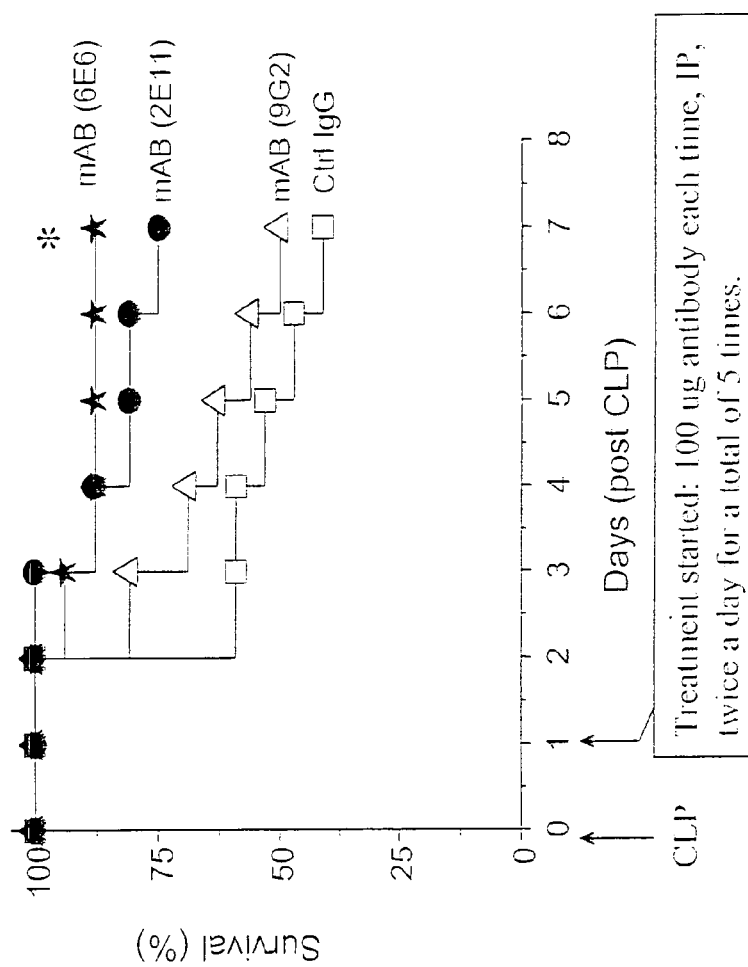
FIG. 10 is a graph of the effect of various anti-HMGB1 monoclonal antibodies (6E6 HMGB1 mAb (mAB (6E6)); 2E11 HMGB1 mAb (mAB (2E11)); 9G2 HMGB1 mAb (mAB (9G2))) and a control IgG antibody (Ctrl IgG) on survival of mice over time (days) after cecal ligation and puncture (CLP).

Treatment of Septic Mice with Anti-HMGB1 Monoclonal Antibodies Increases Survival of Mice Mice were subjected to cecal ligation and puncture (CLP), a well characterized model of sepsis caused by perforating a surgically-created cecal diverticulum, that leads to polymicrobial peritonitis and sepsis (Fink and Heard, supra; Wichmann et al., supra; and Remick et al., supra), and administered particular anti-HMGB1 monoclonal antibodies (6E6 HMGB1 mAb, 2E11 HMGB1 mAb or 9G2 HMGB1) or a control IgG antibody (100 µg of antibody administered twice per day). Survival was monitored for 7 days. The results of this study are shown in FIG. 10, which is a graph of the survival of septic mice treated with either a control antibody or particular anti-HMGB1 monoclonal antibodies. The results show that anti-HMGB1 monoclonal antibodies administered to the mice starting 24 hours after the onset of cecal perforation rescued animals from death, as compared to administration of an IgG control antibody. For 6E6 HMGB1 mAb, the rescue was significant at day 7 ($p<0.03$ versus control, Fisher's exact test).

A dose response curve for survival of septic mice treated with 6E6 HMGB1 mAb was also conducted. As depicted in FIG. 16, doses of 1, 10 and 100 µg of 6E6 HMGB1 mAb were administered to mice. The results demonstrate that a dose of 10 µg of 6E6 HMGB1 resulted in the greatest rescue of the septic mice.

EXAMPLE 7

Selectivity of Anti-HMGB1 Monoclonal Antibodies

As described above, western blot analysis was performed using particular anti-HMGB1 monoclonal antibodies. FIG. 11 depicts individual western blots of samples containing either CHO HMGB1 or CHO HMGB2 and possibly recombinant HMGB1-His$_6$ (labeled as CHO HMGB2, rec-HMGB1-His$_6$), which were probed with either an anti-His Tag antibody, an anti-HMGB2 antibody, an anti-HMGB1/2 monoclonal antibody, or particular anti-HMGB1 monoclonal antibodies (e.g., 2E11 HMGB1 mAb, 1G3 HMGB1 mAb, 6H9 HMGB1 mAb, 2G7 HMGB1 mAb, 2G5 HMGB1 mAb and 6E6 HMGB1 mAb). The results of these experiments reveal that 2G7 HMGB1 mAb binds HMGB1 but does not detectably bind HMGB2, while 2E11 HMGB1 mAb, 1G3 HMGB1 mAb and 6H9 HMGB1 mAb detect HMGB2 in addition to HMGB1.

EXAMPLE 8

HMGB1 Peptide Binding Experiments

Biotinylated peptides corresponding to particular 18 amino acid regions of human HMGB1 and a longer peptide corresponding to amino acid residues 9-85 of human HMGB1 were prepared and analyzed for binding to particular anti-HMGB1 monoclonal antibodies by ELISA. These peptides and their respective sequences are depicted in FIG. 13A.

The results of these peptide binding experiments are depicted in FIG. 13B. As depicted in FIG. 13B, 2E11 HMGB1 mAb bound to a peptide corresponding to amino acid residues 151-168 of human HMGB1 (i.e., amino acid residues 151-168 SEQ ID NO:1). 6E6 HMGB1 mAb and 6H9 bound to a peptide corresponding to amino acid residues 61-78 of human HMGB1 (i.e., amino acid residues 61-78 SEQ ID NO:1). 2G7 HMGB1 mAb bound to a peptide corresponding to amino acid residues 46-63 of human HMGB1 (i.e., amino acid residues 46-63 of SEQ ID NO:1). In addition, 2G7 HMGB1 mAb and 6E6 HMGB1 mAb also bound the longer peptide corresponding to amino acid residues 9-85 of human HMGB1. These experiments demonstrate that particular anti-HMGB1 monoclonal antibodies recognize different epitopes within the HMGB1 polypeptide. For example, 6E6 HMGB1 mAb, which was shown to inhibit HMGB1-mediated TNF release binds to an epitope contained within amino acids 61-78 of HMGB1. The discovery of a blocking epitope within this particular region of HMGB1 could be used to screen for additional blocking agents (e.g., agents that inhibit an HMGB1 function (e.g., HMGB1-mediated activation of the cytokine cascade)).

EXAMPLE 9

HMGB1 ELISA

Figure 14:
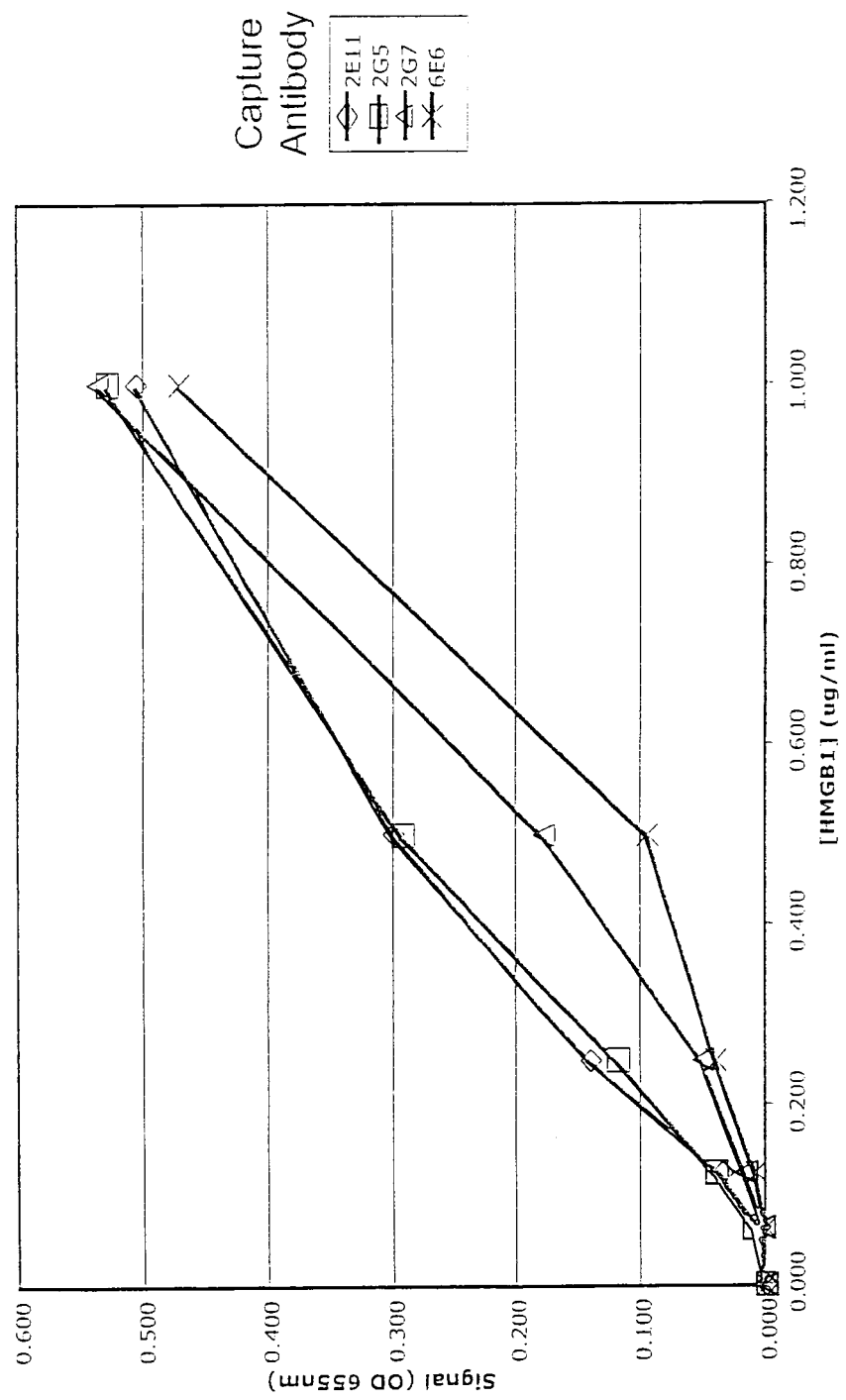
FIG. 14 is a graph depicting the results of anti-HMGB1 monoclonal antibody ELISAs. In the ELISAs, particular anti-HMGB1 monoclonal antibodies (2E11 HMGB1 mAb (2E11), 2G5 HMGB1 mAb (2G5), 2G7 HMGB1 mAb (2G7) and 6E6 HMGB1 mAb (6E6)) were used as capture antibodies and a polyclonal HMGB1 antibody was used as the detector antibody.
Figure 15:
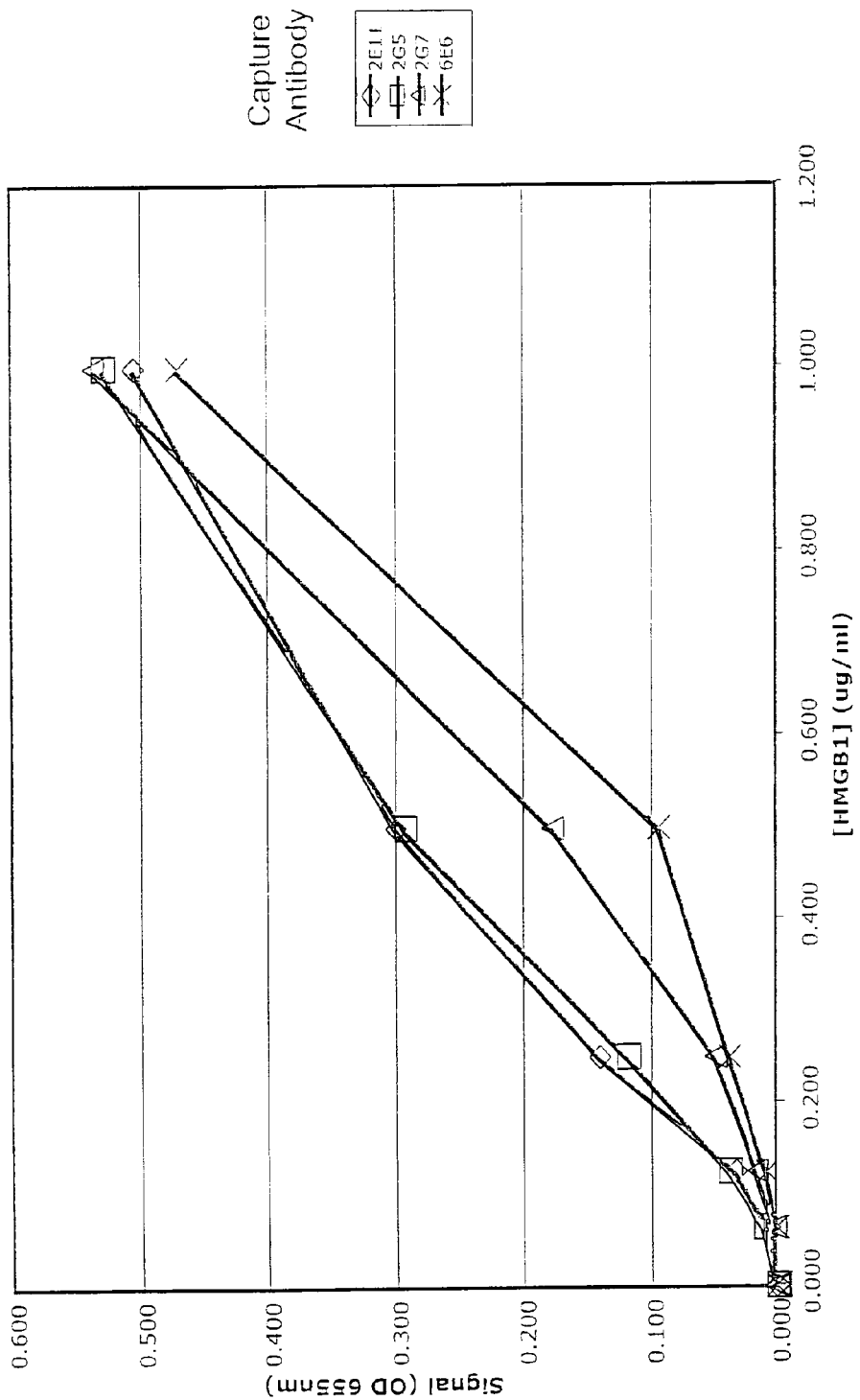
FIG. 15 is a graph depicting the results of anti-HMGB1 monoclonal antibody ELISAs. In the ELISAs, particular anti-HMGB1 monoclonal antibodies (2E11 HMGB1 mAb (2E11), 2G5 HMGB1 mAb (2G5), 2G7 HMGB1 mAb (2G7) and 6E6 HMGB1 mAb (6E6)) were used as capture antibodies and 6E6 HMGB1 mAb was used as the detector antibody.

As depicted in FIGS. 14 and 15, two different ELISA methods were used to examine the properties of particular anti-HMGB1 monoclonal antibodies. In one method, HMGB1 monoclonal antibodies 2E11 HMGB1 mAb, 2G5 HMGB1 mAb, 2G7 HMGB1 mAb, and 6E6 HMGB1 mAb, were used as capture antibodies and a polyclonal HMGB1 antibody was used as the detector antibody. In the other ELISA method, HMGB1 monoclonal antibodies 2E11 HMGB1 mAb, 2G5 HMGB1 mAb, 2G7 HMGB1 mAb, and 6E6 HMGB1 mAb, were used as capture antibodies and 6E6 HMGB1 mAb was used as the detector antibody. The results from both of the ELISA methods demonstrate that the monoclonal HMGB1 antibodies can detect HMGB1 and would be suitable for the diagnostic and/or prognostic methods described herein.

EXAMPLE 10

Binding of 2G7 HMGB1 mAb to HMGB1 is Inhibited by a Peptide Corresponding to Amino Acid Residues 46-63 of HMGB1

HMGB1 peptide binding experiments using 2G7 HMGB1 mAb were conducted. As described, biotinylated synthetic peptides corresponding to either amino acid residues 46-63 of human HMGB1 or amino acid residues 61-78 of human HMGB1 were prepared and analyzed for binding to 2G7 HMGB1 mAb (2G7) by ELISA. Briefly, 2 µg/ml of 2G7 HMGB1 mAb was added to plate wells containing either the HMGB1 46-63 peptide or the HMGB161-78 peptide at each of the indicated concentrations (0, 0.33, 1, 3, 9, 27, 81 and 243 µM peptide) for one hour at 25° C. to prepare antibody-peptide samples. ELISA plates were coated with 10 µg/ml of recombinant rat HMGB1, and incubated overnight at 4° C. The plates were then blocked with reconstituted milk for one hour at 37° C. Antibody-peptide samples were then added at the concentrations listed above and incubated for one hour at room temperature. The plates were then washed and incubated with Streptavidin-HRP. After washing, the plates were developed with TMB (Invitrogen, San Diego, Calif.) and absorbance at 655 nm was measured using a plate reader.

Figure 20:
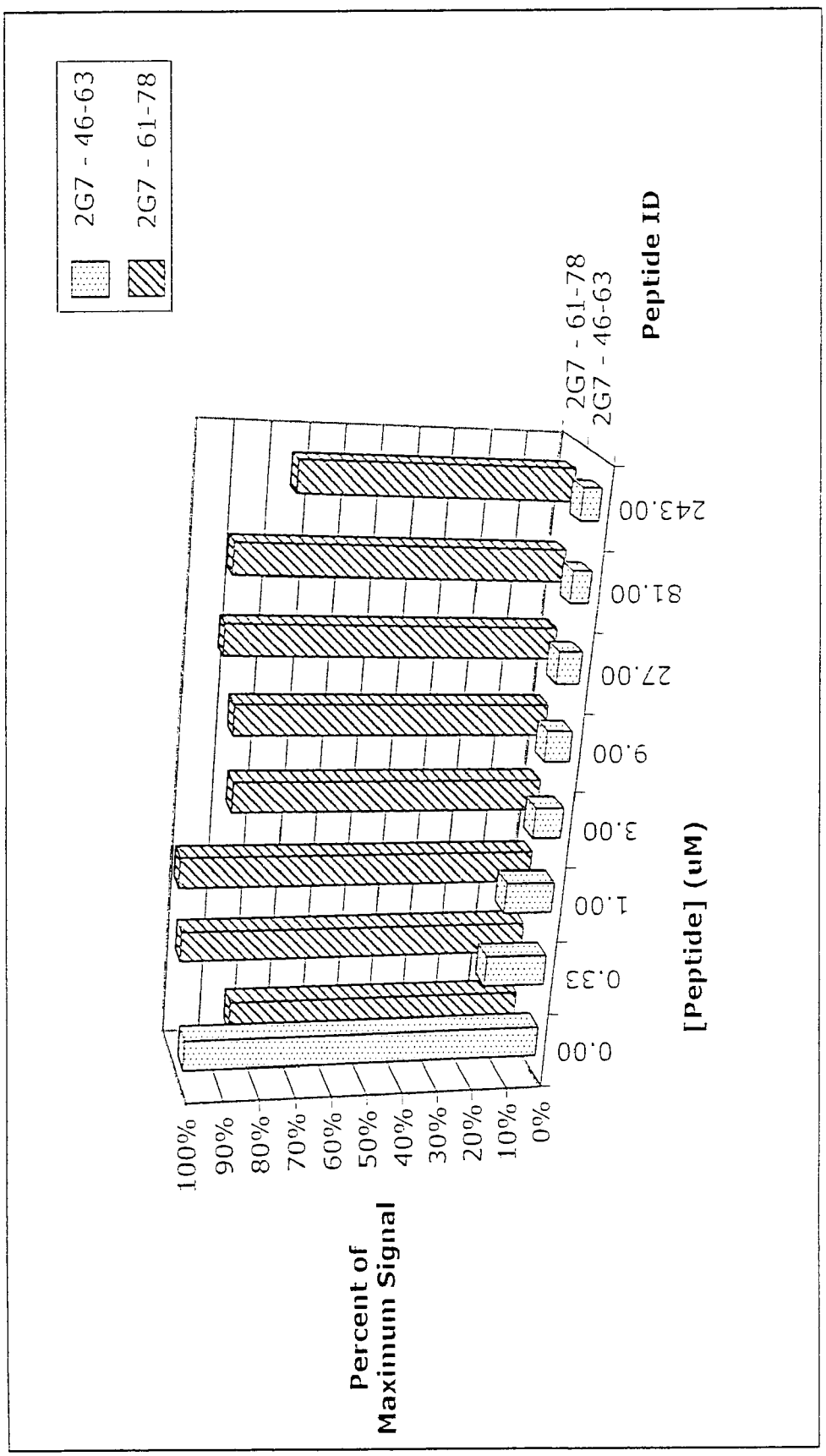
FIG. 20 is a histogram depicting the results of HMGB1 peptide binding experiments. Biotinylated peptides corresponding to either amino acid residues 46-63 or 61-78 of HMGB1 were prepared and analyzed for binding to 2G7 HMGB1 mAb (2G7) by ELISA.

FIG. 20 depicts the results as percent of maximum signal (y-axis). As FIG. 20 demonstrates, the HMGB1 46-63 peptide inhibited the binding of 2G7 HMGB1 mAb to bound HMGB1 at all concentrations (depicted as a decrease in % of maximum signal). In contrast, the HMGB1 61-78 peptide did not inhibit the binding of 2G7 HMGB1 mAb to HMGB1. These experiments further confirm that 2G7 HMGB1 mAb binds to an epitope that is present in amino acids 46-63 of HMGB1.

EXAMPLE 11

Binding of 2E11 HMGB1 mAb to HMGB1 is Inhibited by Higher Concentrations of a Peptide Corresponding to Amino Acid Residues 151-168 of HMGB1

Figure 21:
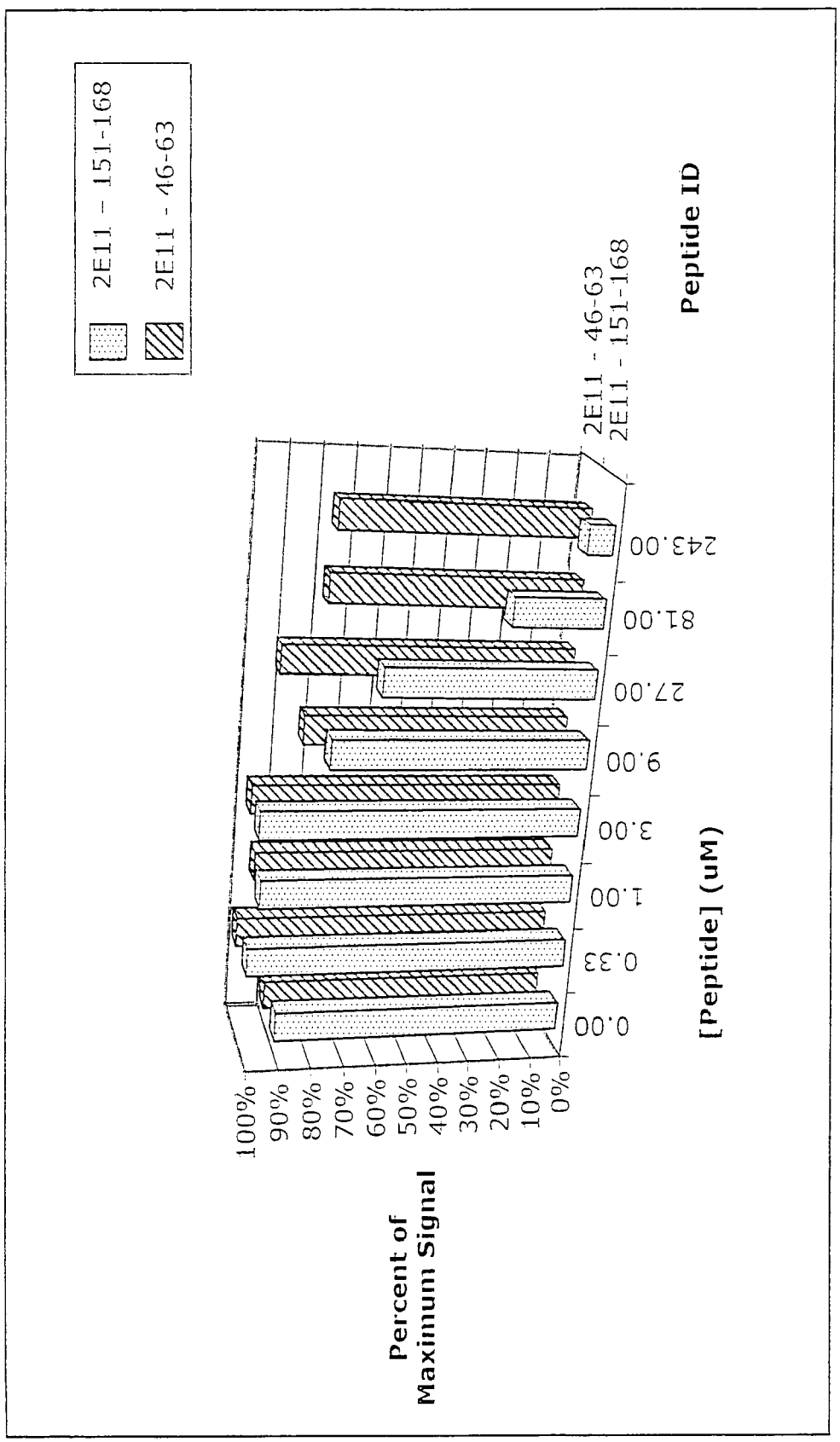
FIG. 21 is a histogram depicting the results of HMGB1 peptide binding experiments. Biotinylated peptides corresponding to either amino acid residues 46-63 or 151-168 of HMGB1 were prepared and analyzed for binding to 2E11 HMGB1 mAb (2E11) by ELISA.

HMGB1 peptide binding experiments using 2E11 HMGB1 mAb and biotinylated synthetic peptides corresponding to either amino acid residues 46-63 of human HMGB1 (SEQ ID NO:23) or amino acid residues 151-168 of human HMGB1 (SEQ ID NO:30) were conducted as described herein The results of these experiments are depicted in FIG. 21 (as percent of maximum signal (y-axis)). As FIG. 21 demonstrates, the HMGB1 151-168 peptide significantly inhibited the binding of 2E11 HMGB1 mAb to bound HMGB1 at concentrations of 9 µM or greater. The HMGB1 151-168 peptide did not significantly inhibit the binding of 2E11 HMGB1 mAb to HMGB1 at concentrations of 3 µM or below (FIG. 21). In addition, the HMGB1 46-63 peptide did not inhibit the binding of 2E11 HMGB1 mAb to HMGB1. These experiments confirm that 2E11 HMGB1 mAb binds to an epitope that is present in amino acids 151-168 of HMGB1.

EXAMPLE 12

2G7 HMGB1 mAb Recognizes an Epitope that is Present in Amino Acids 53-63 of HMGB1

Various synthetic peptides were prepared. These synthetic peptides included a biotinylated peptide corresponding to amino acid residues 46-63 of human HMGB1 (SEQ ID NO:23; designated "huHMGB1-46-63-B" or "Human HMGB1-46-63-B"), a biotinylated peptide corresponding to amino acid residues 46-63 of human HMGB2 (SEQ ID NO:48; designated "huHMGB2-46-63-B" or "Human HMGB2-46-63-B"), a non-biotinylated peptide corresponding to amino acid residues 53-70 of human HMGB1 (SEQ ID NO:47; designated "huHMGB1-53-70" or "Human HMGB1-53-70"), a biotinylated peptide corresponding to amino acid residues 61-78 of human HMGB1 (SEQ ID NO:24; designated "huHMGB1-61-78-B"), a non-biotinylated peptide corresponding to amino acid residues 40-57 of human HMGB1 (SEQ ID NO:46; designated "Human HMGB1-40-57") and a non-biotinylated peptide consisting of a scrambled amino acid sequence, wherein the amino acid residues that were scrambled were those of amino acid residues 46-63 of human HMGB1 (SEQ ID NO:45; designated "Human HMGB1-46-63-scr"). By ELISA, as described herein, the binding of 2G7 HMGB1 mAb to these overlapping peptides was analyzed to more specifically ascertain the epitope within HMGB1 that binds to 2G7 HMGB1 mAb. These peptides and their respective sequences are depicted in FIG. 23.

Figure 22:
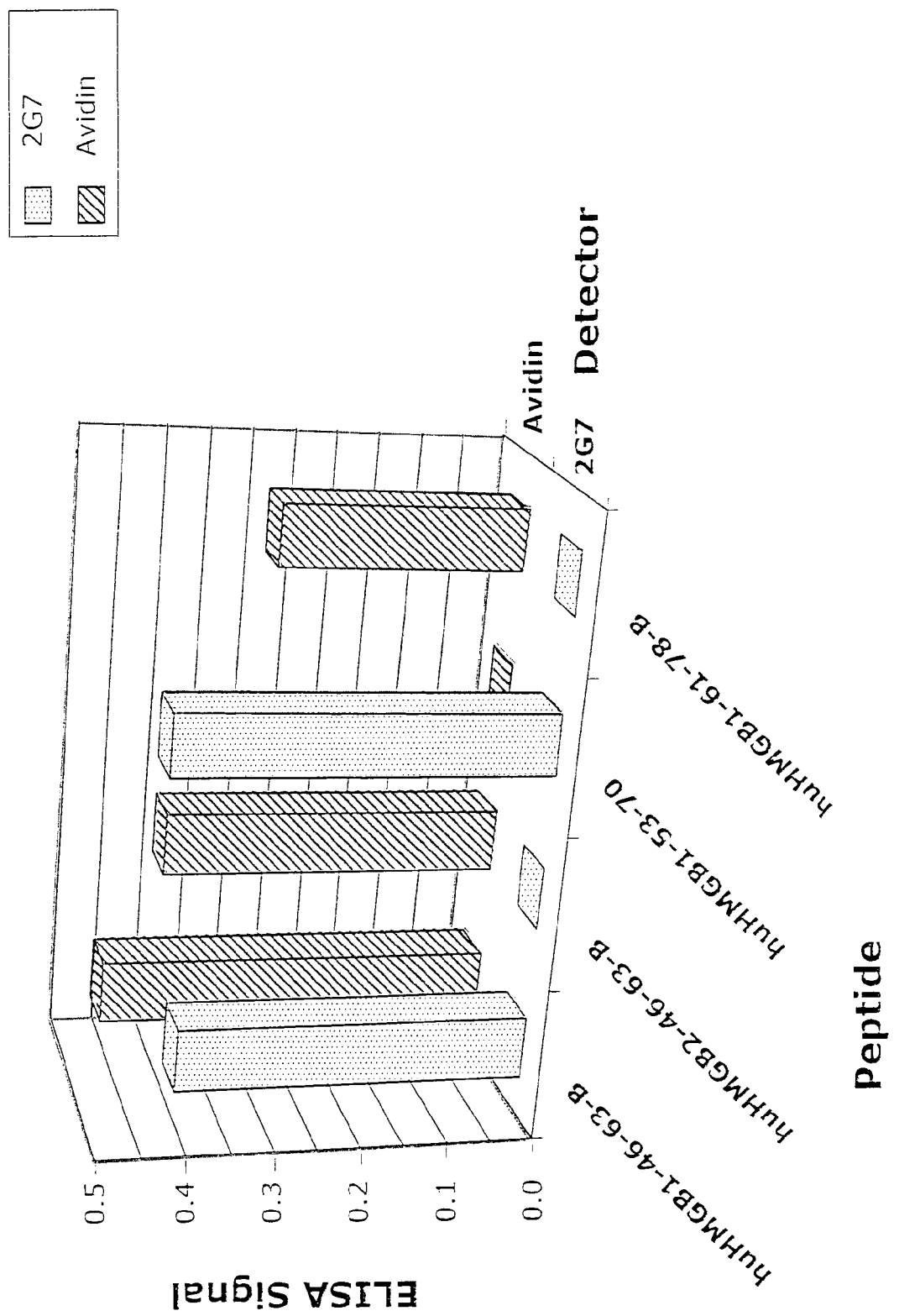
FIG. 22 is a histogram depicting the results of HMGB1 and HMGB2 peptide binding experiments. Peptides corresponding to either amino acid residues 46-63 of human HMGB1 (labeled "huHMGB1-46-63-B"), amino acid residues 46-63 of human HMGB2 (labeled "huHMGB2-46-63-B"), amino acid residues 53-70 of human HMGB1 (labeled "huHMGB1-53-70"), or amino acid residues 61-78 of human HMGB1 (labeled "huHMGB1-61-78-B") were prepared and analyzed for binding to 2G7 HMGB1 mAb (2G7) or avidin by ELISA.

The results of the peptide binding experiments are depicted in FIGS. 22 and 23. As shown in FIGS. 22 and 23, 2G7 HMGB1 mAb bound to the HMGB1 46-63 peptide (i.e., amino acid residues 46-63 of SEQ ID NO:1 or SEQ ID NO:23) but did not bind to the corresponding amino acid region of human HMGB2 (i.e., the HMGB2 46-63 peptide; amino acid residues 46-63 of SEQ ID NO:54 or SEQ ID NO:48). In addition, 2G7 HMGB1 mAb bound to the HMGB1 53-70 peptide but did not bind the HMGB1 40-57 peptide. 2G7 HMGB1 mAb also did not bind to the peptide consisting of a scrambled sequence of amino acid residues 46-63 of HMGB1. In addition to showing the binding of 2G7 HMGB1 mAb to the various synthetic peptides, FIG. 22 also depicts the binding of avidin to these synthetic peptides.

In Example 8, it was shown that 2G7 HMGB1 mAb binds to an epitope contained within amino acid residues 46-63 of HMGB1. Given that 2G7 HMGB1 mAb binds the HMGB1 46-63 peptide and the HMGB1 53-70 peptide, these experiments demonstrate that 2G7 HMGB1 mAb recognizes an epitope present in the amino acid region consisting of amino acid residues 53-63 of HMGB1. These experiments further demonstrate that 2G7 HMGB1 mAb does not bind to the HMGB2 46-63 peptide, notwithstanding only a single amino acid difference between the HMGB1 46-63 peptide and the HMGB2 46-63 peptide. As such, the glycine residue at position 58 of HMGB1 (Gly-58), which is a corresponding serine residue in HMGB2, is an important amino acid residue in the HMGB1 epitope recognized by 2G7 HMGB1 mAb (FIG. 23).

EXAMPLE 13

6E6 HMGB1 mAb Recognizes an Epitope that is Present in Amino Acids 67-78 of HMGB1

Various synthetic peptides were prepared. These synthetic peptides included a non-biotinylated peptide corresponding to amino acid residues 53-70 of human HMGB1 (SEQ ID NO:47; designated "Human HMGB1-53-70-B"; described above), a non-biotinylated peptide corresponding to amino acid residues 67-84 of human HMGB1 (SEQ ID NO:50; designated "Human HMGB1-67-84"), a biotinylated peptide corresponding to amino acid residues 61-78 of human HMGB1 (SEQ ID NO:24 designated "Human HMGB1-61-78-B") and a non-biotinylated peptide consisting of a scrambled amino acid sequence, wherein the amino acid residues that were scrambled were those of amino acid residues 61-78 of human HMGB1 (SEQ ID NO:49; designated "Human HMGB1-61-78_scr"). By ELISA, as described herein, the binding of 6E6 HMGB1 mAb to these overlapping peptides was analyzed to more specifically ascertain the epitope within HMGB1 that binds to 6E6 HMGB1 mAb. These peptides, their respective sequences and which of the peptides were bound by 6E6 HMGB1 mAb are depicted in FIG. 24.

The results of these peptide binding experiments are depicted in FIG. 24. As shown in FIG. 24, 6E6 HMGB1 mAb bound to the HMGB1 61-78 peptide (SEQ ID NO:24). Further, 6E6 HMGB1 mAb bound to the HMGB1 67-84 peptide (SEQ ID NO:50) but did not bind to the HMGB1 53-70 peptide (SEQ ID NO:47) (FIG. 24). 6E6 HMGB1 mAb also did not bind to the peptide consisting of a scrambled sequence of amino acid residues 61-78 of HMGB1 (SEQ ID NO:49) (FIG. 24). In Example 8, it was shown that 6E6 HMGB1 mAb binds to an epitope contained within amino acid residues 61-78 of HMGB1. Given that 6E6 HMGB1 mAb binds to the HMGB1 61-78 peptide and the HMGB1 67-84 peptide, these experiments demonstrate that 6E6 HMGB1 mAb recognizes an epitope present in the amino acid region consisting of amino acid residues 67-78 of HMGB1.

EXAMPLE 14

HMGB1 Peptide Binding Experiments with 2E11 HMGB1 mAb

Various synthetic peptides were prepared. These synthetic peptides included a biotinylated peptide corresponding to amino acid residues 151-168 of human HMGB1 (SEQ ID NO:30; designated "Human HMGB1-151-168-B"), a non-biotinylated peptide corresponding to amino acid residues 143-160 of human HMGB1 (SEQ ID NO:52; designated "Human HMGB1-143-160"), a non-biotinylated peptide corresponding to amino acid residues 157-174 of human HMGB1 (SEQ ID NO:53; designated "Human HMGB1-157-174"), and a non-biotinylated peptide corresponding to a scrambled amino acid sequence, wherein the amino acid residues that were scrambled were those of amino acid residues 151-168 of human HMGB1 (SEQ ID NO:51; designated "Human HMGB1-151-168_scr"). By ELISA, as described herein, the binding of 2E11 HMGB1 mAb to these overlapping peptides was analyzed to more specifically ascertain the epitope within HMGB1 that binds to 2E11 HMGB1 mAb. These peptides, their respective sequences and which of the peptides were bound by 2E11 HMGB1 mAb are depicted in FIG. 25.

As depicted in FIG. 25, 2E11 HMGB1 mAb bound to the HMGB1 151-168 peptide (SEQ ID NO:30), but did not bind to either the HMGB1 143-160 peptide (SEQ ID NO:52) or the HMGB1 157-174 peptide (SEQ ID NO:53). As is known in the art, there are two types of epitopes or antigenic determinants: linear, sequential or continuous epitopes and non-linear, conformational or discontinuous epitopes. The dimensions of a typical antibody epitope are often given as 6 amino acid residues in size, but can be of variable size. These experiments suggest that the epitope recognized by 2E11 HMGB1 mAb is likely to comprise amino acid residues 156-161 of HMGB1. However, 2E11 HMGB1 mAb may also recognize an epitope that includes flanking amino acids to this region, e.g., amino acid residues 155-161, 155-162, 156-162 and/or 156-163 of HMGB1.

Figure 26:
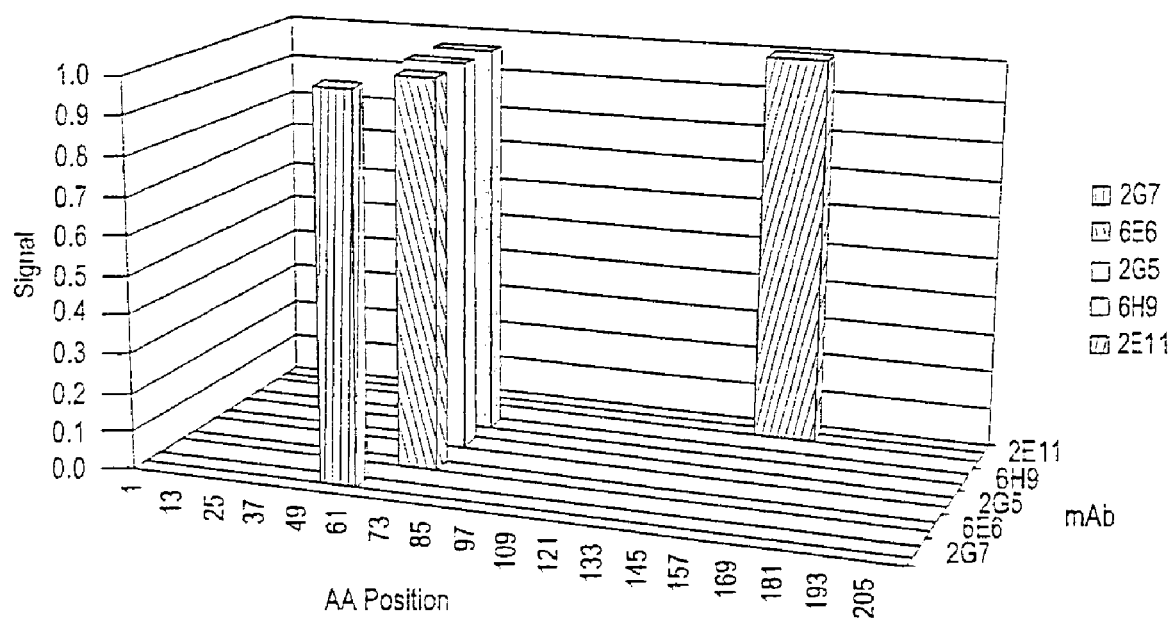
FIG. 26 is a histogram summarizing the results of peptide binding experiments and depicting the mapped epitopes of HMGB1 that are recognized by 2G7 HMGB1 mAb (2G7), 6E6 HMGB1 mAb (6E6), 2G5 HMGB1 mAb (2G5), 6H9 HMGB1 mAb (6H9) and 2E11 HMGB1 mAb (2E11).
Figure 27A:
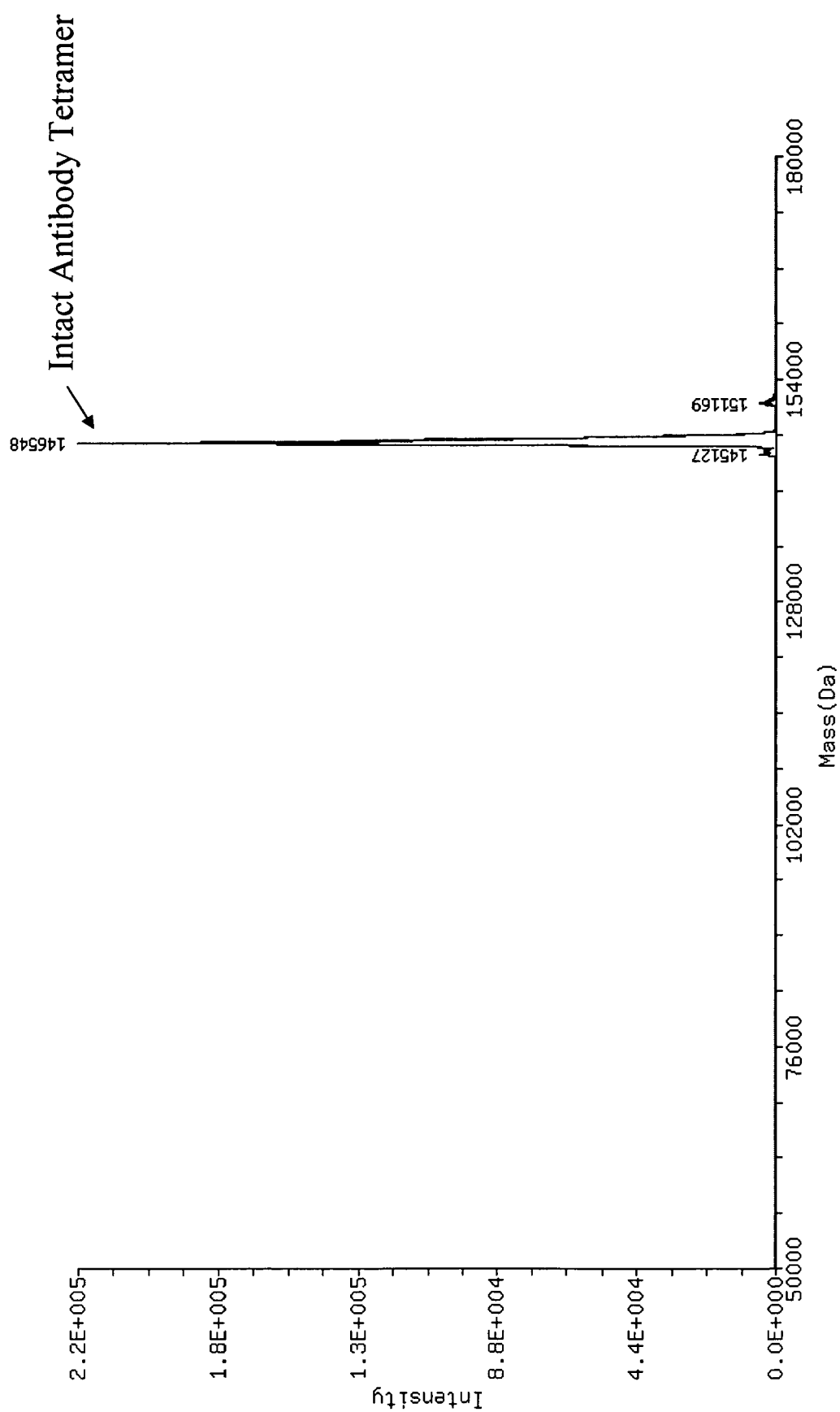
FIG. 27A is a mass spectrum of intact, non-reduced 6E6 HMGB1 mAb.
Figure 27B:
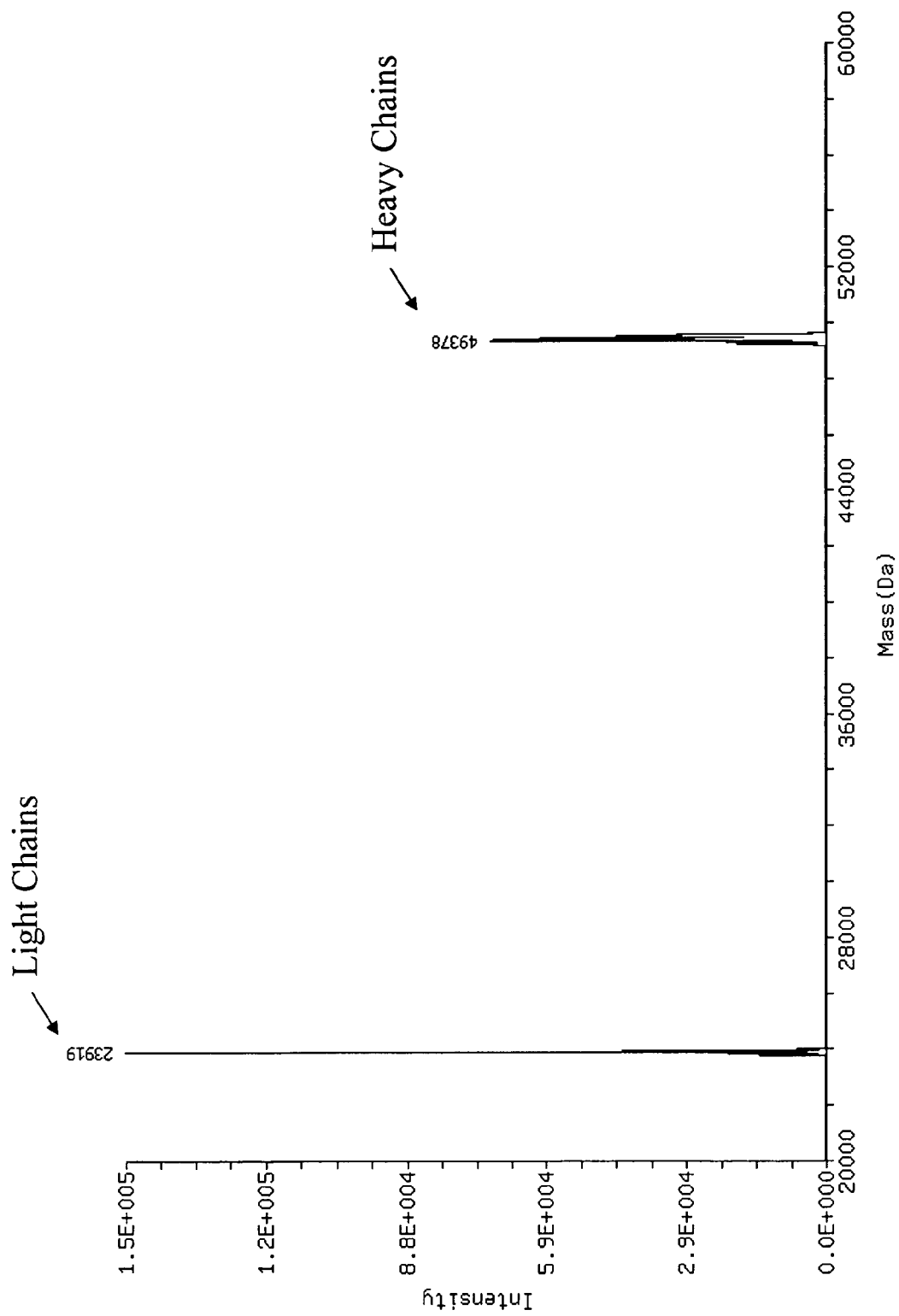
FIG. 27B is a mass spectrum of 6E6 HMGB1 mAb, which was reduced by treatment with DTT.
Figure 27C:
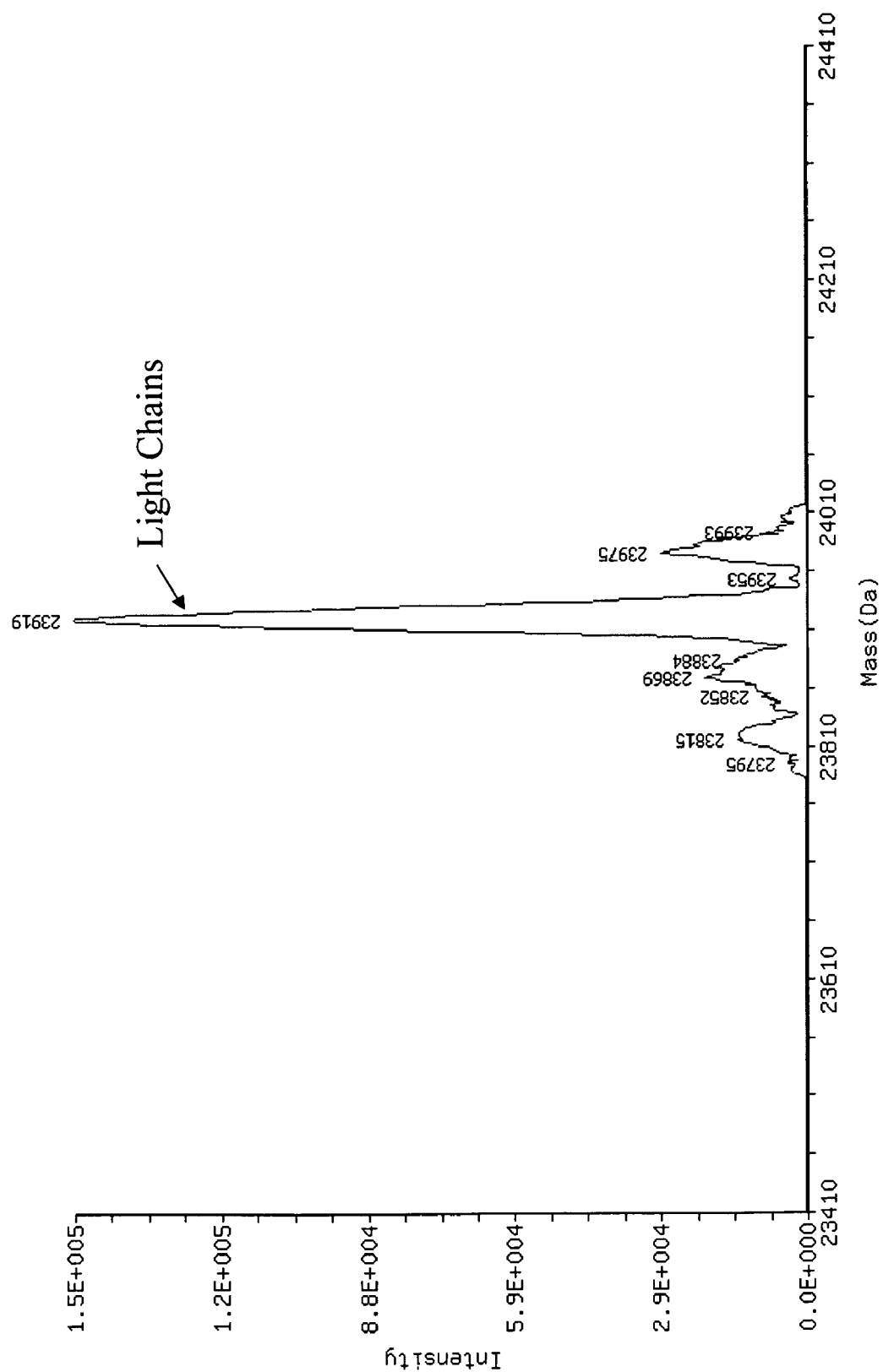
FIG. 27C is a mass spectrum of the light chains of 6E6 HMGB1 mAb, which were reduced by treatment with DTT.
Figure 27D:
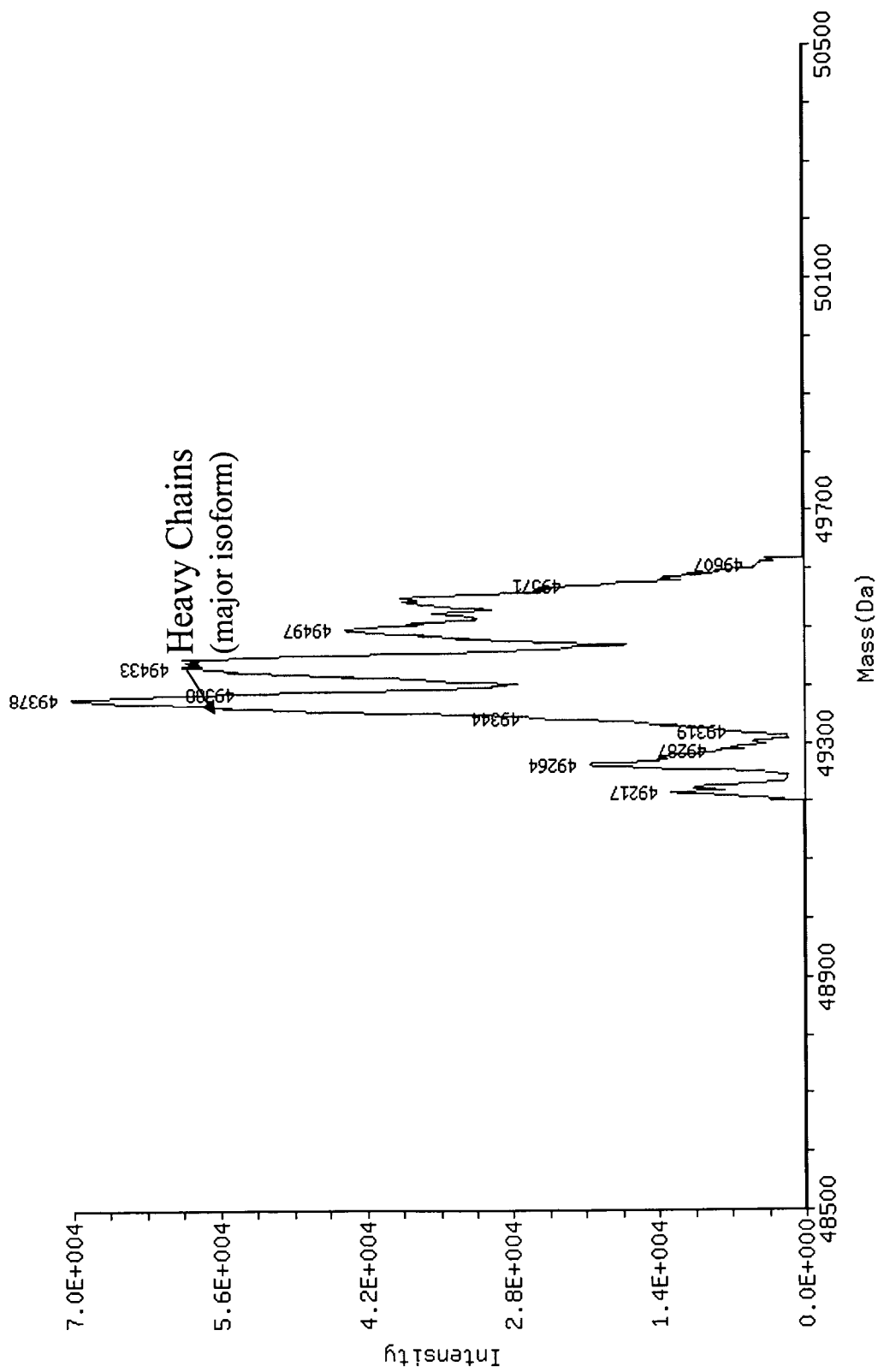
FIG. 27D is a mass spectrum of the heavy chains of 6E6 HMGB1 mAb, which were reduced by treatment with DTT.

A summary of the peptide binding results depicting the mapped epitopes of HMGB1 that are recognized by various HMGB1 mAbs (e.g., 2G7 HMGB1 mAb, 6E6 HMGB1 mAb, 2G5 HMGB1 mAb, 6H9 HMGB1 mAb, 2E11 HMGB1 mAb) is shown in FIG. 26.

EXAMPLE 15

Mass Spectrometry of 6E6 HMGB1 mAb

The mass of 6E6 HMGB1 mAb was determined by mass spectrometry. 6E6 HMGB1 mAb was sent to Novatia, LLC (Princeton, N.J.) for LC/MS analysis. Briefly, the antibody, either intact or after being treated with DTT (to separate heavy and light chains), was subjected to analysis using a PLRP-s 4000A reverse phase HPLC column (HPLC/ESI-MS system) and mass spectroscopy (Finnigan TSQ7000 mass spectrometer). Mass accuracy for proteins is generally ±0.01%, and this accuracy was achieved in measuring the mass of the 6E6 light chain (e.g., 2 Da/23,917 Da×100%=0.008%).

The results of this analysis are shown in FIGS. 27A-27D, which depicts a mass spectrum plot. The total mass of 6E6 HMGB1 mAb was 146.5 kDa (FIG. 27A; depicting mass spectrum for intact 6E6 HMGB1 mAb). The masses of the light and heavy chains of 6E6 HMGB1 mAb were determined to be 23.9 kDa (FIGS. 27B and 27C) and 49.4 kDa (FIGS. 27B and 27D), respectively. The predicted masses for the light and heavy chains, as calculated using amino acid molecular weights, are 23.9 kDa and 47.9 kDa, respectively.

EXAMPLE 16

Figure 28:
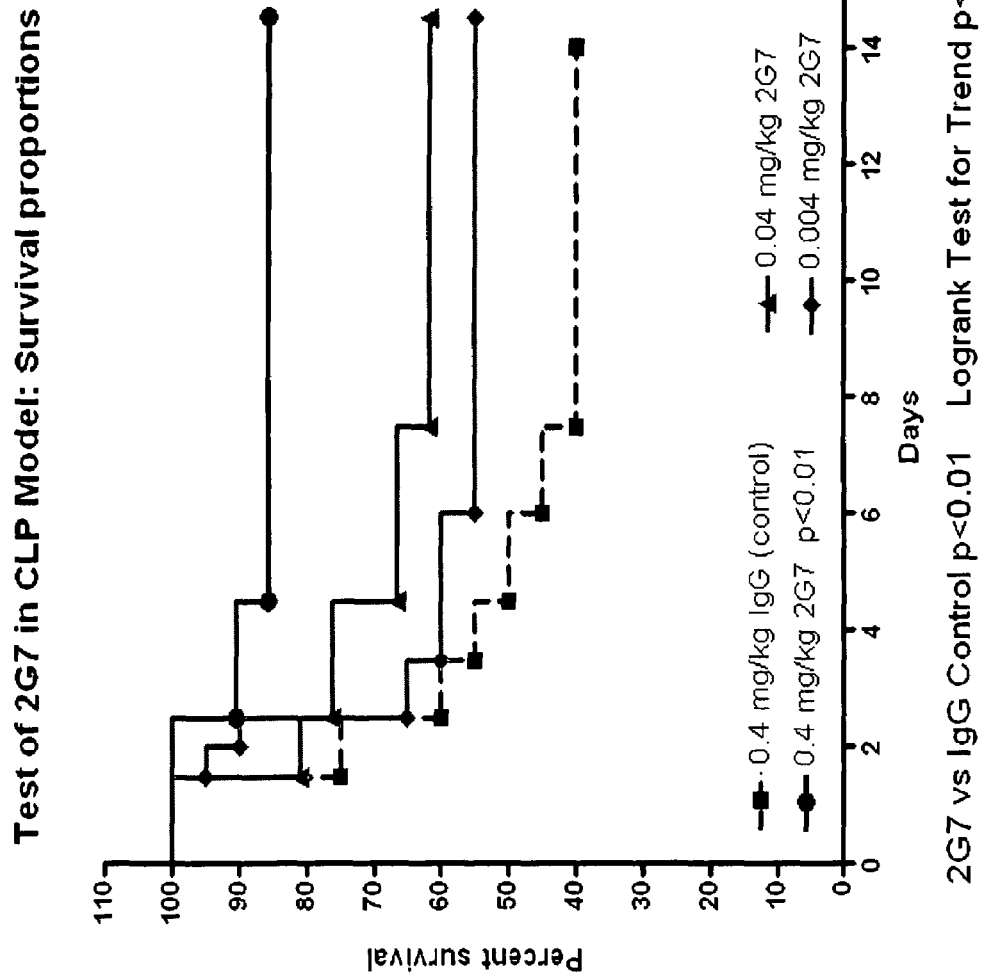
FIG. 28 is a graph of the effect of administration of various doses (either 0.004 mg/kg, 0.04 mg/kg or 0.4 mg/kg) of 2G7 HMGB1 mAb or a control IgG antibody (0.4 mg/kg) on survival of mice over time (days) after cecal ligation and puncture (CLP).

2G7 HMGB1 mAb Increases Survival in Septic Mice after Administration of a Single Dose Mice were subjected to cecal ligation and puncture (CLP) as described above. In one experiment, twenty-four hours after surgery, mice were intraperitoneally administered either 0.004 mg/kg, 0.04 mg/kg or 0.4 mg/kg of 2G7 HMGB1 mAb (2G7) once per day. In a second experiment, twenty-four hours after surgery, mice were administered either 0.04 mg/kg of 2G7 HMGB1 mAb or 0.4 mg/kg of control IgG (IgG control) once per day. Survival was monitored for 14 days for both experiments. The results of the two experiments are combined and presented in FIG. 28. Administration of 0.4 mg/kg of 2G7 HMGB1 mAb resulted in approximately 85% survival at 14 days after CLP, as compared to approximately only 40% survival of mice administered with IgG control at 14 days after CLP (FIG. 28). Further, as depicted in FIG. 28, administration of 0.04 mg/kg and 0.004 mg/kg of 2G7 HMGB1 mAb resulted in approximately 60% and 50% survival at 14 days after CLP, respectively.

FIG. 29 is a table comparing CLP survival percentages in mice administered various doses (either 4 mg/kg, 0.4 mg/kg, 0.04 mg/kg or 0.004 mg/kg) of 6E6 HMGB1 mAb, 2G7 HMGB1 mAb or control IgG. As depicted in FIG. 29, the mice were administered the antibodies 4 times a day intraperitoneally. The results demonstrate that administration of a dose of 0.4 mg/kg of either 6E6 HMGB1 mAb or 2G7 HMGB1 mAb resulted in greater than 80% of the septic mice surviving to 14 days post-CLP, as compared to only approximately 40% of the septic mice surviving to 14 days post-CLP when administered control IgG.

EXAMPLE 17

Inhibition of TNF Release by Anti-HMGB1 Monoclonal Antibodies

Figure 32:
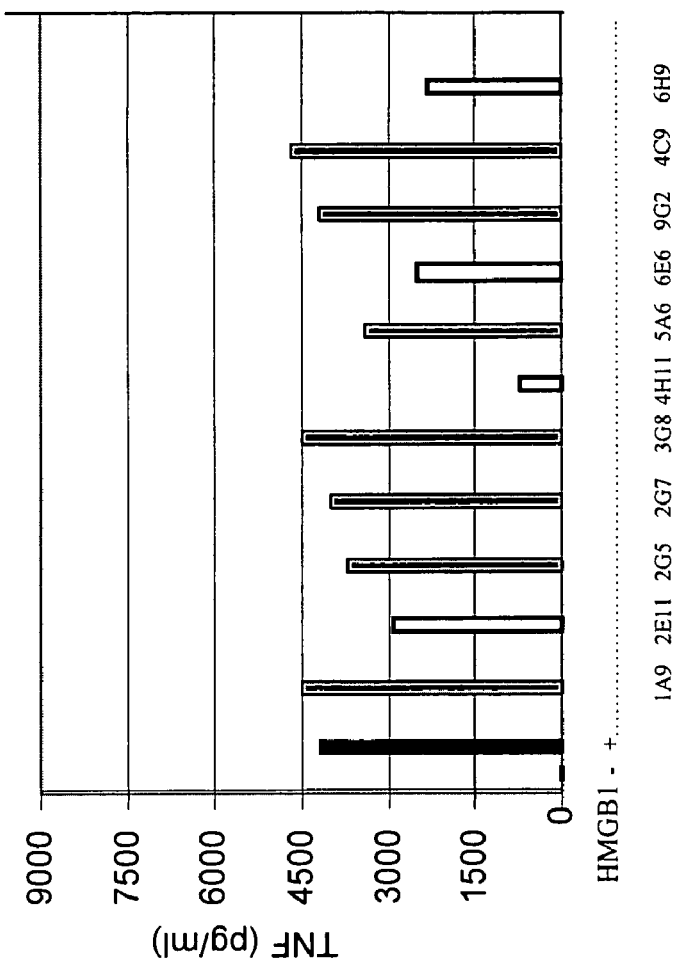
FIG. 32 is a histogram depicting inhibition of TNF release by various anti-HMGB1 monoclonal antibodies. Mouse TNF was induced by stimulating RAW 264.7 cells with 0.1 µg/ml of recombinant CBP-Rat HMGB1 peptide (SEQ ID NO:5). Where indicated, various HMGB1 monoclonal antibodies (cultured supernatants) were added to give a final concentration of 13%. The following antibodies were tested: 1A9 HMGB1 mAb (1A9); 2E11 HMGB1 mAb (2E11); 2G5 HMGB1 mAb (2G5); 2G7 HMGB1 mAb (2G7); 3G8 HMGB1 mAb (3G8); 4H11 HMGB1 mAb (4H11); 3-5A6 HMGB1 mAb (5A6); 6E6 HMGB1 mAb (6E6); 9G2 HMGB1 mAb (9G2); 4C9 HMGB1 mAb (4C9); and 6H9 HMGB1 mAb (6H9). The initial dark bar depicts TNF release in the absence of any antibodies.
Figure 33:
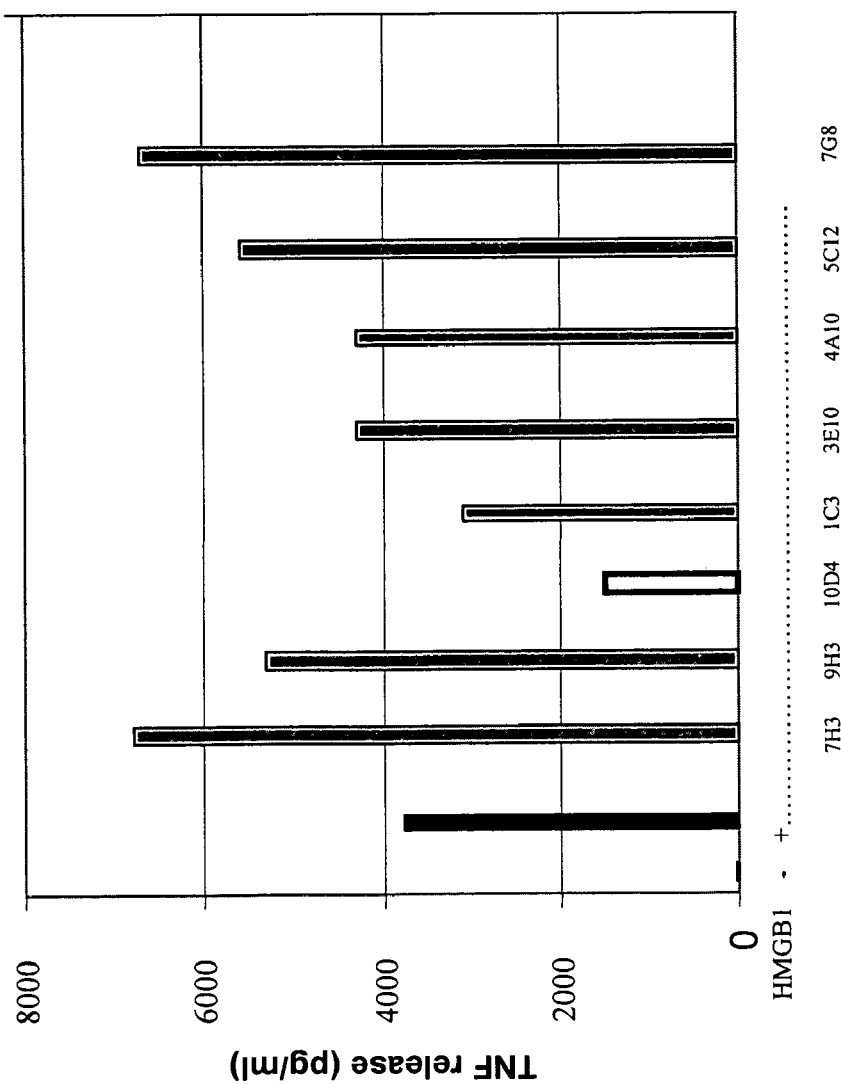
FIG. 33 is a histogram depicting inhibition of TNF release by various anti-HMGB1 monoclonal antibodies. Mouse TNF was induced by stimulating RAW 264.7 cells with 0.1 µg/ml of recombinant CBP-Rat HMGB1 peptide (SEQ ID NO:5). Where indicated, various HMGB1 monoclonal antibodies (cultured supernatants) were added to give a final concentration of 13%. The following antibodies were tested: 7H3 HMGB1 mAb (7H3); 9H3 HMGB1 mAb (9H3); 10D4 HMGB1 mAb (10D4); 1C3 HMGB1 mAb (1C3); 3E10 HMGB1 mAb (3E10); 4A10 HMGB1 mAb (4A10); 5C12 HMGB1 mAb (5C12); and 7G8 HMGB1 mAb (7G8). The initial dark bar depicts TNF release in the absence of any antibodies.

As in Example 5, the ability of particular HMGB1 monoclonal antibodies to inhibit TNF release was assessed. The results of this study are shown in FIGS. 32 and 33, which are histograms depicting TNF released by RAW 264.7 cells administered only HMGB1 (dark bar), or HMGB1 plus particular HMGB1 monoclonal antibodies. FIG. 32 depicts the results of inhibition of HMGB1-mediated TNF release for 1A9 HMGB1 mAb (1A9); 2E11 HMGB1 mAb (2E11); 2G5 HMGB1 mAb (2G5); 2G7 HMGB1 mAb (2G7); 3G8 HMGB1 mAb (3G8); 4H11 HMGB1 mAb (4H11; 5A6 HMGB1 mAb (5A6); 6E6 HMGB1 mAb (6E6); 9G2 HMGB1 mAb (9G2); 4C9 HMGB1 mAb (4C9); and 6H9 HMGB1 mAb (6H9). FIG. 33 depicts the results of inhibition of HMGB1-mediated TNF release for 7H3 HMGB1 mAb (7H3); 9H3 HMGB1 mAb (9H3); 10D4 HMGB1 mAb (10D4); 1C3 HMGB1 mAb (1C3); 3E10 HMGB1 mAb (3E10); 4A10 HMGB1 mAb (4A10); 5C12 HMGB1 mAb (5C12); and 7G8 HMGB1 mAb (7G8).

As depicted in FIGS. 32 and 33, and further to the results described in Example 5, particular HMGB1 monoclonal antibodies (e.g., 2E111 HMGB1 mAb, 4H11 HMGB1 mAb, 6E6 HMGB1 mAb, 6H9 HMGB1 mAb and 10D4 HMGB1 mAb) inhibited TNF release, indicating that such antibodies could be used to modulate one or more HMGB functions (e.g., as described herein). For example, these blocking antibodies could be used to neutralize the biological activity of HMGB1 (e.g., HMGB1-mediated activation of the cytokine cascade).

While this invention has been particularly shown and described with references to preferred embodiments thereof, it will be understood by those skilled in the art that various changes in form and details may be made therein without departing from the scope of the invention encompassed by the appended claims.

What is claimed is:

1. An antibody produced by a murine hybridoma deposited as ATCC Accession Number PTA-5433, or an antigen-binding fragment thereof.

2. A murine hybridoma deposited as ATCC Accession Number PTA-5433.

3. An isolated cell that produces the 6E6 HMGB1 monoclonal antibody (mAb) produced by the murine hybridoma deposited as ATCC Accession Number PTA-5433.

4. The isolated cell of claim 3, wherein said isolated cell is selected from the group consisting of an immortalized B cell, a hybridoma and a recombinant cell comprising one or more exogenous nucleic acid molecules that encode said antibody or antigen-binding fragment of said antibody.

5. An antibody or antigen-binding fragment thereof wherein said antibody or fragment comprises the light chain CDRs (CDR1, CDR2 and CDR3) and the heavy chain CDRs (CDR1, CDR2 and CDR3) of the 6E6 HMGB1 monoclonal antibody (mAb) produced by the murine hybridoma deposited as ATCC Accession Number PTA-5433.

6. The antibody or antigen-binding fragment of claim 5 wherein said antibody or antigen-binding fragment further comprises a human framework region.

7. A test kit for use in detecting the presence of a human high mobility group box 1 (HMGB1) polypeptide or a portion thereof that comprises residues 67-78 of SEQ ID NO:1, in a sample comprising:
   a) an antibody or antigen-binding fragment thereof wherein said antibody or fragment comprises the light chain CDRs (CDR1, CDR2 and CDR3) and the heavy chain CDRs (CDR1, CDR2 and CDR3) of the 6E6 HMGB1 monoclonal antibody (mAb) produced by the murine hybridoma deposited as ATCC Accession Number PTA-5433; and
   b) one or more ancillary reagents suitable for detecting the presence of a complex between said antibody or antigen-binding fragment and said HMGB1 polypeptide or said portion thereof.

* * * * *

SEQUENCE LISTING

```
<160> NUMBER OF SEQ ID NOS: 76

<210> SEQ ID NO 1
<211> LENGTH: 216
<212> TYPE: PRT
<213> ORGANISM: Homo sapiens

<400> SEQUENCE: 1

Met Gly Lys Gly Asp Pro Lys Lys Pro Thr Gly Lys Met Ser Ser Tyr
1               5                   10                  15
```

```
Ala Phe Phe Val Gln Thr Cys Arg Glu Glu His Lys Lys Lys His Pro
 20                  25                  30
Asp Ala Ser Val Asn Phe Ser Glu Phe Ser Lys Lys Cys Ser Glu Arg
 35                  40                  45
Trp Lys Thr Met Ser Ala Lys Glu Lys Gly Lys Phe Glu Asp Met Ala
 50                  55                  60
Lys Ala Asp Lys Ala Arg Tyr Glu Arg Glu Met Lys Thr Tyr Ile Pro
 65                  70                  75                  80
Pro Lys Gly Glu Thr Lys Lys Phe Lys Asp Pro Asn Ala Pro Lys
 85                  90                  95
Arg Leu Pro Ser Ala Phe Phe Leu Phe Cys Ser Glu Tyr Arg Pro Lys
100                 105                 110
Ile Lys Gly Glu His Pro Gly Leu Ser Ile Gly Asp Val Ala Lys Lys
115                 120                 125
Leu Gly Glu Met Trp Asn Asn Thr Ala Ala Asp Asp Lys Gln Pro Tyr
130                 135                 140
Glu Lys Lys Ala Ala Lys Leu Lys Glu Lys Tyr Glu Lys Asp Ile Ala
145                 150                 155                 160
Ala Tyr Arg Ala Lys Gly Lys Pro Asp Ala Ala Lys Lys Gly Val Val
165                 170                 175
Lys Ala Glu Lys Ser Lys Lys Lys Glu Glu Glu Asp Glu Glu
180                 185                 190
Asp Glu Glu Asp Glu Glu Glu Asp Glu Glu Asp Glu Glu Asp
195                 200                 205
Glu Glu Glu Asp Asp Asp Glu
210                 215

<210> SEQ ID NO 2
<211> LENGTH: 85
<212> TYPE: PRT
<213> ORGANISM: Homo sapiens

<400> SEQUENCE: 2

Met Gly Lys Gly Asp Pro Lys Lys Pro Thr Gly Lys Met Ser Ser Tyr
  1               5                  10                  15
Ala Phe Phe Val Gln Thr Cys Arg Glu Glu His Lys Lys Lys His Pro
 20                  25                  30
Asp Ala Ser Val Asn Phe Ser Glu Phe Ser Lys Lys Cys Ser Glu Arg
 35                  40                  45
Trp Lys Thr Met Ser Ala Lys Glu Lys Gly Lys Phe Glu Asp Met Ala
 50                  55                  60
Lys Ala Asp Lys Ala Arg Tyr Glu Arg Glu Met Lys Thr Tyr Ile Pro
 65                  70                  75                  80
Pro Lys Gly Glu Thr
 85

<210> SEQ ID NO 3
<211> LENGTH: 74
<212> TYPE: PRT
<213> ORGANISM: Homo sapiens

<400> SEQUENCE: 3

Phe Lys Asp Pro Asn Ala Pro Lys Arg Leu Pro Ser Ala Phe Phe Leu
  1               5                  10                  15
Phe Cys Ser Glu Tyr Arg Pro Lys Ile Lys Gly Glu His Pro Gly Leu
 20                  25                  30
```

Ser Ile Gly Asp Val Ala Lys Lys Leu Gly Glu Met Trp Asn Asn Thr
35              40              45

Ala Ala Asp Asp Lys Gln Pro Tyr Glu Lys Lys Ala Ala Lys Leu Lys
50              55              60

Glu Lys Tyr Glu Lys Asp Ile Ala Ala Tyr
65              70

<210> SEQ ID NO 4
<211> LENGTH: 755
<212> TYPE: DNA
<213> ORGANISM: Artificial Sequence
<220> FEATURE:
<221> NAME/KEY: misc_feature
<222> LOCATION: 69
<223> OTHER INFORMATION: n = A,T,C or G
<220> FEATURE:
<223> OTHER INFORMATION: CBP-Rat HMGB1

<400> SEQUENCE: 4

```
atgaagcgac gatggaaaaa gaatttcata gccgtctcag cagccaaccg ctttaagaaa      60
atctcatcnt ccggggcact tctggttccg cgtggatcca tcgagggaag gatgggcaaa     120
ggagatccta agaagccgag aggcaaaatg tcctcatatg cattctttgt gcaaacctgc     180
cgggaggagc acaagaagaa gcacccggat gcttctgtca acttctcaga gttctccaag     240
aagtgctcag agaggtggaa gaccatgtct gctaagaaaa gggggaaatt tgaagatatg     300
gcaaaggctg acaaggctcg ttatgaaaga gaaatgaaaa cctacatccc cccaaaggg     360 gagaccaaaa agaagttcaa ggaccccaat gcccccaaga ggcctccttc ggccttcttc     420
ttgttctgtt ctgagtaccg cccaaaaatc aaggcgagc atcctggctt atccattggt     480
gatgttgcga gaaactagg agagatgtgg aacaacactg ctgcggatga caagcagccc     540
tatgaaaaga aggccgccaa gctgaaggag aagtatgaga aggatattgc tgcctacaga     600 gctaaggaa aacctgatgc agcgaaaaag ggggtggtca aggctgagaa gagcaagaaa     660
aagaaggaag aggaagacga cgaggaggat gaagaggatg aggaagagga ggaagaagag     720
gaagatgaag atgaagaaga agatgatgat gatga                                755
```

<210> SEQ ID NO 5
<211> LENGTH: 252
<212> TYPE: PRT
<213> ORGANISM: Artificial Sequence
<220> FEATURE:
<223> OTHER INFORMATION: CBP-Rat HMGB1

<400> SEQUENCE: 5

Met Lys Arg Arg Trp Lys Lys Asn Phe Ile Ala Val Ser Ala Ala Asn
1               5                   10                  15

Arg Phe Lys Lys Ile Ser Ser Ser Gly Ala Leu Leu Val Pro Arg Gly
                20              25                  30

Ser Ile Glu Gly Arg Met Gly Lys Gly Asp Pro Lys Lys Pro Arg Gly
35              40              45

Lys Met Ser Ser Tyr Ala Phe Phe Val Gln Thr Cys Arg Glu Glu His
50              55              60

Lys Lys Lys His Pro Asp Ala Ser Val Asn Phe Ser Glu Phe Ser Lys
65              70              75              80

Lys Cys Ser Glu Arg Trp Lys Thr Met Ser Ala Lys Glu Lys Gly Lys
85              90              95

Phe Glu Asp Met Ala Lys Ala Asp Lys Ala Arg Tyr Glu Arg Glu Met
100             105             110

```
Lys Thr Tyr Ile Pro Pro Lys Gly Glu Thr Lys Lys Phe Lys Asp
115                 120                 125

Pro Asn Ala Pro Lys Arg Pro Pro Ser Ala Phe Phe Leu Phe Cys Ser
130                 135                 140

Glu Tyr Arg Pro Lys Ile Lys Gly Glu His Pro Gly Leu Ser Ile Gly
145                 150                 155                 160

Asp Val Ala Lys Lys Leu Gly Glu Met Trp Asn Asn Thr Ala Ala Asp
165                 170                 175

Asp Lys Gln Pro Tyr Glu Lys Ala Ala Lys Leu Lys Glu Lys Tyr
180                 185                 190

Glu Lys Asp Ile Ala Ala Tyr Arg Ala Lys Gly Lys Pro Asp Ala Ala
195                 200                 205

Lys Lys Gly Val Val Lys Ala Glu Lys Ser Lys Lys Lys Lys Glu Glu
210                 215                 220

Glu Asp Asp Glu Glu Asp Glu Asp Glu Glu Glu Glu Glu Glu
225                 230                 235                 240

Glu Asp Glu Asp Glu Glu Glu Asp Asp Asp Glu
245                 250

<210> SEQ ID NO 6
<211> LENGTH: 336
<212> TYPE: DNA
<213> ORGANISM: Mus musculus

<400> SEQUENCE: 6
gaggttcagc tgcagcagtc tggggcagag cttgtgaagc caggggcctc agtcaagttg      60
tcctgcacag cttctggctt caacattaaa gacacctata tgcactgggt gaagcagagg     120
cctgaacagg gcctggagtg gattggaagg attgatcctg cgaatggtaa tactaaatat     180
gacccgaagt tccagggcaa ggccactata acagcagaca catcctccaa cacagcctac     240
ctgcagctca gcagcctgac atctgaggac actgccgtct attactgtgc tagggggcgct     300 tactggggcc aagggactct ggtcactgtc tctgca                                336

<210> SEQ ID NO 7
<211> LENGTH: 112
<212> TYPE: PRT
<213> ORGANISM: Mus musculus

<400> SEQUENCE: 7

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Ala Tyr Trp Gly Gln Gly Thr Leu Val Thr Val Ser Ala
            100                 105                 110

<210> SEQ ID NO 8
```

```
<211> LENGTH: 333
<212> TYPE: DNA
<213> ORGANISM: Mus musculus

<400> SEQUENCE: 8
gacattgtgc tgacccaatc tccagcttct ttggctgtgt ctctagggca gagggccacc      60
atctcctgca aggccagcca aagtgttgat tatgatggtg atagttatat gaactggtac     120
caacagaaac caggacagcc acccaaactc ctcatctatg ctgcatccaa tctagaatct     180
gggatcccag ccaggtttag tggcagtggg tctgggacag acttcaccct caacatccat     240
cctgtggagg aggaggatgc tgcaacctat tactgtcagc aaagtaatga ggatccattc     300
acgttcggct cggggacaaa gttggaaata aaa                                  333

<210> SEQ ID NO 9
<211> LENGTH: 111
<212> TYPE: PRT
<213> ORGANISM: Mus musculus

<400> SEQUENCE: 9

Asp Ile Val Leu Thr Gln Ser Pro Ala Ser Leu Ala Val Ser Leu Gly
1               5                  10                  15

Gln Arg Ala Thr Ile Ser Cys Lys Ala Ser Gln Ser Val Asp Tyr Asp
           20                  25                  30

Gly Asp Ser Tyr Met Asn Trp Tyr Gln Gln Lys Pro Gly Gln Pro Pro
       35                  40                  45

Lys Leu Leu Ile Tyr Ala Ala Ser Asn Leu Glu Ser Gly Ile Pro Ala
   50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
               85                  90                  95

Glu Asp Pro Phe Thr Phe Gly Ser Gly Thr Lys Leu Glu Ile Lys
          100                 105                 110

<210> SEQ ID NO 10
<211> LENGTH: 345
<212> TYPE: DNA
<213> ORGANISM: Mus musculus

<400> SEQUENCE: 10
caggtccagc tgcagcagtc tggacctgag ctggtgaggc ctgggacttc agtgaagata     60
tcctgcaaga cttctggcta taccttcctc acctactgga tgaactgggt gaagcagagg    120
cctggacagg gccttgagtg gattggacag atttttcctg caagtgataa tacttactac    180
aatgagatgt tcaaggacaa ggccacattg actgtagaca catcctccag cacagcctac    240
attcatctca gcagcctgac atctgaggac actgctgtct atttctgtgc aagagaggac    300
tctatggact actggggtca gggaacctca gtcaccgtca gctca                    345

<210> SEQ ID NO 11
<211> LENGTH: 115
<212> TYPE: PRT
<213> ORGANISM: Mus musculus

<400> SEQUENCE: 11

Gln Val Gln Leu Gln Gln Ser Gly Pro Glu Leu Val Arg Pro Gly Thr
1               5                  10                  15

Ser Val Lys Ile Ser Cys Lys Thr Ser Gly Tyr Thr Phe Leu Thr Tyr
```

```
                20                  25                  30

Trp Met Asn Trp Val Lys Gln Arg Pro Gly Gln Gly Leu Glu Trp Ile
 35                  40                  45

Gly Gln Ile Phe Pro Ala Ser Asp Asn Thr Tyr Tyr Asn Glu Met Phe
 50                  55                  60

Lys Asp Lys Ala Thr Leu Thr Val Asp Thr Ser Ser Thr Ala Tyr
 65                  70                  75                  80

Ile His Leu Ser Ser Leu Thr Ser Glu Asp Thr Ala Val Tyr Phe Cys
 85                  90                  95

Ala Arg Glu Asp Ser Met Asp Tyr Trp Gly Gln Gly Thr Ser Val Thr
100                 105                 110

Val Ser Ser
115

<210> SEQ ID NO 12
<211> LENGTH: 321
<212> TYPE: DNA
<213> ORGANISM: Mus musculus

<400> SEQUENCE: 12
gatattcaga tgacacagac tacatcctcc ctgtctgcct ctctgggaga cagagtcacc      60
gtcagttgca gtgcaagtcg gggcattaac aattatttaa actggtatca gcagaaacca     120
gatggaactg ttaaattcct gatctattac acatcaagtt tacactcagg agtcccatca     180
aggttcagtg gcagtgggtc tgggacagat tattctctca ccatcagcaa cctggaacct     240
gaagatattg ccacttacta ttgtcagcag tatagtaagc ttccttggac gttcggtgga     300
ggcaccaagc tggaattcaa a                                               321

<210> SEQ ID NO 13
<211> LENGTH: 107
<212> TYPE: PRT
<213> ORGANISM: Mus musculus

<400> SEQUENCE: 13

Asp Ile Gln Met Thr Gln Thr Thr Ser Ser Leu Ser Ala Ser Leu Gly
  1               5                  10                  15

Asp Arg Val Thr Val Ser Cys Ser Ala Ser Arg Gly Ile Asn Asn Tyr
 20                  25                  30

Leu Asn Trp Tyr Gln Gln Lys Pro Asp Gly Thr Val Lys Phe Leu Ile
 35                  40                  45

Tyr Tyr Thr Ser Ser Leu His Ser Gly Val Pro Ser Arg Phe Ser Gly
 50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Trp
 85                  90                  95

Thr Phe Gly Gly Gly Thr Lys Leu Glu Phe Lys
100                 105

<210> SEQ ID NO 14
<211> LENGTH: 354
<212> TYPE: DNA
<213> ORGANISM: Mus musculus

<400> SEQUENCE: 14
gaggttcagc tccagcagtc tgggactgtg ctggcaaggc ctggggcttc cgtgaagatg      60
```

-continued

```
tcctgcaagg cttctggcta cagctttacc agctactgga tgcactgggt aaaacagagg       120
cctggacagg gtctagaatg gattggtgct atttatcctg gaaatcgtga tgctagctac       180
aatcagaagt tcaagggcaa ggccaaactg actgcagtca catccgccag cactgcctac       240
ttggagctca gcagcctgac aaatgaggac tctgcggtct attactgtac aagggactac       300
ggtagtttct actttgacta ctggggccaa ggcaccactc tcacagtctc ctca             354
```

<210> SEQ ID NO 15
<211> LENGTH: 118
<212> TYPE: PRT
<213> ORGANISM: Mus musculus

<400> SEQUENCE: 15

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Gly Asn Arg Asp Ala Ser Tyr Asn Gln Lys Phe
    50                  55                  60

Lys Gly Lys Ala Lys Leu Thr Ala Val Thr Ser Ala Ser Thr Ala Tyr
65                  70                  75                  80

Leu Glu Leu Ser Ser Leu Thr Asn Glu Asp Ser Ala Val Tyr Tyr Cys
                85                  90                  95

Thr Arg Asp Tyr Gly Ser Phe Tyr Phe Asp Tyr Trp Gly Gln Gly Thr
            100                 105                 110

Thr Leu Thr Val Ser Ser
        115

<210> SEQ ID NO 16
<211> LENGTH: 321
<212> TYPE: DNA
<213> ORGANISM: Mus musculus

<400> SEQUENCE: 16

```
gatatccaga tgacacagac tacatcctcc ctgtctgcct ctctgggaga cagagtcacc       60
atcagttgca gggcaagtca ggacattagc aattatttaa actggtatca gcagaaacca       120
gatggaactg ttaaactcct gatctactac acatcaagat acactcagg agtcccatca        180
aggttcagtg gcagtgggtc tggaacagat tattctctca ccattagcaa cctggagcaa       240
gaagatattg ccacttactt ttgccaacag ggtaatacgc ttccgtggac gttcggtgga       300
ggcaccaagc tggaaatcaa a                                                  321
```

<210> SEQ ID NO 17
<211> LENGTH: 107
<212> TYPE: PRT
<213> ORGANISM: Mus musculus

<400> SEQUENCE: 17

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50              55                  60

Ser Gly Ser Gly Thr Asp Tyr Ser Leu Thr Ile Ser Asn Leu Glu Gln
65              70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
100             105

<210> SEQ ID NO 18
<211> LENGTH: 215
<212> TYPE: PRT
<213> ORGANISM: Mus musculus

<400> SEQUENCE: 18

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50              55                  60

Lys Ala Asp Lys Ala Arg Tyr Glu Arg Glu Met Lys Thr Tyr Ile Pro
65              70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Asp Asp Glu Glu
            180                 185                 190

Asp Glu Glu Asp Glu Glu Glu Glu Glu Glu Asp Glu Asp Glu
195                 200                 205

Glu Glu Asp Asp Asp Glu
210                 215

<210> SEQ ID NO 19
<211> LENGTH: 18
<212> TYPE: PRT
<213> ORGANISM: Homo sapiens

<400> SEQUENCE: 19

Met Gly Lys Gly Asp Pro Lys Lys Pro Arg Gly Lys Met Ser Ser Tyr
1               5                   10                  15

Ala Phe

<210> SEQ ID NO 20
<211> LENGTH: 18
<212> TYPE: PRT

```
<213> ORGANISM: Homo sapiens

<400> SEQUENCE: 20

Tyr Ala Phe Phe Val Gln Thr Cys Arg Glu Glu His Lys Lys His
1               5                   10                  15

Pro Asp

<210> SEQ ID NO 21
<211> LENGTH: 17
<212> TYPE: PRT
<213> ORGANISM: Homo sapiens

<400> SEQUENCE: 21

Lys Lys Lys His Pro Asp Ala Ser Val Asn Phe Ser Glu Phe Ser Lys
1               5                   10                  15

Lys

<210> SEQ ID NO 22
<211> LENGTH: 18
<212> TYPE: PRT
<213> ORGANISM: Homo sapiens

<400> SEQUENCE: 22

His Pro Asp Ala Ser Val Asn Phe Ser Glu Phe Ser Lys Lys Cys Ser
1               5                   10                  15

Glu Arg

<210> SEQ ID NO 23
<211> LENGTH: 18
<212> TYPE: PRT
<213> ORGANISM: Homo sapiens

<400> SEQUENCE: 23

Ser Glu Arg Trp Lys Thr Met Ser Ala Lys Glu Lys Gly Lys Phe Glu
1               5                   10                  15

Asp Met

<210> SEQ ID NO 24
<211> LENGTH: 18
<212> TYPE: PRT
<213> ORGANISM: Homo sapiens

<400> SEQUENCE: 24

Glu Asp Met Ala Lys Ala Asp Lys Ala Arg Tyr Glu Arg Glu Met Lys
1               5                   10                  15

Thr Tyr

<210> SEQ ID NO 25
<211> LENGTH: 18
<212> TYPE: PRT
<213> ORGANISM: Homo sapiens

<400> SEQUENCE: 25

Lys Thr Tyr Ile Pro Pro Lys Gly Glu Thr Lys Lys Lys Phe Lys Asp
1               5                   10                  15

Pro Asn

<210> SEQ ID NO 26
<211> LENGTH: 18
<212> TYPE: PRT
```

-continued

```
<400> SEQUENCE: 26

Asp Pro Asn Ala Pro Lys Arg Pro Pro Ser Ala Phe Phe Leu Phe Cys
1               5                   10                  15
Ser Glu

<210> SEQ ID NO 27
<211> LENGTH: 18
<212> TYPE: PRT
<213> ORGANISM: Homo sapiens

<400> SEQUENCE: 27

Cys Ser Glu Tyr Arg Pro Lys Ile Lys Gly Glu His Pro Gly Leu Ser
1               5                   10                  15
Ile Gly

<210> SEQ ID NO 28
<211> LENGTH: 18
<212> TYPE: PRT
<213> ORGANISM: Homo sapiens

<400> SEQUENCE: 28

Ser Ile Gly Asp Val Ala Lys Lys Leu Gly Glu Met Trp Asn Asn Thr
1               5                   10                  15
Ala Ala

<210> SEQ ID NO 29
<211> LENGTH: 18
<212> TYPE: PRT
<213> ORGANISM: Homo sapiens

<400> SEQUENCE: 29

Thr Ala Ala Asp Asp Lys Gln Pro Tyr Glu Lys Lys Ala Ala Lys Leu
1               5                   10                  15
Lys Glu

<210> SEQ ID NO 30
<211> LENGTH: 18
<212> TYPE: PRT
<213> ORGANISM: Homo sapiens

<400> SEQUENCE: 30

Leu Lys Glu Lys Tyr Glu Lys Asp Ile Ala Ala Tyr Arg Ala Lys Gly
1               5                   10                  15
Lys Pro

<210> SEQ ID NO 31
<211> LENGTH: 18
<212> TYPE: PRT
<213> ORGANISM: Homo sapiens

<400> SEQUENCE: 31

Gly Lys Pro Asp Ala Ala Lys Lys Gly Val Val Lys Ala Glu Lys Ser
1               5                   10                  15
Lys Lys

<210> SEQ ID NO 32
<211> LENGTH: 7
<212> TYPE: PRT
<213> ORGANISM: Homo sapiens
```

```
<400> SEQUENCE: 32

Glu Lys Ser Lys Lys Lys Lys
1               5

<210> SEQ ID NO 33
<211> LENGTH: 18
<212> TYPE: PRT
<213> ORGANISM: Homo sapiens

<400> SEQUENCE: 33

Ser Lys Lys Lys Lys Glu Glu Glu Glu Asp Glu Glu Asp Glu Glu Asp
1               5                   10                  15

Glu Glu

<210> SEQ ID NO 34
<211> LENGTH: 20
<212> TYPE: PRT
<213> ORGANISM: Homo sapiens

<400> SEQUENCE: 34

Asp Glu Glu Glu Glu Glu Asp Glu Glu Asp Glu Asp Glu Glu Glu Asp
1               5                   10                  15

Asp Asp Asp Glu
            20

<210> SEQ ID NO 35
<211> LENGTH: 77
<212> TYPE: PRT
<213> ORGANISM: Homo sapiens

<400> SEQUENCE: 35

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 36
<211> LENGTH: 180
<212> TYPE: PRT
<213> ORGANISM: Chinese hamster

<400> SEQUENCE: 36

Val Asn Phe Ser Glu Phe Ser Lys Lys Cys Ser Glu Arg Trp Lys Thr
1               5                   10                  15

Met Ser Ala Lys Glu Lys Gly Lys Phe Glu Asp Met Ala Lys Ala Asp
                20                  25                  30

Lys Ala Arg Tyr Glu Arg Glu Met Lys Thr Tyr Ile Pro Pro Lys Gly
            35                  40                  45

Glu Thr Lys Lys Lys Phe Lys Asp Pro Asn Ala Pro Lys Arg Pro Pro
        50                  55                  60

Ser Ala Phe Phe Leu Phe Cys Ser Glu Tyr Arg Pro Lys Ile Lys Gly
65                  70                  75                  80

Glu His Pro Gly Leu Ser Ile Gly Asp Val Ala Lys Lys Leu Gly Glu
```

```
Met Trp Asn Asn Thr Ala Ala Asp Asp Lys Gln Pro Tyr Glu Lys Lys
100                 105                 110

Ala Ala Lys Leu Lys Glu Lys Tyr Glu Lys Asp Ile Ala Ala Tyr Arg
115                 120                 125

Ala Lys Gly Lys Pro Asp Ala Ala Lys Lys Gly Val Val Lys Ala Glu
            130                 135                 140

Lys Ser Lys Lys Lys Glu Glu Glu Asp Glu Glu Asp Glu Glu Asp Glu Glu
145                 150                 155                 160

Asp Glu Glu Glu Glu Glu Glu Glu Asp Glu Asp Glu Glu Glu Asp
165                 170                 175

Asp Asp Asp Glu
180

<210> SEQ ID NO 37
<211> LENGTH: 215
<212> TYPE: PRT
<213> ORGANISM: Sus scrofa

<400> SEQUENCE: 37

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys His Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Glu Glu
195                 200                 205

Glu Glu Asp Asp Asp Asp Glu
210                 215

<210> SEQ ID NO 38
<211> LENGTH: 215
<212> TYPE: PRT
<213> ORGANISM: Bos taurus

<400> SEQUENCE: 38

Met Gly Lys Gly Asp Pro Lys Lys Pro Arg Gly Lys Met Ser Ser Tyr
```

```
                1               5              10              15
Ala Phe Phe Val Gln Thr Cys Arg Glu Glu His Lys Lys Lys His Pro
 20                  25                  30

Asp Ala Ser Val Asn Phe Ser Glu Phe Ser Lys Lys Cys Ser Glu Arg
 35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
 85                  90                  95

Arg Pro Pro Ser Ala Phe Phe Leu Phe Cys Ser Glu Tyr Arg Pro Lys
100                 105                 110

Ile Lys Gly Glu His Pro Gly Leu Ser Ile Gly Asp Val Ala Lys Lys
115                 120                 125

Leu Gly Glu Met Trp Asn Asn Thr Ala Ala Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
165                 170                 175

Lys Ala Glu Lys Ser Lys Lys Lys Lys Glu Glu Glu Glu Asp Glu Glu
180                 185                 190

Asp Glu Glu Asp Glu Glu Glu Glu Asp Glu Asp Glu Glu Glu
195                 200                 205

Glu Glu Asp Asp Asp Asp Glu
210                 215
```

<210> SEQ ID NO 39
<211> LENGTH: 690
<212> TYPE: DNA
<213> ORGANISM: Artificial Sequence
<220> FEATURE:
<223> OTHER INFORMATION: rec-HMGB1-His6

<400> SEQUENCE: 39

```
ccggaattcc tcaccatgca ccatcatcac catcacggca aaggagatcc taagaagccg      60
agaggcaaaa tgtcatcata tgcatttttt gtgcaaactt gtcgggagga gcataagaag     120
aagcacccag atgcttcagt caacttctca gagttttcta agaagtgctc agagaggtgg     180
aagaccatgt ctgctaaaga aaaggaaaa tttgaagata tggcaaaagc ggacaaggcc      240
cgttatgaaa gagaaatgaa aacctatatc cctcccaaag gggagacaaa aaagaagttc     300
aaggatccca tgcacccaa gaggcctcct tcggccttct tcctcttctg ctctgagtat      360
cgccccaaaa tcaaggaga acatcctggc ctgtccattg gtgatgttgc gaagaaactg      420
ggagagatgt ggaataacac tgctgcagat gacaagcagc cttatgaaaa gaaggctgcg     480
aagctgaagg aaaatacga aaggatata gctgcatatc gagctaaagg aaagcctgat      540
gcagcaaaaa agggagttgt caaggctgaa aaaagcaaga aaaagaagga agaggaggaa     600
gatgaggaag atgaagagga tgaggaggag gaggaagatg aagaagatga agatgaagaa     660
gaagatgatg atgatgaata atctagagca                                     690
```

<210> SEQ ID NO 40
<211> LENGTH: 221
<212> TYPE: PRT

<213> ORGANISM: Artificial Sequence
<220> FEATURE:
<223> OTHER INFORMATION: rec-HMGB1-His6

<400> SEQUENCE: 40

```
Met His His His His His Gly Lys Gly Asp Pro Lys Lys Pro Arg
1               5                   10                  15

Gly Lys Met Ser Ser Tyr Ala Phe Phe Val Gln Thr Cys Arg Glu Glu
20                  25                  30

His Lys Lys Lys His Pro Asp Ala Ser Val Asn Phe Ser Glu Phe Ser
35                  40                  45

Lys Lys Cys Ser Glu Arg Trp Lys Thr Met Ser Ala Lys Glu Lys Gly
50                  55                  60

Lys Phe Glu Asp Met Ala Lys Ala Asp Lys Ala Arg Tyr Glu Arg Glu
65                  70                  75                  80

Met Lys Thr Tyr Ile Pro Pro Lys Gly Glu Thr Lys Lys Phe Lys
85                  90                  95

Asp Pro Asn Ala Pro Lys Arg Pro Pro Ser Ala Phe Phe Leu Phe Cys
100                 105                 110

Ser Glu Tyr Arg Pro Lys Ile Lys Gly Glu His Pro Gly Leu Ser Ile
115                 120                 125

Gly Asp Val Ala Lys Lys Leu Gly Glu Met Trp Asn Asn Thr Ala Ala
130                 135                 140

Asp Asp Lys Gln Pro Tyr Glu Lys Lys Ala Ala Lys Leu Lys Glu Lys
145                 150                 155                 160

Tyr Glu Lys Asp Ile Ala Ala Tyr Arg Ala Lys Gly Lys Pro Asp Ala
165                 170                 175

Ala Lys Lys Gly Val Val Lys Ala Glu Lys Ser Lys Lys Lys Lys Glu
180                 185                 190

Glu Glu Glu Asp Glu Glu Asp Glu Glu Asp Glu Glu Glu Glu Glu Asp
195                 200                 205

Glu Glu Asp Glu Asp Glu Glu Asp Asp Asp Asp Glu
210                 215                 220
```

<210> SEQ ID NO 41
<211> LENGTH: 363
<212> TYPE: DNA
<213> ORGANISM: Mus musculus

<400> SEQUENCE: 41

```
caggttcagc tgcagcagtc tggggctgag ctggtgaggc ctgggtcctc agtgaagatt      60
tcctgcaagg cttctggcta tgcattcagt agctactgga tgaactgggt gaagcagagg     120
cctggacagg tcttgagtg gattggacag atttatcctg agatggtga  tactaactac      180 aatggaaagt tcaagggtaa agccacactg acttcagaca atcctccag cacagcctac      240 atgcagctca gcagcctaac atctgaggac tctgcggtct atttctgtgc aagaagggag     300
ccttatggta gctacgtggg gtttggtttc tggggccaag ggactctggt cactgtctct     360
gca                                                                   363
```

<210> SEQ ID NO 42
<211> LENGTH: 121
<212> TYPE: PRT
<213> ORGANISM: Mus musculus

<400> SEQUENCE: 42

Gln Val Gln Leu Gln Gln Ser Gly Ala Glu Leu Val Arg Pro Gly Ser

```
                1               5                   10                  15

Ser Val Lys Ile Ser Cys Lys Ala Ser Gly Tyr Ala Phe Ser Ser Tyr
 20                  25                  30

Trp Met Asn Trp Val Lys Gln Arg Pro Gly Gln Gly Leu Glu Trp Ile
 35                  40                  45

Gly Gln Ile Tyr Pro Gly Asp Gly Asp Thr Asn Tyr Asn Gly Lys Phe
 50                  55                  60

Lys Gly Lys Ala Thr Leu Thr Ser Asp Lys Ser Ser Thr Ala Tyr
 65                  70                  75                  80

Met Gln Leu Ser Ser Leu Thr Ser Glu Asp Ser Ala Val Tyr Phe Cys
 85                  90                  95

Ala Arg Arg Glu Pro Tyr Gly Ser Tyr Val Gly Phe Gly Phe Trp Gly
100                 105                 110

Gln Gly Thr Leu Val Thr Val Ser Ala
115                 120

<210> SEQ ID NO 43
<211> LENGTH: 318
<212> TYPE: DNA
<213> ORGANISM: Mus musculus

<400> SEQUENCE: 43
gaaaatgttc tcacccagtc tccagcaatc atgtctgcat ctccagggga aaaggtcacc       60
atgacctgca gtgccagttc aagtgtaagt tacatgcact ggtaccagca aaagtcaagc      120
acctccccca aactctggat ttatgacaca tccaaactgg cttctggagt cccaggtcgc      180
ttcagtggca gtgggtctgg aaactcttac tctctcacga tcagcagcat ggaggctgaa      240
gatgttgcca cttattactg ttttcagggg agtgggtacc caccacgtt cggagggggg      300 accaagctgg aaataaaa                                                    318

<210> SEQ ID NO 44
<211> LENGTH: 106
<212> TYPE: PRT
<213> ORGANISM: Mus musculus

<400> SEQUENCE: 44

Glu Asn Val Leu Thr Gln Ser Pro Ala Ile Met Ser Ala Ser Pro Gly
  1               5                  10                  15

Glu Lys Val Thr Met Thr Cys Ser Ala Ser Ser Ser Val Ser Tyr Met
 20                  25                  30

His Trp Tyr Gln Gln Lys Ser Ser Thr Ser Pro Lys Leu Trp Ile Tyr
 35                  40                  45

Asp Thr Ser Lys Leu Ala Ser Gly Val Pro Gly Arg Phe Ser Gly Ser
 50                  55                  60

Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Ser Gly Tyr Pro Pro Thr
 85                  90                  95

Phe Gly Gly Gly Thr Lys Leu Glu Ile Lys
100                 105

<210> SEQ ID NO 45
<211> LENGTH: 18
<212> TYPE: PRT
<213> ORGANISM: Artificial Sequence
<220> FEATURE:
<223> OTHER INFORMATION: Human HMGB1-46-63-scr
```

```
<400> SEQUENCE: 45

Arg Met Lys Glu Glu Ser Ser Ala Lys Asp Gly Trp Phe Thr Glu Met
1               5                   10                  15

Lys Lys

<210> SEQ ID NO 46
<211> LENGTH: 18
<212> TYPE: PRT
<213> ORGANISM: Homo sapiens

<400> SEQUENCE: 46

Glu Phe Ser Lys Lys Cys Ser Glu Arg Trp Lys Thr Met Ser Ala Lys
1               5                   10                  15

Glu Lys

<210> SEQ ID NO 47
<211> LENGTH: 18
<212> TYPE: PRT
<213> ORGANISM: Homo sapiens

<400> SEQUENCE: 47

Ser Ala Lys Glu Lys Gly Lys Phe Glu Asp Met Ala Lys Ala Asp Lys
1               5                   10                  15

Ala Arg

<210> SEQ ID NO 48
<211> LENGTH: 18
<212> TYPE: PRT
<213> ORGANISM: Homo sapiens

<400> SEQUENCE: 48

Ser Glu Arg Trp Lys Thr Met Ser Ala Lys Glu Lys Ser Lys Phe Glu
1               5                   10                  15

Asp Met

<210> SEQ ID NO 49
<211> LENGTH: 18
<212> TYPE: PRT
<213> ORGANISM: Artificial Sequence
<220> FEATURE:
<223> OTHER INFORMATION: Human HMGB1-61-78_scr

<400> SEQUENCE: 49

Ala Lys Asp Tyr Met Glu Ala Arg Lys Asp Thr Glu Tyr Lys Met Ala
1               5                   10                  15

Arg Glu

<210> SEQ ID NO 50
<211> LENGTH: 18
<212> TYPE: PRT
<213> ORGANISM: Homo sapiens

<400> SEQUENCE: 50

Asp Lys Ala Arg Tyr Glu Arg Glu Met Lys Thr Tyr Ile Pro Pro Lys
1               5                   10                  15

Gly Glu

<210> SEQ ID NO 51
<211> LENGTH: 18
<212> TYPE: PRT
```

<213> ORGANISM: Artificial Sequence
<220> FEATURE:
<223> OTHER INFORMATION: Human HMGB1-151-168_scr

<400> SEQUENCE: 51

```
Lys Glu Tyr Arg Glu Pro Lys Tyr Ala Ile Lys Ala Lys Lys Gly Leu
1               5                   10                  15
Asp Ala
```

<210> SEQ ID NO 52
<211> LENGTH: 18
<212> TYPE: PRT
<213> ORGANISM: Homo sapiens

<400> SEQUENCE: 52

```
Pro Tyr Glu Lys Lys Ala Ala Lys Leu Lys Glu Lys Tyr Glu Lys Asp
1               5                   10                  15
Ile Ala
```

<210> SEQ ID NO 53
<211> LENGTH: 18
<212> TYPE: PRT
<213> ORGANISM: Homo sapiens

<400> SEQUENCE: 53

```
Lys Asp Ile Ala Ala Tyr Arg Ala Lys Gly Lys Pro Asp Ala Ala Lys
1               5                   10                  15
Lys Gly
```

<210> SEQ ID NO 54
<211> LENGTH: 209
<212> TYPE: PRT
<213> ORGANISM: Homo sapiens

<400> SEQUENCE: 54

```
Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
```

-continued

```
            180                 185                 190
Glu Glu Glu Glu Glu Asp Glu Asp Glu Glu Glu Asp Glu Asp Glu
        195                 200                 205
Glu

<210> SEQ ID NO 55
<211> LENGTH: 54
<212> TYPE: PRT
<213> ORGANISM: Homo sapiens

<400> SEQUENCE: 55

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
        20                  25                  30

Ala Lys Ala Asp Lys Ala Arg Tyr Glu Arg Glu Met Lys Thr Tyr Ile
    35                  40                  45

Pro Pro Lys Gly Glu Thr
50

<210> SEQ ID NO 56
<211> LENGTH: 53
<212> TYPE: PRT
<213> ORGANISM: Homo sapiens

<400> SEQUENCE: 56

Asp Ser Ser Val Asn Phe Ala Glu Phe Ser Lys Lys Cys Ser Glu Arg
1               5                   10                  15

Trp Lys Thr Met Ser Ala Lys Glu Lys Ser Lys Phe Glu Asp Met Ala
        20                  25                  30

Lys Ser Asp Lys Ala Arg Tyr Asp Arg Glu Met Lys Asn Tyr Val Pro
    35                  40                  45

Pro Lys Gly Asp Lys
50

<210> SEQ ID NO 57
<211> LENGTH: 54
<212> TYPE: PRT
<213> ORGANISM: Homo sapiens

<400> SEQUENCE: 57

Pro Glu Val Pro Val Asn Phe Ala Glu Phe Ser Lys Lys Cys Ser Glu
1               5                   10                  15

Arg Trp Lys Thr Val Ser Gly Lys Glu Lys Ser Lys Phe Asp Glu Met
        20                  25                  30

Ala Lys Ala Asp Lys Val Arg Tyr Asp Arg Glu Met Lys Asp Tyr Gly
    35                  40                  45

Pro Ala Lys Gly Gly Lys
50

<210> SEQ ID NO 58
<211> LENGTH: 54
<212> TYPE: PRT
<213> ORGANISM: Homo sapiens

<400> SEQUENCE: 58

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
```

```
                20                  25                  30

Ala Lys Ala Asp Lys Ala Arg Tyr Glu Arg Glu Met Lys Thr Tyr Ile
 35                  40                  45

Pro Pro Lys Gly Glu Thr
 50

<210> SEQ ID NO 59
<211> LENGTH: 53
<212> TYPE: PRT
<213> ORGANISM: Homo sapiens

<400> SEQUENCE: 59

Ser Asp Ala Ser Val Asn Phe Ser Glu Phe Ser Asn Lys Cys Ser Glu
 1               5                  10                  15

Arg Trp Lys Met Ser Ala Lys Glu Lys Gly Lys Phe Glu Asp Met Ala
            20                  25                  30

Lys Ala Asp Lys Thr His Tyr Glu Arg Gln Met Lys Thr Tyr Ile Pro
 35                  40                  45

Pro Lys Gly Glu Thr
 50

<210> SEQ ID NO 60
<211> LENGTH: 54
<212> TYPE: PRT
<213> ORGANISM: Homo sapiens

<400> SEQUENCE: 60

Pro Asp Ala Ser Val Asn Phe Ser Glu Phe Ser Lys Lys Cys Ser Glu
 1               5                  10                  15

Arg Trp Lys Ala Met Ser Ala Lys Asp Lys Gly Lys Phe Glu Asp Met
            20                  25                  30

Ala Lys Val Asp Lys Ala Asp Tyr Glu Arg Glu Met Lys Thr Tyr Ile
 35                  40                  45

Pro Pro Lys Gly Glu Thr
 50

<210> SEQ ID NO 61
<211> LENGTH: 54
<212> TYPE: PRT
<213> ORGANISM: Homo sapiens

<400> SEQUENCE: 61

Pro Asp Ala Ser Val Lys Phe Ser Glu Phe Leu Lys Lys Cys Ser Glu
 1               5                  10                  15

Thr Trp Lys Thr Ile Phe Ala Lys Glu Lys Gly Lys Phe Glu Asp Met
            20                  25                  30

Ala Lys Ala Asp Lys Ala His Tyr Glu Arg Glu Met Lys Thr Tyr Ile
 35                  40                  45

Pro Pro Lys Gly Glu Lys
 50

<210> SEQ ID NO 62
<211> LENGTH: 54
<212> TYPE: PRT
<213> ORGANISM: Homo sapiens

<400> SEQUENCE: 62

Pro Asp Ala Ser Ile Asn Phe Ser Glu Phe Ser Gln Lys Cys Pro Glu
 1               5                  10                  15
```

```
Thr Trp Lys Thr Thr Ile Ala Lys Glu Lys Gly Lys Phe Glu Asp Met
 20                  25                  30

Ala Lys Ala Asp Lys Ala His Tyr Glu Arg Glu Met Lys Thr Tyr Ile
 35                  40                  45

Pro Pro Lys Gly Glu Thr
 50

<210> SEQ ID NO 63
<211> LENGTH: 38
<212> TYPE: PRT
<213> ORGANISM: Homo sapiens

<400> SEQUENCE: 63

Pro Asp Ala Ser Val Asn Ser Ser Glu Phe Ser Lys Lys Cys Ser Glu
 1               5                  10                  15

Arg Trp Lys Thr Met Pro Thr Lys Gln Gly Lys Phe Glu Asp Met Ala
 20                  25                  30

Lys Ala Asp Arg Ala His
 35

<210> SEQ ID NO 64
<211> LENGTH: 54
<212> TYPE: PRT
<213> ORGANISM: Homo sapiens

<400> SEQUENCE: 64

Pro Asp Ala Ser Val Asn Phe Ser Glu Phe Ser Lys Lys Cys Leu Val
 1               5                  10                  15

Arg Gly Lys Thr Met Ser Ala Lys Glu Lys Gly Gln Phe Glu Ala Met
 20                  25                  30

Ala Arg Ala Asp Lys Ala Arg Tyr Glu Arg Glu Met Lys Thr Tyr Ile
 35                  40                  45

Pro Pro Lys Gly Glu Thr
 50

<210> SEQ ID NO 65
<211> LENGTH: 54
<212> TYPE: PRT
<213> ORGANISM: Homo sapiens

<400> SEQUENCE: 65

Leu Asp Ala Ser Val Ser Phe Ser Glu Phe Ser Asn Lys Cys Ser Glu
 1               5                  10                  15

Arg Trp Lys Thr Met Ser Val Lys Glu Lys Gly Lys Phe Glu Asp Met
 20                  25                  30

Ala Lys Ala Asp Lys Ala Cys Tyr Glu Arg Glu Met Lys Ile Tyr Pro
 35                  40                  45

Tyr Leu Lys Gly Arg Gln
 50

<210> SEQ ID NO 66
<211> LENGTH: 84
<212> TYPE: PRT
<213> ORGANISM: Homo sapiens

<400> SEQUENCE: 66

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
 20                  25                  30
```

```
Ala Ser Val Asn Phe Ser Glu Phe Ser Lys Lys Cys Ser Glu Arg Trp
 35                  40                  45

Lys Thr Met Ser Ala Lys Glu Lys Gly Lys Phe Glu Asp Met Ala Lys
 50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 67
<211> LENGTH: 74
<212> TYPE: PRT
<213> ORGANISM: Homo sapiens

<400> SEQUENCE: 67

Phe Lys Asp Pro Asn Ala Pro Lys Arg Pro Pro Ser Ala Phe Phe Leu
 1               5                  10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
 35                  40                  45

Ala Ala Asp Asp Lys Gln Pro Tyr Glu Lys Lys Ala Ala Lys Leu Lys
 50                  55                  60

Glu Lys Tyr Glu Lys Asp Ile Ala Ala Tyr
 65                  70

<210> SEQ ID NO 68
<211> LENGTH: 74
<212> TYPE: PRT
<213> ORGANISM: Homo sapiens

<400> SEQUENCE: 68

Lys Lys Asp Pro Asn Ala Pro Lys Arg Pro Pro Ser Ala Phe Phe Leu
 1               5                  10                  15

Phe Cys Ser Glu His Arg Pro Lys Ile Lys Ser Glu His Pro Gly Leu
                20                  25                  30

Ser Ile Gly Asp Thr Ala Lys Lys Leu Gly Glu Met Trp Ser Glu Gln
 35                  40                  45

Ser Ala Lys Asp Lys Gln Pro Tyr Glu Gln Lys Ala Ala Lys Leu Lys
 50                  55                  60

Glu Lys Tyr Glu Lys Asp Ile Ala Ala Tyr
 65                  70

<210> SEQ ID NO 69
<211> LENGTH: 74
<212> TYPE: PRT
<213> ORGANISM: Homo sapiens

<400> SEQUENCE: 69

Phe Lys Asp Pro Asn Ala Pro Lys Arg Leu Pro Ser Ala Phe Phe Leu
 1               5                  10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
 35                  40                  45

Ala Ala Asp Asp Lys Gln Pro Tyr Glu Lys Lys Ala Ala Lys Leu Lys
 50                  55                  60

Glu Lys Tyr Glu Lys Asp Ile Ala Ala Tyr
```

```
65                      70

<210> SEQ ID NO 70
<211> LENGTH: 74
<212> TYPE: PRT
<213> ORGANISM: Homo sapiens

<400> SEQUENCE: 70

Phe Lys Asp Pro Asn Ala Pro Lys Arg Pro Pro Ser Ala Phe Phe Leu
1               5                   10                  15

Phe Cys Ser Glu Tyr His Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Gly Glu Lys Lys Ala Ala Lys Leu Lys
        50                  55                  60

Glu Lys Tyr Glu Lys Asp Ile Ala Ala Tyr
65                      70

<210> SEQ ID NO 71
<211> LENGTH: 74
<212> TYPE: PRT
<213> ORGANISM: Homo sapiens

<400> SEQUENCE: 71

Phe Lys Asp Ser Asn Ala Pro Lys Arg Pro Pro Ser Ala Phe Leu Leu
1               5                   10                  15

Phe Cys Ser Glu Tyr Cys Pro Lys Ile Lys Gly Glu His Pro Gly Leu
                20                  25                  30

Pro Ile Ser Asp Val Ala Lys Lys Leu Val Glu Met Trp Asn Asn Thr
            35                  40                  45

Phe Ala Asp Asp Lys Gln Leu Cys Glu Lys Lys Ala Ala Lys Leu Lys
        50                  55                  60

Glu Lys Tyr Lys Lys Asp Thr Ala Thr Tyr
65                      70

<210> SEQ ID NO 72
<211> LENGTH: 74
<212> TYPE: PRT
<213> ORGANISM: Homo sapiens

<400> SEQUENCE: 72

Phe Lys Asp Pro Asn Ala Pro Lys Arg Pro Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Val Lys Lys Leu Ala Gly Met Trp Asn Asn Thr
            35                  40                  45

Ala Ala Ala Asp Lys Gln Phe Tyr Glu Lys Lys Ala Ala Lys Leu Lys
        50                  55                  60

Glu Lys Tyr Lys Lys Asp Ile Ala Ala Tyr
65                      70

<210> SEQ ID NO 73
<211> LENGTH: 92
<212> TYPE: PRT
<213> ORGANISM: Homo sapiens

<400> SEQUENCE: 73
```

```
Phe Lys Asp Pro Asn Ala Pro Lys Arg Pro Ser Ala Phe Phe Leu
1               5                   10                  15

Phe Cys Ser Glu Tyr Arg Pro Lys Ile Lys Gly Glu His Pro Gly Leu
            20                  25                  30

Ser Ile Gly Asp Val Ala Lys Lys Leu Gly Glu Met Trp Asn Asn Thr
35                  40                  45

Ala Ala Asp Asp Lys Gln Pro Tyr Glu Lys Lys Ala Ala Lys Leu Lys
50                  55                  60

Glu Lys Tyr Glu Lys Asp Ile Ala Ala Tyr Arg Ala Lys Gly Lys Pro
65                  70                  75                  80

Asp Ala Ala Lys Lys Gly Val Val Lys Ala Glu Lys
85                  90

<210> SEQ ID NO 74
<211> LENGTH: 215
<212> TYPE: PRT
<213> ORGANISM: Homo sapiens

<400> SEQUENCE: 74

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
85                  90                  95

Arg Pro Pro Ser Ala Phe Phe Leu Phe Cys Ser Glu Tyr Arg Pro Lys
100                 105                 110

Ile Lys Gly Glu His Pro Gly Leu Ser Ile Gly Asp Val Ala Lys Lys
115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
165                 170                 175

Lys Ala Glu Lys Ser Lys Lys Lys Glu Glu Glu Asp Glu Glu
180                 185                 190

Asp Glu Glu Asp Glu Glu Glu Glu Asp Glu Asp Glu Asp Glu
195                 200                 205

Glu Glu Asp Asp Asp Asp Glu
210                 215

<210> SEQ ID NO 75
<211> LENGTH: 77
<212> TYPE: PRT
<213> ORGANISM: Homo sapiens

<400> SEQUENCE: 75

Pro Arg Gly Lys Met Ser Ser Tyr Ala Phe Phe Val Gln Thr Cys Arg
1               5                   10                  15
```

-continued

```
Glu Glu His Lys Lys Lys His Pro Asp Ala Ser Val Asn Phe Ser Glu
 20              25                  30

Phe Ser Lys Lys Cys Ser Glu Arg Trp Lys Thr Met Ser Ala Lys Glu
 35              40                  45

Lys Gly Lys Phe Glu Asp Met Ala Lys Ala Asp Lys Ala Arg Tyr Glu
 50              55                  60

Arg Glu Met Lys Thr Tyr Ile Pro Pro Lys Gly Glu Thr
 65              70                  75

<210> SEQ ID NO 76
<211> LENGTH: 74
<212> TYPE: PRT
<213> ORGANISM: Homo sapiens

<400> SEQUENCE: 76

Phe Lys Asp Pro Asn Ala Pro Lys Arg Pro Pro Ser Ala Phe Phe Leu
 1               5                  10                  15

Phe Cys Ser Glu Tyr Arg Pro Lys Ile Lys Gly Glu His Pro Gly Leu
 20              25                  30

Ser Ile Gly Asp Val Ala Lys Lys Leu Gly Glu Met Trp Asn Asn Thr
 35              40                  45

Ala Ala Asp Asp Lys Gln Pro Tyr Glu Lys Lys Ala Ala Lys Leu Lys
 50              55                  60

Glu Lys Tyr Glu Lys Asp Ile Ala Ala Tyr
 65              70
```